(12) United States Patent
Bentley et al.

(10) Patent No.: US 10,881,908 B2
(45) Date of Patent: *Jan. 5, 2021

(54) MOTION CAPTURE DATA FITTING SYSTEM

(71) Applicant: BLAST MOTION INC., Carlsbad, CA (US)

(72) Inventors: Michael Bentley, Carlsbad, CA (US); Bhaskar Bose, Carlsbad, CA (US); Ryan Kaps, Mesa, AZ (US)

(73) Assignee: BLAST MOTION INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,631

(22) Filed: Jul. 16, 2019

(65) Prior Publication Data

US 2020/0047029 A1 Feb. 13, 2020

Related U.S. Application Data

(63) Continuation of application No. 15/812,926, filed on Nov. 14, 2017, now Pat. No. 10,350,455, which is a
(Continued)

(51) Int. Cl.
*A63B 24/00* (2006.01)
*G01P 13/00* (2006.01)
(Continued)

(52) U.S. Cl.
CPC ............ *A63B 24/0062* (2013.01); *A61B 5/11* (2013.01); *A61B 5/6895* (2013.01); *G01P 13/00* (2013.01); *A61B 5/742* (2013.01)

(58) Field of Classification Search
None
See application file for complete search history.

(56) References Cited

U.S. PATENT DOCUMENTS 1,712,537 A 5/1929 White
3,182,508 A 5/1965 Varju
(Continued)

FOREIGN PATENT DOCUMENTS

EP 2025369 A2 2/2009
EP 2479993 7/2012
(Continued)

OTHER PUBLICATIONS

International Search Report received in PCT/US2016/042668, dated Oct. 4, 2016, 21 pages.
(Continued)

*Primary Examiner* — Frederick D Bailey
(74) *Attorney, Agent, or Firm* — Arc IP Law, PC; Joseph J. Mayo

(57) ABSTRACT

Enables a fitting system for sporting equipment using an application that executes on a mobile phone for example to prompt and accept motion inputs from a given motion capture sensor to measure a user's size, range of motion, speed and then utilizes that same sensor to capture motion data from a piece of equipment, for example to further optimize the fit of, or suggest purchase of a particular piece of sporting equipment. Utilizes correlation or other data mining of motion data for size, range of motion, speed of other users to maximize the fit of a piece of equipment for the user based on other user's performance with particular equipment. For example, this enables a user of a similar size, range of motion and speed to data mine for the best performance equipment, e.g., longest drive, lowest putt scores, highest winning percentage, etc., associated with other users having similar characteristics.

23 Claims, 38 Drawing Sheets
(25 of 38 Drawing Sheet(s) Filed in Color)

Related U.S. Application Data continuation of application No. 15/044,036, filed on Feb. 15, 2016, now Pat. No. 9,814,935, which is a continuation of application No. 13/757,029, filed on Feb. 1, 2013, now Pat. No. 9,261,526, which is a continuation-in-part of application No. 13/737,956, filed on Jan. 10, 2013, now Pat. No. 8,827,824, which is a continuation-in-part of application No. 13/679,879, filed on Nov. 16, 2012, now Pat. No. 8,944,928, which is a continuation-in-part of application No. 13/298,158, filed on Nov. 16, 2011, now Pat. No. 8,905,855, which is a continuation-in-part of application No. 13/267,784, filed on Oct. 6, 2011, now Pat. No. 9,604,142, which is a continuation-in-part of application No. 13/219,525, filed on Aug. 26, 2011, now Pat. No. 8,941,723, which is a continuation-in-part of application No. 13/191,309, filed on Jul. 26, 2011, now Pat. No. 9,033,810, which is a continuation-in-part of application No. 13/048,850, filed on Mar. 15, 2011, now Pat. No. 8,465,376, which is a continuation-in-part of application No. 12/901,806, filed on Oct. 11, 2010, now Pat. No. 9,320,957, which is a continuation-in-part of application No. 12/868,882, filed on Aug. 26, 2010, now Pat. No. 8,994,826.

(51) Int. Cl.
*A61B 5/11* (2006.01)
*A61B 5/00* (2006.01)

(56) References Cited

U.S. PATENT DOCUMENTS

| | | |
|---|---|---|
| 3,226,704 A | 12/1965 | Petrash |
| 3,270,564 A | 9/1966 | Evans |
| 3,776,556 A | 12/1973 | McLaughlin |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,515,365 A | 5/1985 | Horikoshi et al. |
| 4,759,219 A | 7/1988 | Cobb et al. |
| 4,898,389 A | 2/1990 | Plutt |
| 4,902,014 A | 2/1990 | Bontomase et al. |
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashima et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,443,260 A | 8/1995 | Stewart et al. |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,707,299 A | 1/1998 | McKenna |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,993,333 A | 11/1999 | Heckaman |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,253,159 B1 | 6/2001 | Bett et al. |
| 6,254,492 B1 | 7/2001 | Taggett |
| 6,266,623 B1 | 7/2001 | Vock et al. |
| 6,292,130 B1 | 9/2001 | Cavallaro et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Anttila |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,205,894 B1 | 4/2007 | Savage |
| 7,212,943 B2 | 5/2007 | Aoshima et al. |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | Mcnitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,731,598 B1 | 6/2010 | Kim et al. |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |

(56) References Cited

U.S. PATENT DOCUMENTS

| | | |
|---|---|---|
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk |
| 8,352,211 B2 | 1/2013 | Vock et al. |
| 8,400,548 B2 | 3/2013 | Bilbrey et al. |
| 8,425,292 B2 | 4/2013 | Lui et al. |
| 8,477,027 B2 | 7/2013 | Givens |
| 8,527,228 B2 | 9/2013 | Panagas |
| 8,565,483 B2 | 10/2013 | Nakaoka |
| 8,589,114 B2 | 11/2013 | Papadourakis |
| 8,696,482 B1 | 4/2014 | Pedenko et al. |
| 8,723,986 B1 | 5/2014 | Merrill |
| 8,725,452 B2 | 5/2014 | Han |
| 8,764,576 B2 | 7/2014 | Takasugi |
| 8,781,610 B2 | 7/2014 | Han |
| 8,831,905 B2 | 9/2014 | Papadourakis |
| 8,876,621 B2 | 11/2014 | Shibuya |
| 8,888,603 B2 | 11/2014 | Sato et al. |
| 8,905,856 B2 | 12/2014 | Parke et al. |
| 8,929,709 B2 | 1/2015 | Lokshin |
| 8,944,932 B2 | 2/2015 | Sato et al. |
| 8,944,939 B2 | 2/2015 | Clark et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,032,794 B2 | 5/2015 | Perkins et al. |
| 9,060,682 B2 | 6/2015 | Lokshin |
| 9,146,134 B2 | 9/2015 | Lokshin et al. |
| 9,646,199 B2 | 5/2017 | Bose et al. |
| 9,656,122 B2 | 5/2017 | Papadourakis |
| 10,124,230 B2 | 5/2018 | Thornbrue et al. |
| 10,460,157 B2 | 10/2019 | Matsunaga et al. |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty |
| 2003/0074659 A1 | 4/2003 | Louzoun |
| 2003/0109322 A1 | 6/2003 | Funk et al. |
| 2003/0163287 A1 | 8/2003 | Vock et al. |
| 2003/0191547 A1 | 10/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1 | 8/2006 | Hunter et al. |
| 2006/0199659 A1 | 9/2006 | Caldwell |
| 2006/0247070 A1 | 11/2006 | Funk et al. |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2006/0293112 A1 | 12/2006 | Yi |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1 | 11/2007 | Bentley |
| 2007/0298896 A1 | 12/2007 | Nusbaum |
| 2008/0027502 A1 | 1/2008 | Ransom |
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0182685 A1 | 7/2008 | Marty et al. |
| 2008/0190202 A1 | 8/2008 | Kulach et al. |
| 2008/0211768 A1 | 9/2008 | Breen et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0144785 A1 | 6/2009 | Walker et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |

(56) References Cited

U.S. PATENT DOCUMENTS

| | | |
|---|---|---|
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0144457 A1 | 6/2010 | Kim |
| 2010/0178994 A1 | 7/2010 | Do et al. |
| 2010/0201512 A1 | 8/2010 | Stirling et al. |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0309097 A1 | 12/2010 | Raviv et al. |
| 2010/0323794 A1 | 12/2010 | Su |
| 2011/0004871 A1 | 1/2011 | Liu |
| 2011/0029235 A1 | 2/2011 | Berry |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0126184 A1 | 5/2011 | Lisboa |
| 2011/0165998 A1 | 7/2011 | Lau et al. |
| 2011/0195780 A1 | 8/2011 | Lu |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2011/0238308 A1 | 9/2011 | Miller et al. |
| 2012/0004034 A1 | 1/2012 | Pope et al. |
| 2012/0023354 A1 | 1/2012 | Chino |
| 2012/0052972 A1 | 3/2012 | Bentley |
| 2012/0088544 A1 | 4/2012 | Bentley et al. |
| 2012/0115626 A1 | 5/2012 | Davenport |
| 2012/0115682 A1 | 5/2012 | Homsi |
| 2012/0116548 A1 | 5/2012 | Goree et al. |
| 2012/0120572 A1 | 5/2012 | Bentley |
| 2012/0142415 A1 | 6/2012 | Lindsay |
| 2012/0157241 A1 | 6/2012 | Nomura et al. |
| 2012/0179418 A1 | 7/2012 | Takasugi et al. |
| 2012/0179742 A1 | 7/2012 | Acharya et al. |
| 2012/0191405 A1 | 7/2012 | Molyneux et al. |
| 2012/0295726 A1 | 11/2012 | Cherbini |
| 2012/0316004 A1 | 12/2012 | Shibuya |
| 2013/0029791 A1 | 1/2013 | Rose et al. |
| 2013/0095924 A1 | 4/2013 | Geisner et al. |
| 2013/0095941 A1 | 4/2013 | Bentley et al. |
| 2013/0110415 A1 | 5/2013 | Davis et al. |
| 2013/0128022 A1 | 5/2013 | Bose et al. |
| 2013/0173212 A1 | 7/2013 | Saiki et al. |
| 2013/0178304 A1 | 7/2013 | Chan |
| 2013/0191063 A1 | 7/2013 | Nomura |
| 2013/0225309 A1 | 8/2013 | Bentley et al. |
| 2013/0245966 A1 | 9/2013 | Burroughs et al. |
| 2013/0267335 A1 | 10/2013 | Boyd et al. |
| 2013/0271602 A1 | 10/2013 | Bentley et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0343729 A1 | 12/2013 | Rav-Acha et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1 | 5/2014 | Shibuya et al. |
| 2014/0156214 A1 | 6/2014 | Nomura |
| 2014/0172873 A1 | 6/2014 | Varoglu et al. |
| 2014/0200092 A1 | 7/2014 | Parke et al. |
| 2014/0200094 A1 | 7/2014 | Parke et al. |
| 2014/0213382 A1 | 7/2014 | Kang et al. |
| 2014/0229135 A1 | 8/2014 | Nomura |
| 2014/0229138 A1 | 8/2014 | Goree et al. |
| 2014/0257743 A1 | 9/2014 | Lokshin et al. |
| 2014/0257744 A1 | 9/2014 | Lokshin et al. |
| 2014/0334796 A1 | 11/2014 | Galant et al. |
| 2014/0376876 A1 | 12/2014 | Bentley et al. |
| 2014/0378239 A1 | 12/2014 | Sato et al. |
| 2014/0379293 A1 | 12/2014 | Sato |
| 2014/0379294 A1 | 12/2014 | Shibuya et al. |
| 2014/0379295 A1 | 12/2014 | Sato et al. |
| 2015/0007658 A1 | 1/2015 | Ishikawa et al. |
| 2015/0012240 A1 | 1/2015 | Sato |
| 2015/0042481 A1 | 2/2015 | Nomura |
| 2015/0098688 A1 | 4/2015 | Lokshin |
| 2015/0124048 A1 | 5/2015 | King |
| 2015/0131845 A1 | 5/2015 | Forouhar et al. |
| 2015/0348591 A1 | 5/2015 | King |
| 2015/0256689 A1 | 9/2015 | Erkkila et al. |
| 2015/0258402 A1 | 9/2015 | Bynum |
| 2017/0061817 A1 | 3/2017 | Mettler |
| 2017/0157484 A1 | 6/2017 | Altshuler et al. |
| 2018/0021648 A1 | 1/2018 | Thornbrue et al. |
| 2018/0021653 A1 | 1/2018 | Thornbrue et al. |
| 2018/0070056 A1 | 3/2018 | DeAngelis et al. |

FOREIGN PATENT DOCUMENTS

| | | |
|---|---|---|
| EP | 2652738 | 10/2013 |
| EP | 2781240 | 9/2014 |
| JP | 2002210055 A | 7/2002 |
| JP | 2004207985 | 7/2004 |
| JP | 2005176030 | 6/2005 |
| JP | 2011000367 | 1/2011 |
| JP | 2012196241 | 10/2012 |
| JP | 2013188426 | 9/2013 |
| KR | 10-20030085275 | 11/2003 |
| KR | 10-20060041060 | 5/2006 |
| KR | 10-20070119018 | 12/2007 |
| KR | 10-20100074068 | 7/2010 |
| KR | 101079319 | 6/2011 |
| KR | 10-20100020131 | 9/2011 |
| WO | 1994027683 | 12/1994 |
| WO | 2007130057 A1 | 11/2007 |
| WO | 2009056688 A1 | 5/2009 |
| WO | 2011057194 | 5/2011 |
| WO | 2014085744 A1 | 6/2014 |

OTHER PUBLICATIONS

International Search Report received in PCT/US2016/042671, dated Oct. 13, 2016, 17 pages.
International Search Report and Written Opinion received in PCT/US2016/042676, dated Oct. 24, 2016 (12 pages).
International Preliminary Report on Patentability received in PCT/US2015/026917, dated Nov. 3, 2016 (5 pages).
International Search Report received for PCT Application No. PCT/US2012/065716, dated Jan. 3, 2013, 10 pages.
MyCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, dated Mar. 6, 2012, 8 pages.
International Search Report received for PCT Application No. PCT/U52011/049461, dated Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.

(56) References Cited

OTHER PUBLICATIONS

International Search Report for PCT Application No. PCT/US2013/021999, dated Apr. 30, 2013, 8 pages.
International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
MiCoach Pacer User Manual, 31 pages, (2009).
Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
Trace—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
Pocketpro Golf Designs, PocketPro Full Swing Analysis in Your Pocket, www.PocketPro.org, (2011).
Clemson University, Golf Shot Tutorial, http://www.webnucleo.org/home/online_tools/newton/0.4/html/about_this_tool/tutorials/golf_1.shp.cgi, retrieved on Nov. 10, 2011.
MiCoach SPEED_CELL TM, User Manual, 23 pages, (2011).
Nike+iPod, User Guide, 32 pages (2010).
SureShotGPS SS9000X, Intelligent Touch, Instruction Manual, 25 page, 2011.
ActiveReplay, "TRACE—The Most Advanced Activity Monitor for Action Sports", http://www.kickstarter.com/projects/activereplay/trace-the-most-advanced-activity-monitor-for-actio, 13 pages, Oct. 1, 2013.
ZEPP Golfsense@Launch2011, https://www.youtube.com/watch?v=VnOcu8szjIk (video), Mar. 14, 2011.
Epson US Newsroom, "Epson America Enters Sports Wearables Market with Introduction of M-Tracer MT500GII Golf Swing Analyzer", www.news.epson.com, Jan. 5, 2015, 4 pages.
International Search Report and Written Opinion dated Dec. 22, 2015 received in PCTUS1561695, 7 pages.
Search Report Received in PCT2013021999 dated Jan. 21, 2016.
Patent Examination Report received in Australia Application No. 2011313952, dated Mar. 15, 2016, 5 pages.
"About Banjo" webpages retrieved from internet, dated 2015.
International Search Report and Written Opinion mailed in PCTUS1642674 dated Aug. 12, 2016, 9 pages.
International Preliminary Report on Patentability in PCTUS2015061695, dated Jun. 1, 2017, 5 pages.
European Search Report received in PCTUS2015026896 dated May 11, 2017, 13 pages.
International Search Report and Written Opinion received in PCT/US2017/52114, dated Oct. 3, 9 pages.
International Search Report and Written Opinion Received in PCT/US2017/37987, dated Nov. 9, 2017, 12 pages.
Supplementary Extended European Search Report received in 11820763.8 dated Nov. 13, 2017, 16 pages.
Supplementary Extended European Search Report received in 11833159.4 dated Nov. 6, 2017, 14 pages.
Supplementary Partial European Search Report received from EP Application Serial No. 11820763.8, dated Aug. 8, 2017, 15 pages.
Supplementary Partial European Search Report received from EP Application Serial No. 11833159.4, dated Aug. 8, 2017, 15 pages.
Supplemental Search Report Received from EP Application Serial No. 16825295.5, dated Jun. 6, 2019, 7 pages.
David E. Culler, Et al., "Smart Sensors to Network the World", published in Scientific American Magazine, No. 06/2004, dated Jun. 1, 2004, pp. 85-91.
International Search Report and Written Opinion received in PCT/US2017/039209, dated Aug. 24, 2017, 7 pages.
*Zepp Labs, Inc.* v. *Blast Motion, Inc.* Petition for Inter Partes Review of U.S. Pat. No. 8,903,521 filed on Feb. 24, 2016, as IPR2016-00672, and accompanying Declaration of Dr. Steven M. Nesbit.
*Zepp Labs, Inc.* v. *Blast Motion, Inc.* Petition for Inter Partes Review of U.S. Pat. No. 9,039,527 filed on Feb. 24, 2016, as IPR2016-00674, and accompanying Declaration of Dr. Steven M. Nesbit.
*Zepp Labs, Inc.* v. *Blast Motion, Inc.* Petition for Inter Partes Review of U.S. Pat. No. 8,941,723 filed on Feb. 24, 2016, as IPR2016-00675, and accompanying Declaration of Dr. Steven M. Nesbit.
*Zepp Labs, Inc.* v. *Blast Motion, Inc.* Petition for Inter Partes Review of U.S. Pat. No. 8,905,855 filed on Feb. 24, 2016, as IPR2016-00676, and accompanying Declaration of Dr. Steven M. Nesbit.
*Zepp Labs, Inc.* v. *Blast Motion, Inc.* Petition for Inter Partes Review of U.S. Pat. No. 8,944,928 filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", www.electronicdesign.com/communications/wireless-sensor-architecture-uses-bluetooth-standard, Aug. 7, 2000, 5 pages.
Don Tuite, "Motion-Sensing MEMS Gyros and Accelerometers are Everywhere", www.electronicdesign.com/print/analog/motion-sensing-mems-gyros-and-accelerometers-are-everywhere, Jul. 9, 2009, 6 pages.
InvenSense News Release, "InvenSense Unveils World's $1^{st}$ IMU Solution for Consumer Applications", ir.invensense.com, 2016, 2 Pages.
Dean Takahashi, "Facebook, Twitter, Last.fm coming to Xbox Live this Fall", Jun. 1, 2009, Webpage printout, 5 pages.
The iClub System, Products pages, www.iclub.net, 2001-2005, 5 pages.
Websters New College Dictionary, Definition of "Virtual Reality", Third Edition, 2005, 3 Pages.
SmartSwing, "SmartSwing Introduces Affordable Intelligent Golf Club", www.smartswinggolf.com , Jan. 2006, 2 pages.
Henrick Arfwedson, et al., "Ericsson's Bluetooth modules", Ericsson Review No. 4, 1999, 8 pages.
ZigBees, "Zigbee information", www.zigbees.com , 2015, 4 pages.
SolidState Technology, "MEMS enable smart golf clubs", www.electroiq.com , 2005, 3 pages.
IGN, "Japanese WII Price Release Date Revealed", www.ign.com , 2006, 1 page.
First Annual Better Golf Through Technology Conference 2006 webpage, www.bettergolfthroughtechnology.com , Massachusetts Institute of Technology, Cambridge Massachusetts, Feb. 2006, 1 page.
Concept2Rowing, "Training" web content, www.concept2.com , 2009, 1 page.
Expresso, Products pages, www.expresso.com/products , 2009, 2 pages.

(56) References Cited

OTHER PUBLICATIONS

Manish Kalia, et al., "Efficient Policies for Increasing Capacity in Bluetooth: An Indoor Pico-Cellular Wireless System", IBM India Research Laboratory, Indian Institute of Technology, 2000, 5 pages.
R. Rao, et al., "Demand-Based Bluetooth Scheduling", Pennsylvania State University, 2001, 13 pages.
Supplementary Extended European Search Report received in 15782595.1 dated Nov. 27, 2017, 5 pages.
Supplementary European Search Report received in 15860384.5 dated Jun. 21, 2018, 9 pages.
International Search Report and Written Opinion received in PCT/US18033757, dated Aug. 31, 2018, 8 pages.
International Preliminary Report on Patentability received in PCT/US2017/037987, dated Dec. 27, 2018, 11 pages.
International Preliminary Report on Patentability received in PCT/US2018/033757, dated Dec. 5, 2019, 6 pages.
Extended European Search Report received in 17851741.3, dated Nov. 12, 2019, 8 pages.

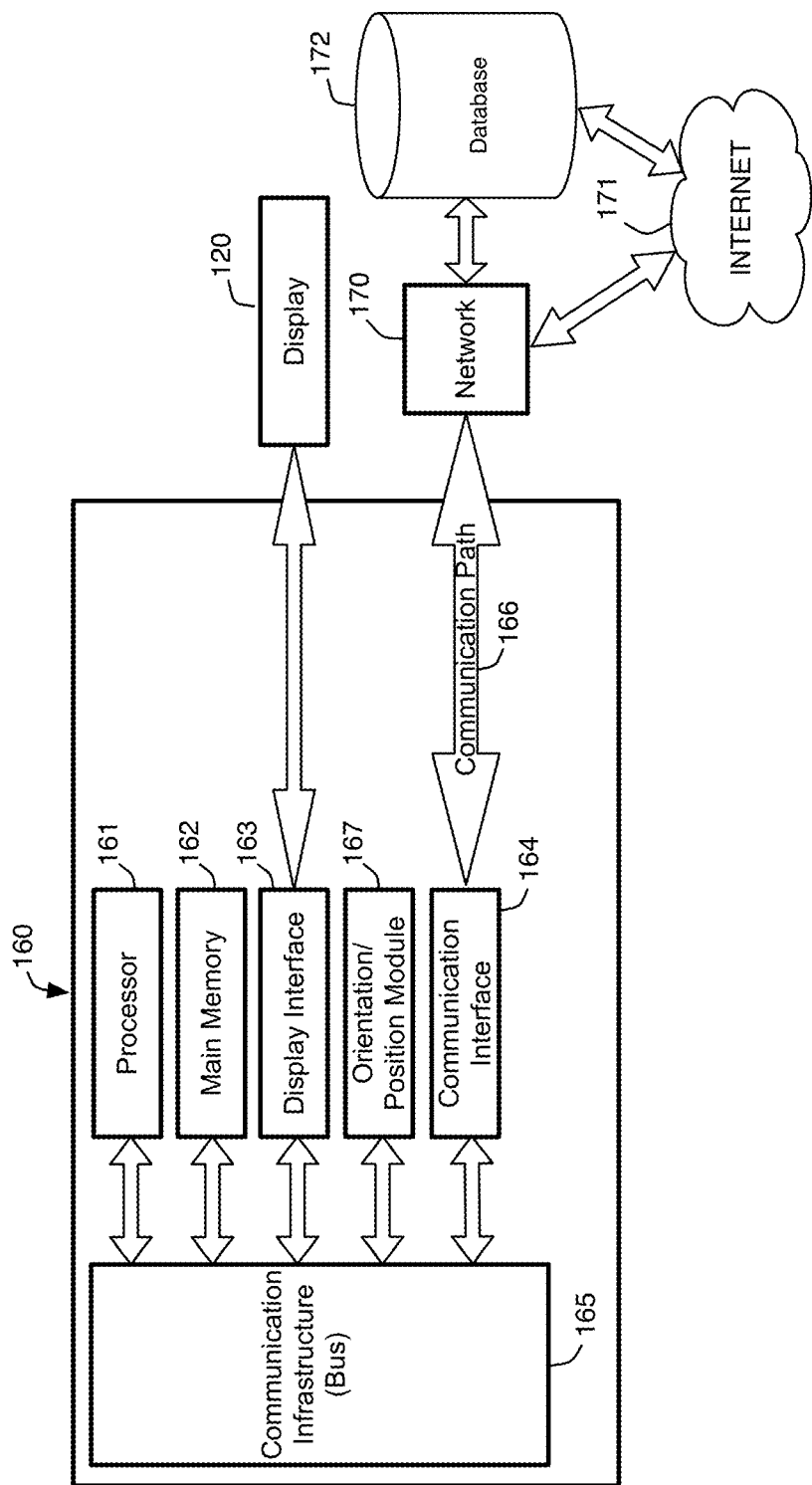

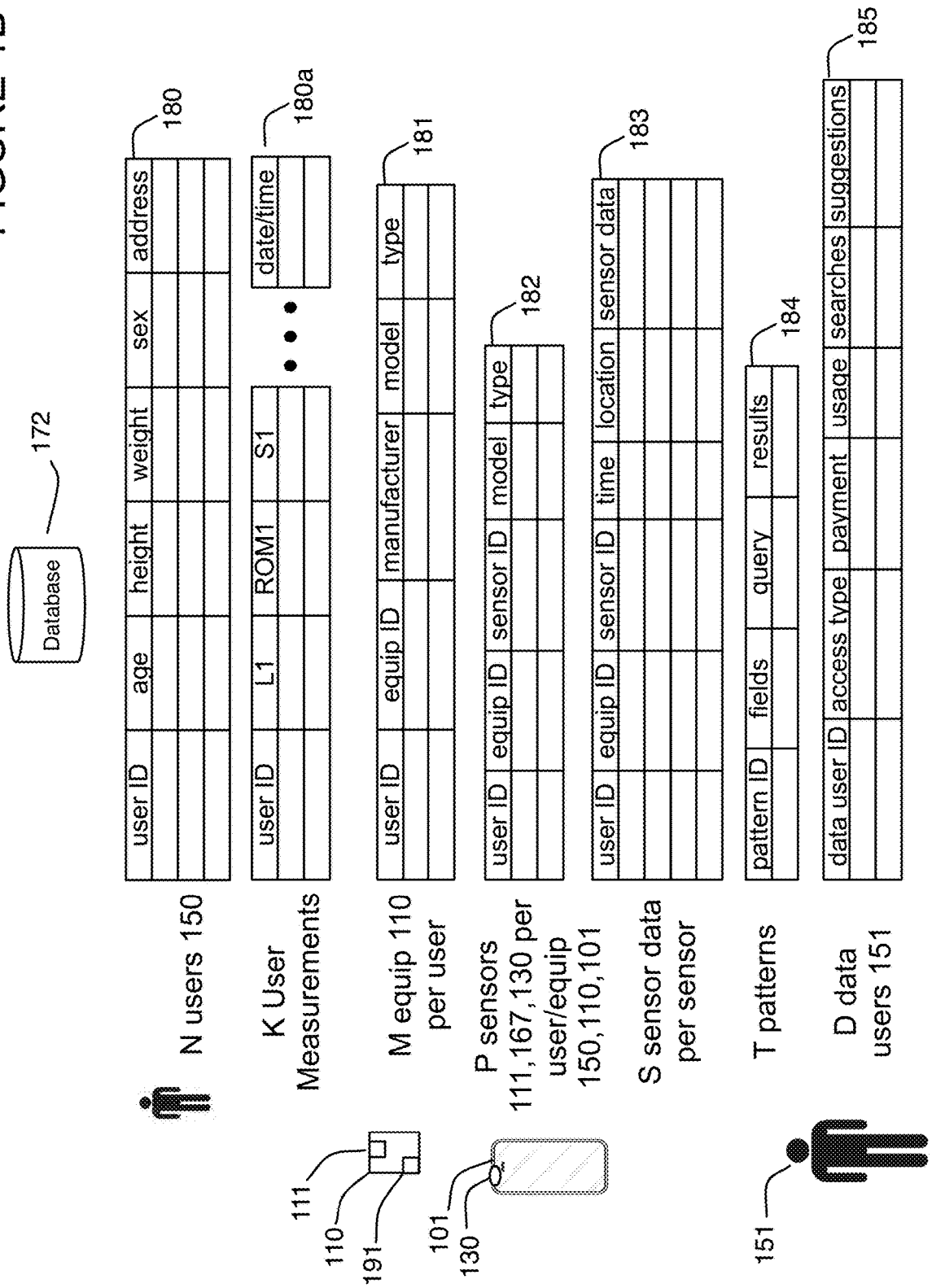

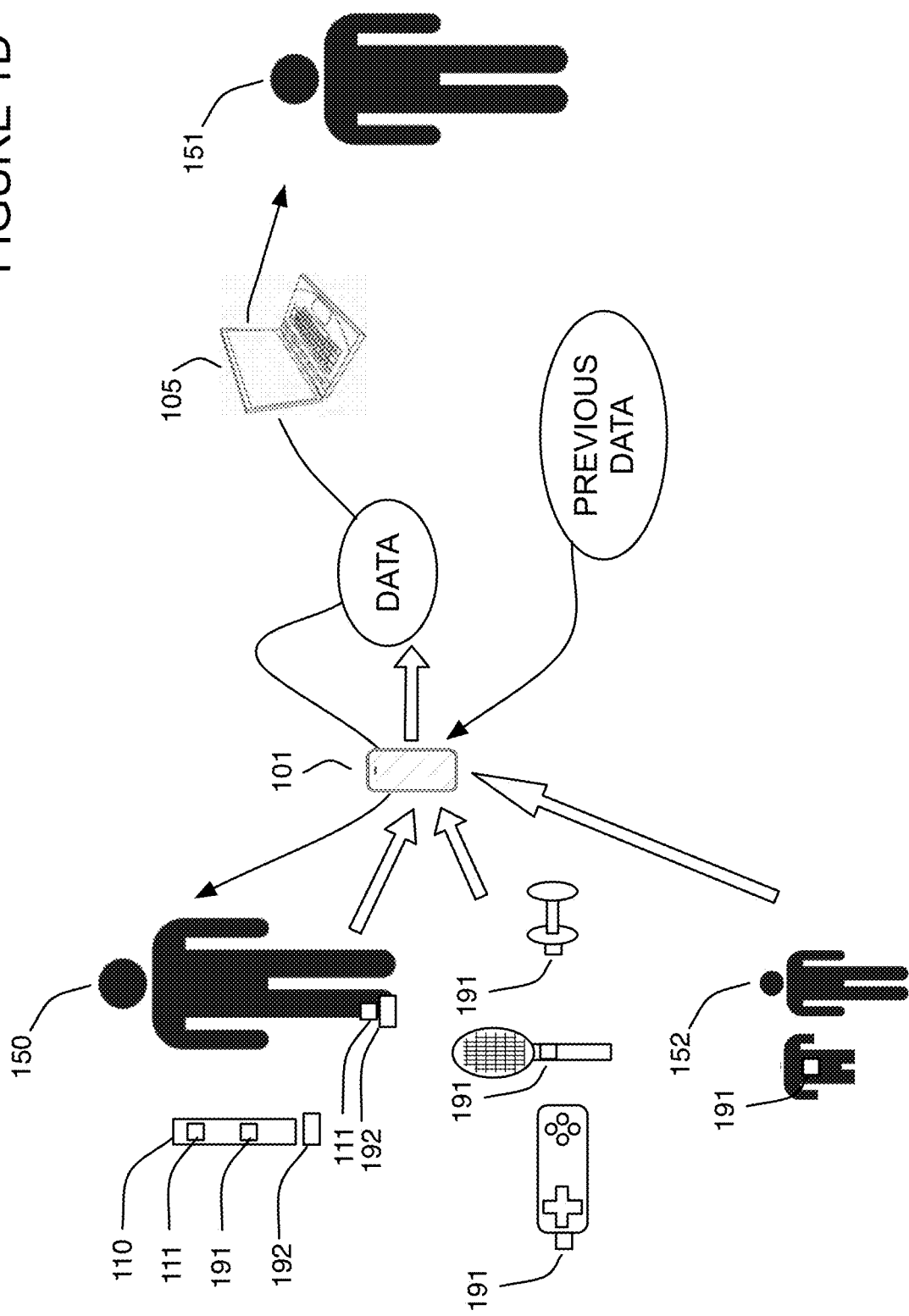

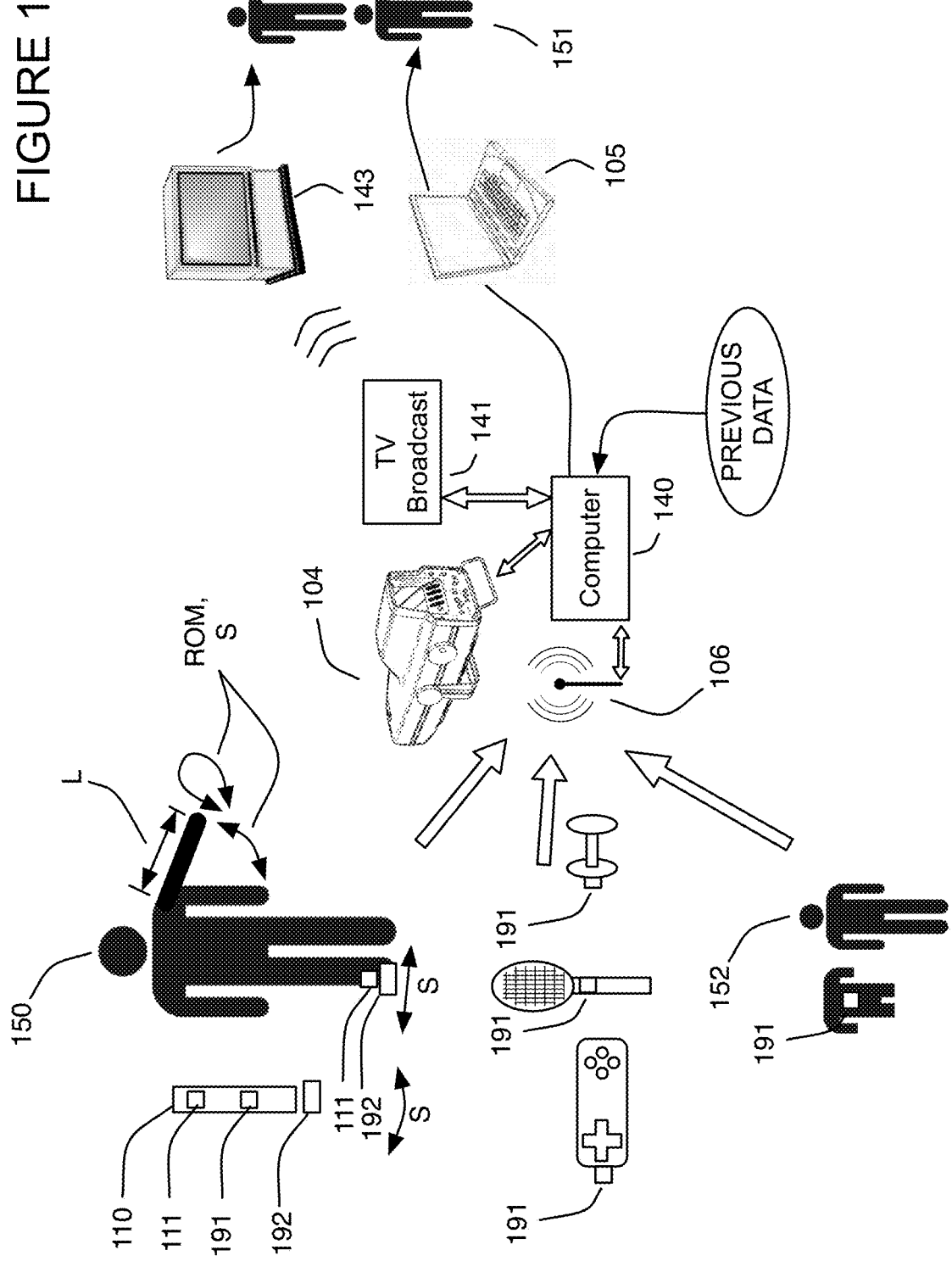

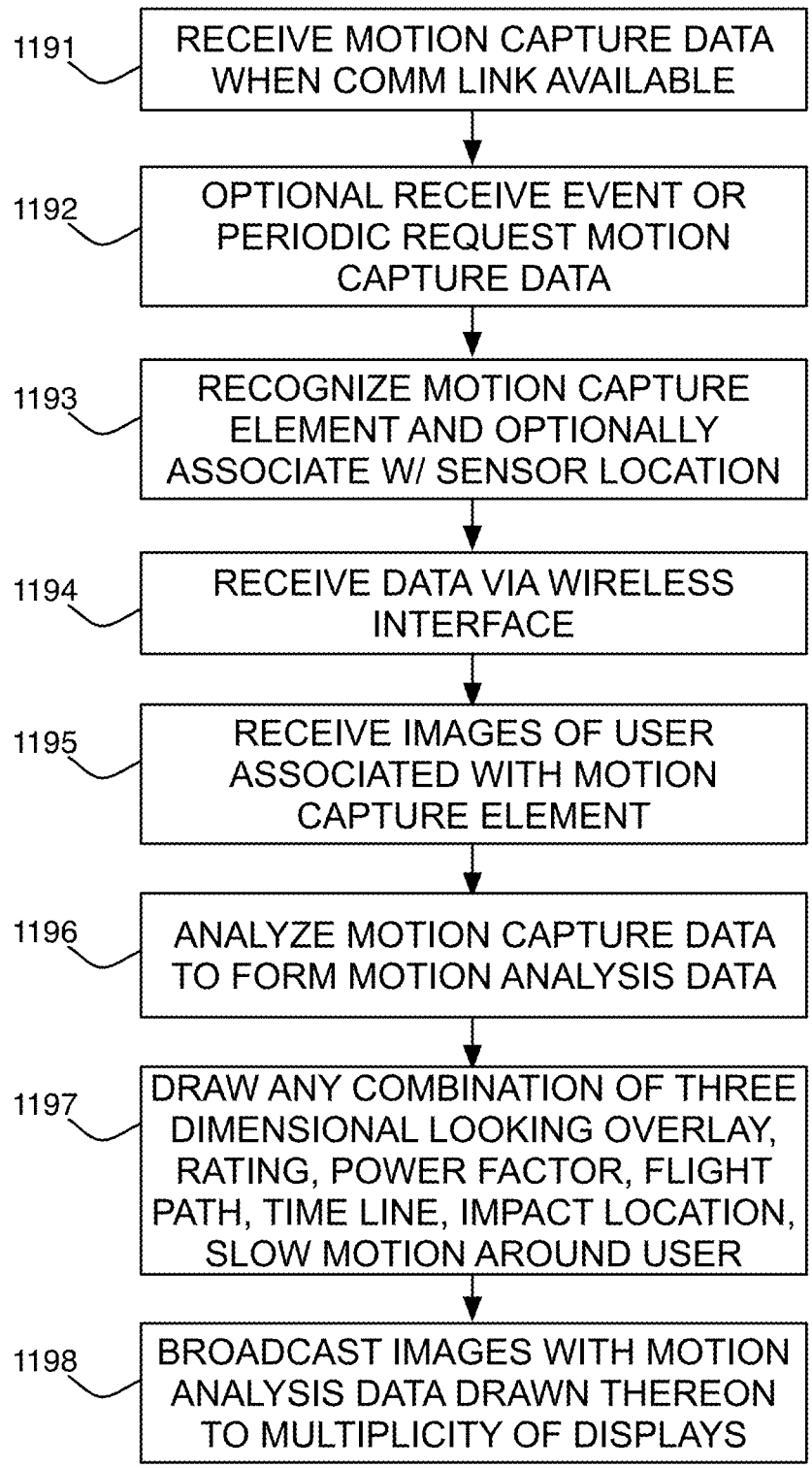

FIGURE 37

$$\ddot{x} = -Bu(C_D u_x + C_L u_y sin(\alpha))$$

$$\ddot{y} = -Bu[C_D u_y - C_L(u_x sin(\alpha) - u_z cos(\alpha))]$$

$$\ddot{z} = -g - Bu(C_D u_z - C_L u_y cos(\alpha))$$

$$C_D = \frac{46.0 ft/s}{v}$$

$$C_L = \frac{33.4 ft/s}{v}$$

3701

MOTION CAPTURE DATA FITTING SYSTEM

This application is a continuation of U.S. Utility patent application Ser. No. 15/812,926, filed on 14 Nov. 2017, issued as U.S. Pat. No. 10,350,455, which is a continuation of U.S. Utility patent application Ser. No. 15/044,036 filed 15 Feb. 2016, issued as U.S. Pat. No. 9,814,935, which is a continuation of U.S. Utility patent application Ser. No. 13/757,029 filed 1 Feb. 2013, issued as U.S. Pat. No. 9,261,526, which is a continuation-in-part of U.S. Utility patent application Ser. No. 13/737,956 filed 10 Jan. 2013, issued as U.S. Pat. No. 8,827,824, which is a continuation-in-part of U.S. Utility patent application Ser. No. 13/679,879 filed 16 Nov. 2012, issued as U.S. Pat. No. 8,944,928, which is a continuation-in-part of U.S. Utility patent application Ser. No. 13/298,158 filed 16 Nov. 2011, issued as U.S. Pat. No. 8,905,855, which is a continuation-in-part of U.S. Utility patent application Ser. No. 13/267,784 filed 6 Oct. 2011, issued as U.S. Pat. No. 9,604,142, which is a continuation-in-part of U.S. Utility patent application Ser. No. 13/219,525 filed 26 Aug. 2011, issued as U.S. Pat. No. 8,941,723, which is a continuation-in-part of U.S. Utility patent application Ser. No. 13/191,309 filed 26 Jul. 2011, issued as U.S. Pat. No. 9,033,810, which is a continuation-in-part of U.S. Utility patent application Ser. No. 13/048,850 filed 15 Mar. 2011, issued as U.S. Pat. No. 8,465,376, which is a continuation-in-part of U.S. Utility patent application Ser. No. 12/901,806 filed 11 Oct. 2010, issued as U.S. Pat. No. 9,320,957, which is a continuation-in-part of U.S. Utility patent application Ser. No. 12/868,882 filed 26 Aug. 2010, issued as U.S. Pat. No. 8,944,826, the specifications of which are hereby incorporated herein by reference.

BACKGROUND OF THE INVENTION

Field of the Invention

One or more embodiments setting forth the ideas described throughout this disclosure pertain to the field of sporting equipment fitting. One or more embodiments present information associated with an optimally fitting piece of sporting equipment, for example the best performing piece of equipment associated with a group of second users within a range or correlation of size, range of motion or speed or any combination thereof, with respect to the user. For example, embodiments may present information related to a particular make, model, dimension, weight, length, stiffness, or other parameter associated with a piece of sporting equipment through use of a motion capture sensor to measure a user's various dimensions or sizes, range of motion and speed and/or acceleration for example. Embodiments for example prompt for and accept movement to determine distance and/or speed between two locations and/or through a rotation. For example embodiments may be utilized to determine height, arm length, wrist to floor distance, hand size, longest finger size, arm length, leg length torso length, range of motion, such as but not limited to flexion, extension, abduction, adduction, outward rotation, inward rotation, pronation, supination, inversion and eversion, and speed through any motion or rotation. The distance, range of motion and speed may be obtained for any limb or through motion of any joint or portion of the human body for example. Embodiments may further utilize the same sensor for example after coupling the sensor to the piece of equipment, to obtain motion capture data from the piece of equipment, such as speed of the equipment when moved through a typical type of motion for the piece of equipment, for example to further optimize the fit. The fit may be optimized by data mining or otherwise through calculation of a correlation of dimensions, range of motion, for example static-active, static-passive and/or dynamic/kinetic range of motion, speed/acceleration, etc., with various other users, whether alive or historical as calculated through visual or other methods. Embodiments thus determine the best performing equipment for that particular type of user, i.e., within a range of size, range of motion, speed, for example the make/model of the longest hitting, most accurate, maximum or minimum scoring, etc., as previously obtained and/or determined from or based on other users having the closest dimensions, range of motion and speed. Embodiments also enable purchasing of the equipment via the mobile device, whether the piece of equipment is shown on television or other broadcast or based on the user's previous performance data or current performance data. Embodiments may further be configured to predict a first derivative or other derivate based on age or growth rates to determine the best fitting equipment for children that will fit for the longest time or otherwise minimize costs and maximize usage of equipment as well. Other embodiments of the invention may suggest exercises and/or stretches that would improve performance to a predicted performance level based on other users performance data and suggest equipment that would be appropriate for an increase strength or flexibility so that users can "grow into" or "improve into" equipment. In addition, other embodiments of the invention may be utilized over time to detect tight areas or areas that may be indicative of injury for example and alert the user. One or more embodiments of the invention may be utilized for gait analysis for fitting of shoes.

Description of the Related Art

There are no known systems that use a given motion capture sensor to measure a user's size, range of motion, speed and then utilize that same sensor to capture motion data from a piece of sporting equipment, for example to further optimize the fit of a particular piece of sporting equipment or to gather performance data over time from the same sensor. Existing sporting equipment fitting systems are generally based on size measurements of a user. These systems generally do not take into account the range of motion or direct measurements of speed through the range of motion of various joints of a user to optimize a fit for a piece of sporting equipment. There are no known fitting systems based on motion capture data obtained from high resolution sensors, for example that include use of previously stored high resolution motion data from the user or other users or piece of equipment, or from motion capture data obtained through the analysis of historical videos for example. Known systems do not contemplate data mining of motion data and size, range of motion, speed and age of other users to maximize the performance of the user.

In addition, known systems do not provide a sensor and "app" that may be inexpensively obtained and utilized on a ubiquitous mobile device such as a mobile telephone to prompt for and obtain distance, dimensions, range of motion, speed or other measurement data and suggest optimal equipment and enable the user to immediately purchase the optimally fitting equipment from the same mobile device.

Specifically, most motion capture systems are generally utilized to observe and/or teach effective body mechanics and utilize video recording of an athlete and analysis of the recorded video of an athlete. This technique has various limitations including inaccurate and inconsistent subjective analysis based on video for example. Another technique includes motion analysis, for example using at least two cameras to capture three-dimensional points of movement associated with an athlete. Known implementations utilize a stationary multi-camera system that is not portable and thus cannot be utilized outside of the environment where the system is installed, for example during an athletic event such as a golf tournament. These fixed installations are extremely expensive as well. Such prior techniques are summarized in U.S. Pat. No. 7,264,554, filed 26 Jan. 2006, which claims the benefit of U.S. Provisional Patent Application Ser. No. 60/647,751 filed 26 Jan. 2005, the specifications of which are both hereby incorporated herein by reference. Both disclosures are to the same inventor of the subject matter of the instant application. Regardless of the motion capture data obtained, the data is generally analyzed on a per user or per swing basis that does not contemplate processing on a mobile phone, so that a user would only buy a motion capture sensor and an "app" for a pre-existing mobile phone. In addition, existing solutions do not contemplate mobile use, analysis and messaging and/or comparison to or use of previously stored motion capture data from the user or other users or data mining of large data sets of motion capture data, for example to obtain or create motion capture data associated with a group of users, for example professional golfers, tennis players, baseball players or players of any other sport to provide a "professional level" average or exceptional virtual reality opponent. To summarize, motion capture data is generally used for immediate monitoring or sports performance feedback and generally has had limited and/or primitive use in other fields. Any uses for the data with respect to fitting are limited, and generally based on the size of the user and do not utilize a given sensor to measure the user's size, range of motion and speed as well as the motion of the piece of equipment, for example after coupling the motion capture sensor to the piece of equipment after the uncoupled sensor is utilized in measuring physical parameters of the user without the piece of equipment.

Known motion capture systems generally utilize several passive or active markers or several sensors. There are no known systems that utilize as little as one visual marker or sensor and an app that for example executes on a mobile device that a user already owns, to analyze and display motion capture data associated with a user and/or piece of equipment. The data is generally analyzed in a laboratory on a per user or per swing basis and is not used for any other purpose besides motion analysis or representation of motion of that particular user and is generally not subjected to data mining. This also makes fitting for sporting equipment more difficult for the user, since the user must travel to a particular installation for custom fitting for example.

There are no known systems that allow for motion capture elements such as wireless sensors to seamlessly integrate or otherwise couple with a user or shoes, gloves, shirts, pants, belts, or other equipment, such as a baseball bat, tennis racquet or golf club for local analysis or later analysis in such a small format that the user is not aware that the sensors are located in or on these items. There are no known systems that provide seamless mounts, for example in the weight port of a golf club or at the end shaft near the handle so as to provide a wireless golf club, configured to capture motion data. Data derived from existing sensors is not saved in a database for a large number of events and is not used relative to anything but the performance at which the motion capture data was acquired. In addition, known motion capture sensors are specifically designed to mount to a piece of sporting equipment in a particular manner and are not intended to measure the user's size, range of motion or speed for example without being mounted on the piece of sporting equipment.

In addition, for sports that utilize a piece of equipment and a ball, there are no known portable systems that allow the user to obtain immediate visual feedback regarding ball flight distance, swing speed, swing efficiency of the piece of equipment or how centered an impact of the ball is, i.e., where on piece of equipment the collision of the ball has taken place. These systems do not allow for user's to play games with the motion capture data acquired from other users, or historical players, or from their own previous performances. Known systems do not allow for data mining motion capture data from a large number of swings to suggest or allow the searching for better or optimal equipment to match a user's motion capture data and do not enable original equipment manufacturers (OEMs) to make business decisions, e.g., improve their products, compare their products to other manufacturers, up-sell products or contact users that may purchase different or more profitable products.

In addition, there are no known systems that utilize motion capture data mining for equipment fitting and subsequent point-of-sale decision making for instantaneous purchasing of equipment that fits an athlete. Furthermore, no known systems allow for custom order fulfillment such as assemble-to-order (ATO) for custom order fulfillment of sporting equipment, for example equipment that is built to customer specifications based on motion capture data mining, and shipped to the customer to complete the point of sales process, for example during play or virtual reality play or for example during a television broadcast.

There are no known systems that enable data mining for a large number of users related to their motion or motion of associated equipment to find patterns in the data that allows for business strategies to be determined based on heretofore undiscovered patterns related to motion. There are no known systems that enable obtain payment from OEMs, medical professionals, gaming companies or other end users to allow data mining of motion data. For at least the limitations described above there is a need for a fitting system for sporting equipment that utilizes an motion capture sensor, for example uncoupled from the piece of sporting equipment to measure a user's size, range of motion and speed and optimize a fit for a piece of sporting equipment after coupling the motion capture sensor to the piece of sporting equipment and deriving an optimized fit based on current and/or previously stored or calculated motion data from the same user or other user's that maximally correlate with the user's size, range of motion, speed or any other parameters such as age.

BRIEF SUMMARY OF THE INVENTION

Embodiments of the invention enable a fitting system for sporting equipment using an application that executes on a mobile device, for example a mobile phone, to prompt and accept motion inputs from a given motion capture sensor to measure a user's size, range of motion, speed and/or acceleration and then in one or more embodiments utilizes that same sensor to capture motion data from a piece of equipment, for example to further optimize the fit of and/or further collect motion capture data. Embodiments may provide information related to the optimal fit or otherwise suggest purchase of a particular piece of sporting equipment.

Embodiments may utilize correlation or other algorithms or data mining of motion data for size, range of motion, speed of other users to maximize the fit of a piece of equipment for the user based on other user's performance with particular equipment. For example, this enables a user of a similar size, range of motion and speed to data mine for the best performance equipment, e.g., longest drive, lowest putt scores, highest winning percentage, etc., associated with other users having similar characteristics.

Specifically, one or more embodiments of the fitting system for sporting equipment include at least one motion capture element that includes a wireless communication interface configured to transmit motion capture data from the at least one motion capture element and an application configured to execute on a computer within a mobile device that is configured to wirelessly communicate with the motion capture sensor, and optionally configured to telephonically communicate. In one or more embodiments the application is configured to prompt a first user to move the motion capture sensor to a first location, accept a first motion capture data from the motion capture sensor at the first location via the wireless communication interface, prompt the first user to move the motion capture sensor to a second location, accept a second motion capture data or rotation from the motion capture sensor at the second location via the wireless communication interface, calculate a distance or rotation between the first and second location or rotation based on the first and second motion capture data. The distance may include a height or an arm length, or a torso length, or a leg length, or a wrist to floor measurement, or a hand size or longest finger size or both the hand size and longest finger size of the first user, or any combination thereof or any other dimension or length associated with the first user. For example, embodiments of the invention may prompt the user to hold the motion capture sensor in the user's hand and hold the hand on top of the user's head and then prompt the user to place the sensor on the ground, to calculate the distance therebetween, i.e., the height of the user. In another example, the system may prompt the user to hold the sensor in the hand, for example after decoupling the sensor from a golf club and then prompt the user to place the sensor on the ground. The system then calculates the distance as the "wrist to floor measurement", which is commonly used in sizing golf clubs for example. Embodiments of the system may also prompt the user to move the sensor from the side of the user to various positions or rotational values, for example to rotate the sensor while at or through various positions to calculate the range of motion, for example through flexion, extension, abduction, adduction, lateral rotation, medial rotation, etc. The range of motion may be detected for different types of stretching or movement such as static-active, static-passive and/or dynamic/kinetic stretching or rotation of any desired joint or body part. In one or more embodiments, the application is further configured to prompt the first user to couple the motion capture sensor to a piece of equipment and prompt the first user to move the piece of equipment through a movement. The application is further configured to accept a third motion capture data from the motion capture sensor for the movement via the wireless communication interface and calculate a speed for the movement based on the third motion capture data. In one or more embodiments, the application is configured to calculate a correlation between the distance and the speed for the first user with respect to a plurality of other users and present information associated with an optimally fit or sized piece of equipment associated with a second user having a maximum value correlation with at least the distance and the speed of the first user. One such algorithm may for example provide a list of make and model of the lowest scoring golf shaft, or longest hitting baseball bat associated with a similar size/range of motion/speed user. Embodiments of the user may use the speed of the user through motions or the speed of the equipment through motions or both in correlation calculations for example. Embodiments may further be configured to predict a first derivative or other derivate based on age or growth rates to determine the best fitting equipment for children that will fit for the longest time or otherwise minimize costs and maximize usage of equipment as well. Other embodiments of the invention may suggest exercises and/or stretches that would improve performance to a predicted performance level based on other users performance data and suggest equipment that would be appropriate for an increase strength or flexibility so that users can "grow into" or "improve into" equipment. In addition, other embodiments of the invention may be utilized over time to detect tight areas or areas that may be indicative of injury for example and alert the user. One or more embodiments of the invention may be utilized for gait analysis for fitting of shoes.

Other embodiments may display one or more images to enable the first user to view a sporting event. Embodiments may accept an input from the first user to purchase the piece of equipment based the distance, or range of motion or the speed previously stored with respect to the first user or any combination thereof. For example, the piece of equipment may be shown in the sporting event, but sized to fit the user based on the user's previously stored or currently accepted or calculated parameters. Embodiments may also prompt the first user for their age and utilize this when calculation of the correlation is performed. Embodiments may present information associated with a grip or length of the optimally sized piece of equipment, or stiffness, or model or manufacturer, or any combination thereof.

Embodiments of the application may also be configured to recognize when the at least one motion capture element is removed from the piece of equipment based on the motion capture data. The application may for example accept gestures or analyze the motion to determine that it could not be output from a particular piece of equipment based on the motion. Alternatively, or in combination, embodiments of the invention may recognize when the at least one motion capture element is coupled with the piece of equipment based on the motion capture data. For example if the motion data is analyzed and is determined to have a path of motion indicative of a baseball bat swing or golf swing then, the system may indicate that the motion capture sensor is currently coupled to the piece of equipment. Furthermore, since different pieces of equipment may utilize the same sensor, for example after decoupling from one and placing in the other, particular types of motion, for example a skate board and a tennis racquet may be automatically determined based on a barrel roll of the skateboard or serve of the racquet which indicates the path of motion that is unique or at least indicative of that type of equipment. This enables automatic sensing of the piece of equipment currently coupled with the sensor.

Embodiments of the invention may utilize data mining on the motion capture data to obtain patterns for users, equipment, or use the motion capture data of a given user or other user in particular embodiments of the invention. Data mining relates to discovering new patterns in large databases wherein the patterns are previously unknown. Many methods may be applied to the data to discover new patterns including statistical analysis, neural networks and artificial intelligence for example. Due to the large amount of data, automated data mining may be performed by one or more computers to find unknown patterns in the data. Unknown patterns may include groups of related data, anomalies in the data, dependencies between elements of the data, classifications and functions that model the data with minimal error or any other type of unknown pattern. Displays of data mining results may include displays that summarize newly discovered patterns in a way that is easier for a user to understand than large amounts of pure raw data. One of the results of the data mining process is improved market research reports, product improvement, lead generation and targeted sales. Generally, any type of data that will be subjected to data mining must be cleansed, data mined and the results of which are generally validated. Businesses may increase profits using data mining. Examples of benefits of embodiments of the invention include customer relationship management to highly target individuals based on patterns discovered in the data. In addition, market basket analysis data mining enables identifying products that are purchased or owned by the same individuals and which can be utilized to offer products to users that own one product but who do not own another product that is typically owned by other users. Other areas of data mining include analyzing large sets of motion data from different users to suggest exercises to improve performance based on performance data from other users. For example if one user has less rotation of the hips during a swing versus the average user, then exercises to improve flexibility or strength may be suggested by the system. In a golf course embodiment, golf course planners may determine over a large amount of users on a golf course which holes should be adjusted in length or difficulty to obtain more discrete values for the average number of shots per hole, or for determining the amount of time between golfers, for example at a certain time of day or for golfers of a certain age. In addition, sports and medical applications of data mining include determining morphological changes in user performance over time, for example versus diet or exercise changes to determine what improves performance the most.

For example, embodiments that utilize motion capture elements allow for analyzing the data obtained from the apparatus and enable the presentation of unique displays associated with the user, such as 3D overlays onto images of the body of the user to visually depict the captured motion data. In addition, these embodiments may also utilize active wireless technology such as BLUETOOTH® Low Energy for a range of up to 50 meters to communicate with a golfer's mobile computer. Embodiments of the invention also allow for display of queries for counting a stroke for example as a result of receiving a golf club ID, for example via an RFID reader or alternatively via wireless communication using BLUETOOTH® or IEEE 802.11 for example. Use of BLUETOOTH® Low Energy chips allows for a club to be in sleep mode for up to 3 years with a standard coin cell battery, thus reducing required maintenance. One or more embodiments of the invention may utilize more than one radio, of more than one technology for example. This allows for a level of redundancy that increases robustness of the system. For example, if one radio no longer functions, e.g., the BLUETOOTH® radio for example, then the IEEE 802.11 radio may be utilized to transfer data and warn the golfer that one of the radios is not functioning, while still allowing the golfer to record motion data and count shots associated with the particular club. For embodiments of the invention that utilize a mobile device (or more than one mobile device) without camera(s), sensor data may be utilized to generate displays of the captured motion data, while the mobile device may optionally obtain images from other cameras or other mobile devices with cameras. For example, display types that may or may not utilize images of the user may include ratings, calculated data and time line data. Ratings associated with the captured motion can also be displayed to the user in the form of numerical or graphical data with or without a user image, for example an "efficiency" rating. Calculated data, such as a predicted ball flight path data can be calculated and displayed on the mobile device with or without utilizing images of the user's body. Data depicted on a time line can also be displayed with or without images of the user to show the relative peaks of velocity for various parts of the equipment or user's body for example. Any of these types of measurements that are for example associated with speed are in keeping with the fitting aspects of the invention, and the use of speed herein may include any derived quantity associated with motion for example when used in conjunction with fitting of equipment with a particular user.

In one or more embodiments of the invention, fixed cameras such as at a tennis tournament, football game, baseball game, car or motorcycle race, golf tournament or other sporting event can be utilized with a wireless interface located near the player/equipment having motion capture elements so as to obtain, analyze and display motion capture data. In this embodiment, real-time or near real-time motion data can be displayed on the video for augmented video replays. An increase in the entertainment level is thus created by visually displaying how fast equipment is moving during a shot, for example with rings drawn around a players hips and shoulders. Embodiments of the invention also allow images or videos from other players having mobile devices to be utilized on a mobile device related to another user so that users don't have to switch mobile phones for example. In one embodiment, a video obtained by a first user for a piece of sporting equipment in motion that is not associated with the second user having the video camera equipped mobile phone may automatically transfer the video to the first user for display with motion capture data associated with the first user. Video and images may be uploaded into the database and data mined through image analysis to determine the types/colors of clothing or shoes for example that users are wearing. The equipment thus analyzed or otherwise input into the system may be broadcast so that other embodiments of the invention may be utilized to purchase the equipment, for example as sized to the user, or sized to the user to maximize performance as correlated with other users for example.

Based on the display of data, the user can determine the equipment that fits the best and immediately purchase the equipment, via the mobile device. For example, when deciding between two sets of skis, a user may try out both pairs that are instrumented with motion capture elements wherein the motion capture data is analyzed to determine which pair of skis enables more efficient movement. For golf embodiments, when deciding between two golf clubs, a user can take swings with different clubs and based on the analysis of the captured motion data and quantitatively determine which club performs better, for example in conjunction with size, range of motion or speed of the user or any combination thereof as determined using a motion capture sensor alone and/or in combination with a piece of equipment. Custom equipment may be ordered through an interface on the mobile device from a vendor that can assemble-to-order customer built equipment and ship the equipment to the user for example. Shaft lengths for putters for example that are a standard length can be custom made for a particular user based on captured motion data as a user putts with an adjustable length shaft for example. Based on data mining of the motion capture data and shot count data and distances for example allows for users having similar swing characteristics to be compared against a current user wherein equipment that delivers longer shots for a given swing velocity for a user of a particular size and age for example may be suggested or searched for by the user to improve performance. OEMs may determine that for given swing speeds, which make and model of club delivers the best overall performance as well. One skilled in the art will recognize that this applies to all activities involving motion, not just golf.

Embodiments of the system may utilize a variety of sensor types. In one or more embodiments of the invention, active sensors may integrate with a system that permits passive or active visual markers to be utilized to capture motion of particular points on a user's body or equipment. This may be performed in a simply two-dimensional manner or in a three-dimensional manner if the mobile device is configured with two or more cameras, or if multiple cameras or mobile devices are utilized to capture images such as video and share the images in order to create triangulated three-dimensional motion data from a set of two-dimensional images obtained from each camera. Another embodiment of the invention may utilize inertial measurement units (IMU) or any other sensors that can produce any combination of orientation, position, velocity and/or acceleration information to the mobile device. The sensors may thus obtain data that may include any combination of one or more values associated with orientation (vertical or North/South or both), position (either via through Global Positioning System, i.e., "GPS" or through triangulation), velocity (in all three axes), acceleration (in all three axes). All motion capture data obtained from the various sensor types may be saved in a database for analysis, monitoring, compliance, game playing or other use and/or data mining, regardless of the sensor type.

In one or more embodiments of the invention, a sensor may be utilized that includes a passive marker or active marker on an outside surface of the sensor, so that the sensor may also be utilized for visual tracking (either two-dimensional or three-dimensional) and for orientation, position, velocity, acceleration or any other physical quantity produced by the sensor. Visual marker embodiments of the motion capture element(s) may be passive or active, meaning that they may either have a visual portion that is visually trackable or may include a light-emitting element such as a light emitting diode (LED) that allows for image tracking in low light conditions. This for example may be implemented with a graphical symbol or colored marker at the end of the shaft near the handle or at the opposing end of the golf club at the head of the club. Images or videos of the markers may be analyzed locally or saved in the database and analyzed and then utilized in data mining.

Embodiments of the motion capture sensors may be generally mounted on or near one or more end or opposing ends of sporting equipment, for example such as a golf club and/or anywhere in between (for EI measurements) and may integrate with other sensors coupled to equipment, such as weapons, medical equipment, wristbands, shoes, pants, shirts, gloves, clubs, bats, racquets, balls, etc., and/or may be attached to a user in any possible manner. For example, a rifle to determine where the rifle was pointing when recoil was detected by the motion capture sensor. This data may be transmitted to a central server, for example using a mobile computer such as a mobile phone or other device and analyzed for war games practice for example. In addition, one or more embodiments of the sensor can fit into a weight port of a golf club, and/or in the handle end of the golf club. Other embodiments may fit into the handle of, or end of, a tennis racquet or baseball bat for example. One or more embodiments of the invention may also operate with balls that have integrated sensors as well. One or more embodiments of the mobile device may include a small mountable computer such as an IPOD® SHUFFLE® or IPOD® NANO® that may or may not have integrated displays, and which are small enough to mount on a shaft of a piece of sporting equipment and not affect a user's swing. Alternatively, the system may calculate the virtual flight path of a ball that has come in contact with equipment moved by a player. For example with a baseball bat or tennis racquet or golf club having a sensor integrated into a weight port of other portion of the end of the club striking the golf ball and having a second sensor located in the tip of the handle of the golf club, or in one or more gloves worn by the player, an angle of impact can be calculated for the club. By knowing the loft of the face of the club, an angle of flight may be calculated for the golf ball. In addition, by sampling the sensor at the end of the club at a high enough speed to determine oscillations indicative of where on the face of the club the golf ball was struck, a quality of impact may be determined. These types of measurements and the analysis thereof help an athlete improve, and for fitting purposes, allow an athlete to immediately purchase equipment that fits correctly. Centering data may be uploaded to the database and data mined for patterns related to the bats, racquets or clubs with the best centering on average, or the lowest torsion values for example on a manufacturer basis for product improvement. Any other unknown patterns in the data that are discovered may also be presented or suggested to users or search on by users, or paid for, for example by manufacturers or users.

One or more embodiments of the motion capture sensor may be removed from one piece of sporting equipment and placed on another type of equipment or article of clothing so that the user does not have to purchase motion capture sensors for all equipment and clothes associated with the user. This is possible since embodiments of the sensor may couple with any enclosure sized to fit the sensor. In one or more embodiments, a cap is removed, then the sensor is removed and inserted into another piece of equipment or article of clothing for example.

One or more embodiments of the sensor may contain charging features such as mechanical eccentric weight, as utilized in some watches known as "automatic" or "self-winding" watches, optionally including a small generator, or inductive charging coils for indirect electromechanical charging of the sensor power supply. Other embodiments may utilize plugs for direct charging of the sensor power supply or electromechanical or microelectromechanical (MEMS) based charging elements. Any other type of power micro-harvesting technologies may be utilized in one or more embodiments of the invention. One or more embodiments of the sensor may utilize power saving features including gestures that power the sensor on or off. Such gestures may include motion, physical switches, contact with the sensor, wireless commands to the sensor, for example from a mobile device that is associated with the particular sensors. Other elements that may couple with the sensor includes a battery, low power microcontroller, antenna and radio, heat sync, recharger and overcharge sensor for example. In addition, embodiments of the invention allow for power down of some or all of the components of the system until an electronic signal from accelerometers or a mechanical switch determines that the club has moved for example.

One or more embodiments of the invention enable Elasticity Inertia or EI measurement of sporting equipment and even body parts for example. Placement of embodiments of the sensor along the shaft of a golf club, tennis racquet, baseball bat, hockey stick, shoe, human arm or any other item that is not perfectly stiff enables measurement of the amount of flex at points where sensors are located or between sensors. The angular differences in the each sensor over time allow for not only calculation of a flex profile, but also a flex profile that is dependent on time or force. For example, known EI machines use static weights between to support points to determine an EI profile. These machines therefore cannot detect whether the EI profile is dependent upon the force applied or is dependent on the time at which the force is applied, for example EI profiles may be non-linear with respect to force or time. Example materials that are known to have different physical properties with respect to time include Maxwell materials and non-Newtonian fluids.

A user may also view the captured motion data in a graphical form on the display of the mobile device or for example on a set of glasses that contains a video display. The captured motion data obtained from embodiments of the motion capture element may also be utilized to augment a virtual reality display of user in a virtual environment. Virtual reality or augmented reality views of patterns that are found in the database via data mining are also in keeping with the spirit of the invention. User's may also see augmented information such as an aim assist or aim guide that shows for example where a shot should be attempted to be placed for example based on existing wind conditions, or to account for hazards, e.g., trees that are in the way of a desired destination for a ball, i.e., the golf hole for example.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The above and other aspects, features and advantages of the ideas conveyed through this disclosure will be more apparent from the following more particular description thereof, presented in conjunction with the following drawings wherein:

FIG. 1A illustrates a logical hardware block diagram of an embodiment of the computer.

FIG. 1B illustrates an architectural view of an embodiment of the database utilized in embodiments of the system.

FIG. 1D illustrates a data flow diagram for an embodiment of the system.

FIG. 1E illustrates a data flow diagram for an embodiment of the system, including broadcasting components.

FIG. 1F illustrates a flow chart for an embodiment of the system for intermittent data broadcast scenarios.

FIG. 37 illustrates an embodiment of the equation used to calculate the accelerations in the x, y and z axes.

DETAILED DESCRIPTION OF THE INVENTION

A fitting system for sporting equipment will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

Figure 1:
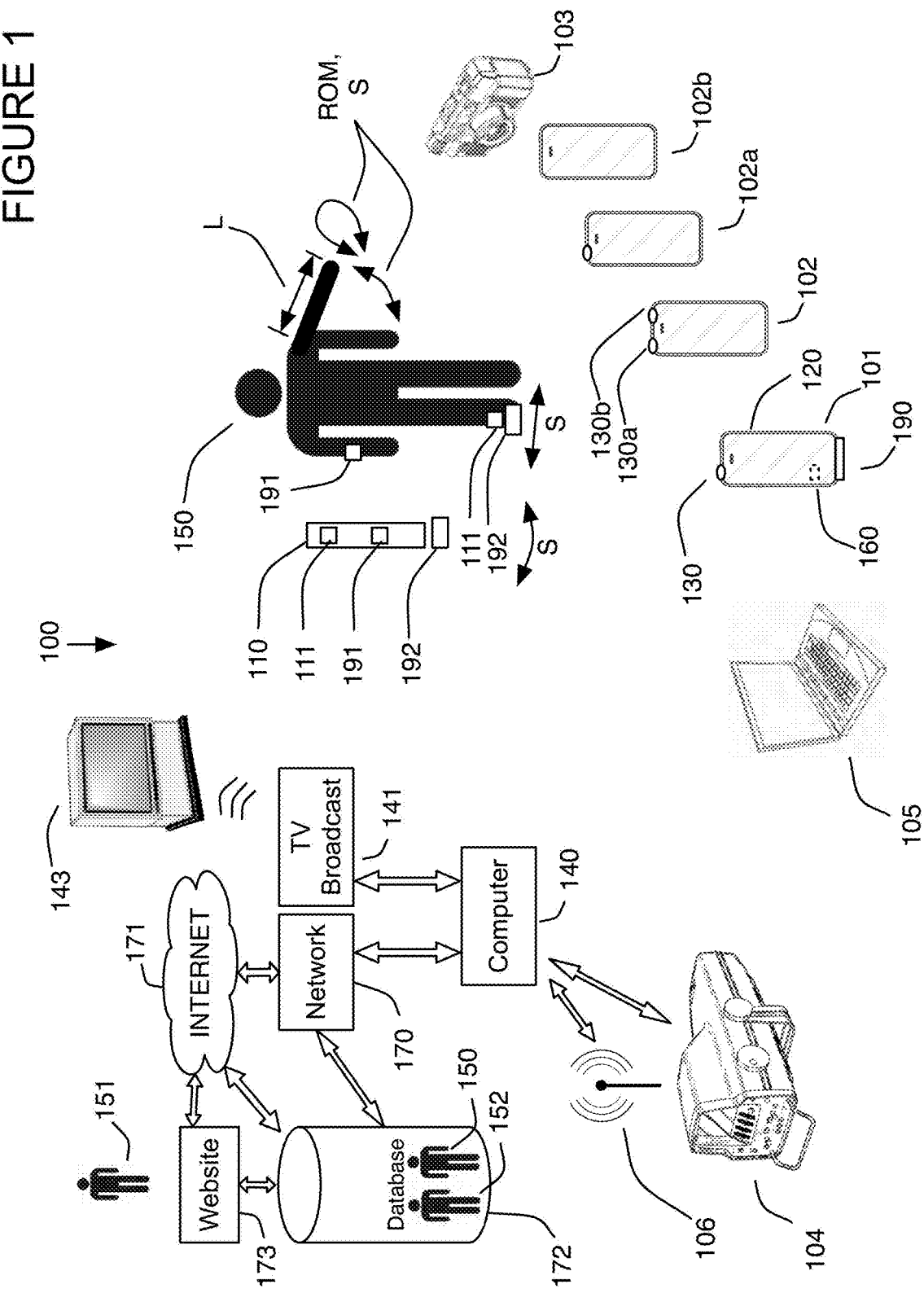
FIG. 1 illustrates an embodiment of the system that enables a system and method for utilizing motion capture data.

FIG. 1 illustrates an embodiment of the fitting system for sporting equipment 100. As shown, embodiments of the system generally include a mobile device 101 and applications that execute thereon, that includes computer 160, shown as located internally in mobile device 101 as a dotted outline, (i.e., also see functional view of computer 160 in FIG. 1A), display 120 coupled to computer 160 and a wireless communications interface (generally internal to the mobile device, see element 164 in FIG. 1A) coupled with the computer. Since mobile phones having mobile computers are ubiquitous, users of the system may purchase one or more motion capture elements and an application, a.k.a., "app", that they install on their pre-existing phone to implement an embodiment of the system. Motion capture capabilities are thus available at an affordable price for any user that already owns a mobile phone, tablet computer, music player, etc., which has never been possible before. Embodiments of the mobile device execute the app, which is specifically programmed to prompt and accept motion inputs from a given motion capture sensor as moved by the user to specific locations or through rotations, to measure a dimension or size of user 150, or range of motion. For example, the app may prompt the user to move motion capture sensor 111 by hand, after removal from piece of equipment 110, between the user's other hand and shoulder. The distance between the two points is shown as length "L", e.g., of the user's arm. In addition, the system may prompt the user for a range of motion, shown as "ROM" with the sensor held in the other hand and with the sensor moved by the user as prompted from the side to the highest point with the arm extended, or with the wrist rotated while at the same location, to measure that specific range of motion for that body part. Embodiments may optionally only measure a range of motion and determine "L" via as the center point of the radius of the range of motion as well. The system may also measure the speed, shown as "S" at the same time or with piece of equipment 110, e.g., after motion capture sensor 111 is again coupled with the piece of equipment as prompted by the system for example, or alternatively with an existing motion capture sensor mounted on the piece of equipment via mount 192. Embodiments may also then utilize the same sensor to capture motion data from the piece of equipment, for example to further optimize the fit of and/or further collect motion capture data. Embodiments may provide information related to the optimal fit or otherwise suggest purchase of a particular piece of sporting equipment. Embodiments may utilize correlation or other algorithms or data mining of motion data for size, range of motion, speed of other users to maximize the fit of a piece of equipment for the user based on other user's performance with particular equipment. For example, this enables a user of a similar size, range of motion and speed to data mine for the best performance equipment, e.g., longest drive, lowest putt scores, highest winning percentage, etc., associated with other users having similar characteristics.

Specifically, one or more embodiments of the fitting system for sporting equipment include at least one motion capture element 111 that includes a wireless communication interface configured to transmit motion capture data from the at least one motion capture element and an application configured to execute on computer 160 within a mobile device, e.g., 101, 102, 102a, 102b, 103 or 105 that is configured to wirelessly communicate with the motion capture sensor, and optionally configured to telephonically communicate. FIG. 1G shows the processing that occurs on the computer. In one or more embodiments the application is configured to prompt a first user to move the motion capture sensor to a first location at 1181 and accept a first motion capture data from the motion capture sensor at the first location via the wireless communication interface, prompt the first user to move the motion capture sensor to a second location or rotation at 1182, accept a second motion capture data or rotation from the motion capture sensor at the second location via the wireless communication interface, calculate a distance or rotation at 1183 between the first and second location or rotation based on the first and second motion capture data. The distance may include a height or an arm length, or a torso length, or a leg length, or a wrist to floor measurement, or a hand size or longest finger size or both the hand size and longest finger size of the first user, or any combination thereof or any other dimension or length associated with the first user. Distances may be calculated by position differences, or by integrating velocity or doubly integrating acceleration, or in any other manner determining how far apart or how much rotation has occurred depending on the types of internal sensors utilized in the motion capture sensor as one skilled in the art will appreciate. For example, embodiments of the invention may prompt the user to hold the motion capture sensor in the user's hand and hold the hand on top of the user's head and then prompt the user to place the sensor on the ground, to calculate the distance therebetween, i.e., the height of the user. In another example, the system may prompt the user to hold the sensor in the hand, for example after decoupling the sensor from a golf club and then prompt the user to place the sensor on the ground. The system then calculates the distance as the "wrist to floor measurement", which is commonly used in sizing golf clubs for example. Embodiments of the system may also prompt the user to move the sensor from the side of the user to various positions or rotational values, for example to rotate the sensor while at or through various positions to calculate the range of motion, for example through flexion, extension, abduction, adduction, lateral rotation, medial rotation, etc. Any of these characteristics, dimensions, distances, lengths or other parameters may be stored in Table 180a shown in FIG. 1B and associated with the particular user. In one or more embodiments, the application is further configured to prompt the first user to couple the motion capture sensor to a piece of equipment at 1184 and prompt the first user to move the piece of equipment through a movement at 1185, for example at the speed intended to be utilized when playing a particular sport or executing a particular movement associated with a piece of sporting equipment. The application is further configured to accept a third motion capture data from the motion capture sensor for the movement via the wireless communication interface and calculate a speed for the movement at 1186 based on the third motion capture data. In one or more embodiments, the application is configured to calculate a correlation at 1187 between the distance and the speed for the first user with respect to a plurality of other users and present information associated with an optimally fit or sized piece of equipment associated with other users. For example, the system may choose a second user having a maximum value correlation or correlation to the first user within a particular range, for example at least with the distance and the speed of the first user. The system may then search through the closest parameter users and choose the one with the maximum or minimum performance or score or distance of hitting, etc., and select the make/model of the piece of equipment for presentation to the user. For example, one such algorithm may for example provide a list of make and model of the lowest scoring golf shaft, or longest hitting baseball bat associated with a similar size/range of motion/speed user.

Embodiments of the user may use the speed of the user through motions or the speed of the equipment through motions or both in correlation calculations for example. The information for the best performing make/model and size of the piece of equipment is presented to the user at 1188.

Other embodiments may display one or more images to enable the first user to view a sporting event, for example via TV 143 or via any of the mobile devices, wireless devices capable of displaying an image 103, or other computers 101, 102, 102a, 102b or 105. Embodiments may accept an input from the first user to purchase the piece of equipment based the distance, or range of motion or the speed previously stored with respect to the first user or any combination thereof. For example, the piece of equipment may be shown in the sporting event, but sized to fit the user based on the user's previously stored or currently accepted or calculated parameters. Embodiments may also prompt the first user for their age and utilize this when calculation of the correlation is performed. Embodiments may present information associated with a grip or length of the optimally sized piece of equipment, or stiffness, or model or manufacturer, or any combination thereof.

Embodiments of the application may also be configured to recognize when the at least one motion capture element is removed from the piece of equipment based on the motion capture data. The application may for example accept gestures or analyze the motion to determine that it could not be output from a particular piece of equipment based on the motion. Alternatively, or in combination, embodiments of the invention may recognize when the at least one motion capture element is coupled with the piece of equipment based on the motion capture data. For example if the motion data is analyzed and is determined to have a path of motion indicative of a baseball bat swing or golf swing then, the system may indicate that the motion capture sensor is currently coupled to the piece of equipment. Furthermore, since different pieces of equipment may utilize the same sensor, for example after decoupling from one and placing in the other, particular types of motion, for example a skate board and a tennis racquet may be automatically determined based on a barrel roll of the skateboard or serve of the racquet which indicates the path of motion that is unique or at least indicative of that type of equipment. This enables automatic sensing of the piece of equipment currently coupled with the sensor.

Each mobile device 101, 102, 102a, 102b may optionally include an internal identifier reader 190, for example an RFID reader, or may couple with an identifier reader or RFID reader (see mobile device 102) to obtain identifier 191. Alternatively, embodiments of the invention may utilize any wireless technology in any of the devices to communicate an identifier that identifies equipment 110 to the system. The system generally may be utilized to fit any type of piece of equipment 110. The motion capture sensor(s) may couple with the user or piece of equipment via mount 192, for example to a golf club, or baseball bat, tennis racquet, hockey stick, weapon, stick, sword, or any other piece of equipment for any sport, or other sporting equipment such as a shoe, belt, gloves, glasses, hat, or any other item. The at least one motion capture element 111 may be placed at one end, both ends, or anywhere between both ends of piece of equipment 110 or anywhere on user 150 and may be utilized for EI measurements of any item. The motion capture element may optionally include a visual marker, either passive or active, and/or may include a wireless sensor, for example any sensor capable of providing any combination of one or more values associated with an orientation (North/South and/or up/down), position, velocity and/or acceleration of the motion capture element. The computer may be configured to obtain data associated with an identifier unique to each piece of equipment 110, e.g., clothing, bat, etc., for example from an RFID coupled with club 110, i.e., identifier 191, and optionally associated with the at least one motion capture element, either visually or wirelessly, analyze the data to form motion analysis data and display the motion analysis data on display 120 of mobile device 101. Motion capture element 111 may be mounted on or near the equipment or on or near the user via motion capture mount 192. The motion capture data from motion capture element 111, any data associated with the piece of equipment 110, such as identifier 191 and any data associated with user 150, or any number of such users 150, such as second user 152 may be stored in locally in memory, or in a database local to the computer or in a remote database, for example database 172. Data may be stored in database 172 from each user 150, 152 for example when a network or telephonic network link is available from motion capture element 111 to mobile device 101 and from mobile device 101 to network 170 or Internet 171 and to database 172. Data mining is then performed on a large data set associated with any number of users and their specific characteristics and performance parameters. For example, in a golf embodiment of the invention, a club ID is obtained from the golf club and a shot is detected by the motion capture element. Mobile computer 101 stores images/video of the user and receives the motion capture data for the events/hits/shots/motion and the location of the event on the course and subsequent shots and determines any parameters for each event, such as distance or speed at the time of the event and then performs any local analysis and display performance data on the mobile device. When a network connection from the mobile device to network 170 or Internet 171 is available or for example after a round of golf, the images/video, motion capture data and performance data is uploaded to database 172, for later analysis and/or display and/or data mining. In one or more embodiments, users 151, such as original equipment manufacturers pay for access to the database, for example via a computer such as computer 105 or mobile computer 101 or from any other computer capable of communicating with database 172 for example via network 170, Internet 171 or via website 173 or a server that forms part of or is coupled with database 172. Data mining may execute on database 172, for example that may include a local server computer, or may be run on computer 105 or mobile device 101, 102, 102a or 102b and access a standalone embodiment of database 172 for example. Data mining results may be displayed on mobile device 101, computer 105, television broadcast or web video originating from camera 130, 130a and 103b, or 104 or accessed via website 173 or any combination thereof.

One or more embodiments of the system may utilize a mobile device that includes at least one camera 130, for example coupled to the computer within the mobile device. This allows for the computer within mobile device 101 to command the camera 130 to obtain an image or images, for example of the user during an athletic movement. The image(s) of the user may be overlaid with displays and ratings to make the motion analysis data more understandable to a human for example. Alternatively, detailed data displays without images of the user may also be displayed on display 120 or for example on the display of computer 105. In this manner two-dimensional images and subsequent display thereof is enabled. If mobile device 101 contains two cameras, as shown in mobile device 102, i.e., cameras 130a and 130b, then the cameras may be utilized to create a three-dimensional data set through image analysis of the visual markers for example. This allows for distances and positions of visual markers to be ascertained and analyzed. Images and/or video from any camera in any embodiments of the invention may be stored on database 172, for example associated with user 150, for data mining purposes. In one or more embodiments of the invention image analysis on the images and/or video may be performed to determine make/models of equipment, clothes, shoes, etc., that is utilized, for example per age of user 150 or time of day of play, or to discover any other pattern in the data.

Alternatively, for embodiments of mobile devices that have only one camera, multiple mobile devices may be utilized to obtain two-dimensional data in the form of images that is triangulated to determine the positions of visual markers. In one or more embodiments of the system, mobile device 101 and mobile device 102a share image data of user 150 to create three-dimensional motion analysis data. By determining the positions of mobile devices 101 and 102 (via position determination elements such as GPS chips in the devices as is common, or via cell tower triangulation and which are not shown for brevity but are generally located internally in mobile devices just as computer 160 is), and by obtaining data from motion capture element 111 for example locations of pixels in the images where the visual markers are in each image, distances and hence speeds are readily obtained as one skilled in the art will recognize.

Camera 103 may also be utilized either for still images or as is now common, for video. In embodiments of the system that utilize external cameras, any method of obtaining data from the external camera is in keeping with the spirit of the system including wireless communication of the data, or via wired communication as when camera 103 is docked with computer 105 for example, which then may transfer the data to mobile device 101.

In one or more embodiments of the system, the mobile device on which the motion analysis data is displayed is not required to have a camera, i.e., mobile device 102b may display data even though it is not configured with a camera. As such, mobile device 102b may obtain images from any combination of cameras on mobile device 101, 102, 102a, camera 103 and/or television camera 104 so long as any external camera may communicate images to mobile device 102b. Alternatively, no camera is required at all to utilize the system.

FIGS. 1 and 1F also illustrate a broadcasting system and method for broadcasting images with augmented motion data including at least one camera 103, 104, configured to receive images associated with or otherwise containing at least one motion capture element 111, a computer 140, and a wireless communication interface 106 configured to receive motion capture data from the at least one motion capture element. In one or more embodiments, the computer 140 is coupled with the wireless communication interface 106 and the at least one camera, and the computer 140 is configured to receive the motion capture data after a communications link to the at least one motion capture element 111 is available and capable of receiving information for example as shown in FIG. 1F at 1191. Embodiments also may receive the motion capture data after an event or periodically request the motion capture data at 1192 as per FIG. 1F from the at least one motion capture element 111 as per FIG. 1. This enables the system to withstand communication link outages, and even enables the synchronization of video with motion capture data in time at a later point in time, for example once the motion capture element is in range of the wireless receiver. Embodiments may receive motion capture data from at least one motion capture element 111, for example from one user 150 or multiple users 150, 151, 152 or both. One or more embodiments also may recognize the at least one motion capture element 111 associated with a user 150 or piece of equipment 110 and associate the at least one motion capture element 111 with assigned locations on the user 150 or the piece of equipment 110, at 1193 of FIG. 1F. For example, when a user performs a motion event, such as swinging, hitting, striking, or any other type of motion-related activity, the system is able to associate the motion event with locations on the user, or equipment such as a golf club, racket, bat, glove, or any other object, to recognize, or identify, the at least one motion capture element. Embodiments may also receive data associated with the at least one motion capture element 111 via the wireless communication interface at 1194 as per FIG. 1F, and also may receive one or more images of the user associated with the motion capture element at 1195 of FIG. 1F from the at least one camera 103, 104. Such data and images allow the system to, for example, obtain an array of information associated with users, equipment, and events and/or to output various performance elements therefrom. One or more embodiments may also analyze the data to form motion analysis data at 1196 of FIG. 1F. Motion analysis data, for example, allows the system to obtain and/or output computer performance information to for example broadcast to the users, to viewers, coaches, referees, networks, and any other element capable of receiving such information. Motion analysis data for example may show motion related quantitative data in a graphical or other easy to understand viewing format to make the data more understandable to the user than for example pure numerical lists of acceleration data. For example, as shown in FIG. 1F, embodiments of the invention may also at 1197, draw a three-dimensional overlay onto at least one of the one or more images of the user, a rating onto at least one of the one or more images of the user, at least one power factor value onto at least one of the one or more images of the user, a calculated ball flight path onto at least one of the one or more images of the user, a time line showing points in time along a time axis where peak values occur onto at least one of the one or more images of the user, an impact location of a ball on the piece of equipment onto at least one of the one or more images of the user, a slow motion display of the user shown from around the user at various angles at normal speed onto at least one of the one or more images of the user, or any combination thereof associated with the motion analysis data. One or more embodiments may also broadcast the images at 1198, to a multiplicity of display devices including television 143, mobile devices 101, 102, 102a, 102b, computer 105, and/or to the Internet 171. For example, the multiplicity of display devices may include televisions, mobile devices, or a combination of both televisions and mobile devices, or any other devices configured to display images.

FIG. 1E illustrates a data flow diagram for an embodiment of the system that enables broadcasting and/or otherwise accessing previously stored motion capture data or motion analysis data. As shown, the computer 140 is coupled camera 104 to obtain image data and with wireless interface 106 and with TV broadcast component 141 and may also be configured to access previously stored motion capture data or motion analysis data associated with the user 150 or piece of equipment 110, or previously stored motion capture data or motion analysis data associated with at least one other user 152 or other piece of equipment. The data flow in this example is from the camera(s) and wireless interface through the computer and out to the Internet for viewing on any type of computer 105 and/or out to the TV broadcast equipment 141 for over the air, satellite or other television broadcast mechanism. This allows the system to, for example, analyze different movements or events associated with one player, a second player, historical players, a first piece of equipment such as a first golf club, or a second piece of equipment such as a second golf club, in order to obtain motion depiction for statistical use, for display use, for use in a game, or any other related application and broadcast the motion analysis data to a multiplicity of televisions or computers viewable by users 151. Embodiments may also broadcast information comprising at least one avatar associated with the at least one user on a virtual reality display based on the motion analysis data associated with the user or piece of equipment and the previously stored motion capture data or motion analysis data associated with the user or piece of equipment or the previously stored motion capture data or motion analysis data associated with at least one other user or other piece of equipment. For example, a player may play against an opponent, who may be a historical figure displayed as an avatar for example on a television 141, 143 or Internet broadcast to show the difference in performance between the player and a previous shot played by the same player or any other player. In addition, the images may be displayed on the virtual reality display, without the opponent, or historical figure, physically present with the player. In addition or alternatively, the computer may also be configured to broadcast the one or more images based on a comparison of the motion analysis data associated with the user or the piece of equipment and previously stored motion capture data or motion analysis data associated with the user or the piece of equipment or previously stored motion capture data or the motion analysis data associated with at least one other user. For example, this allows the player to be shown in contrast to a novice, an average, or a professional level player using motion analysis data from various groups of players.

In one or more embodiments, as also shown in FIG. 1E, the system may also comprise an identifier 191 coupled with the user 150, 152 or the piece of equipment 110. The computer 140 or wireless interface may also further include an identifier reader to obtain the identifier, and the computer may be further configured to receive the identifier in any manner and associate the identifier with the motion analysis data. This allows the computer to accurately identify, and/or locate, the user associated with the motion analysis data. This is especially useful when multiple users or several people are located in the same area, or when multiple events are taking place in the same area. Embodiments may further be configured to predict a first derivative or other derivate based on age or growth rates to determine the best fitting equipment for children, such as child 152 or adolescent or other user 150, that will fit for the longest time or otherwise minimize costs and maximize usage of equipment as well. This for example may be performed by differencing two measurement values in table 180*a*, dividing by the difference in the dates when the measurements where taken as per the date/time field, to determine a rate of growth and predicting a size at a future point in time to determine the longest time that a particular piece of equipment should last for the user for example based on predicted growth rates for similar persons or persons within an age range. Other embodiments of the invention may suggest exercises and/or stretches that would improve performance to a predicted performance level based on other users performance data and suggest equipment that would be appropriate for an increase strength or flexibility so that users can "grow into" or "improve into" equipment. Through use of the range of motion and date/time fields, and using the differences therebetween, the range of motion over time may be shown to increase, decrease or stay the same. In addition, other embodiments of the invention may be utilized over time to detect tight areas or areas that may be indicative of injury for example and alert the user in a similar manner. For example if the range of motion or speed S decreases, over time, the user may be alerted or a massage may be automatically scheduled for example. The user may be alerted in any manner to the changes and exercises or stretches or other equipment may be suggested to the user. One or more embodiments of the invention may be utilized for gait analysis for fitting of shoes, for example for improved standing, walking or running. In one or more embodiments, the step and stride length and time between steps or cadence, the speed, angle of the foot and other limbs for example if instrumented with more than one sensor, the pressure may also be obtained as per FIG. 13 and the associated pressure detecting apparatus and stored for in table 180*a*. Any combination of these may be determined and/or otherwise derived and utilized for example compared to baselines or thresholds or ranges to determine where problems exist or where a piece of equipment provides adequate or optimal fit.

In one or more embodiments, the computer is further configured to broadcast the images to enable a multiplicity of viewers to purchase the piece of equipment based on the images, and may also be configured to broadcast an advertisement with information related to purchasing the piece of equipment based the images. For example, the player, or piece of equipment of interest, may have a new maximum power factor for a given swing, or compared to the average power factor of average users, or professionals, suggesting that the piece of equipment used by the player may improve performance, in the interest of the potential buyer. Furthermore, for example, an advertisement may be displayed at the bottom of a display screen, or anywhere else on a display screen, showing the new maximum power factor along with a URL or other information related to the equipment, allowing the viewer to purchase the equipment. Other information related to the equipment may comprise phone numbers, addresses, names, vendors, events or any other data helpful to the viewer in purchasing the equipment. In addition to, or alternatively, the computer may be further configured to broadcast the images to enable a multiplicity of viewers to order a custom fitted piece of equipment over a network, for example by specifying their height or other dimensions for example alone or in combination with previously stored motion capture data or physical parameters as measured or derived therefrom.

At least one of the previously disclosed embodiments may also be configured to intermittently receive the motion capture data and synchronize the images in time with the motion capture data, for example from motion capture sensor(s) 111. This enables video capture and motion capture data to be combined at a later timer, as opposed to real-time combination of video and data. This enables intelligent low power usage on the motion capture element since the transmitter is not required to be transmitting continuously. In one or more embodiments, the computer may be configured to intermittently receive the motion capture data and synchronize the images in time with the motion capture data based on location information associated with the images, and location information, an identifier and time associated with the motion capture element. The computer of one or more embodiments may also be configured to intermittently receive the motion capture data and synchronize the images in time with the motion capture data based on time and an identifier associated with the images, and time and an identifier associated with the motion capture data element. Also, in one or more embodiments, the computer may be configured to intermittently receive the motion capture data and synchronize the images in time with the motion capture data based on time, location information and a motion event associated with the images, and time, location information and a motion event associated with the motion capture data element. Configuring the computer as such allows the system to identify and locate the user associated with the images and motion capture data received, by either using time and an identifier of the images and motion capture element, or time, location and an event associated with the images or motion capture data element. Using an identifier, for example, allows the system to accurately identify a specific motion capture element associated with the user or piece of equipment, especially when the motion capture data is obtained from a previously stored or recorded event, rather than in real time. Also, using an event associated with the images and motion capture data element, in addition to the location and time, for example, allows the system to accurately identify a specific motion associated with the user or piece of equipment. A specific motion may include, a swing, a strike, a hit, or any other motion-related data, associated with the user or piece of equipment. For example, if multiple players are located on a golf course, or if a player is advancing from one hole to the next on a golf course, using the location, time and event (or identifier in some instances) associated with the player or pieces of equipment, the system is able to identify which player performed which event at which location and at what time. Furthermore, the system is able to correlate the data received to the correct player, based on the location, time, and event (or in some instances, identifier) information available. This enables the system to broadcast images with augmented motion data at a later time and still be able to accurately associate the data and information obtained to a specific user or piece of equipment and to the images thereof.

For television broadcasts, motion capture element 111 wirelessly transmits data that is received by antenna 106. The wireless sensor data thus obtained from motion capture element 111 is combined with the images obtained from television camera 104 to produce displays with augmented motion analysis data that can be broadcast to televisions, computers such as computer 105, mobile devices 101, 102, 102a, 102b or any other device configured to display images, for example as broadcast using television broadcast equipment 141. The motion analysis data can be positioned on display 120, or television 143 or computer screen on computer 105 for example by knowing the location of a camera (for example via GPS information), and by knowing the direction and/or orientation that the camera is pointing so long as the sensor data includes location data (for example GPS information). In other embodiments, visual markers or image processing may be utilized to lock the motion analysis data to the image, e.g., the golf club head can be tracked in the images and the corresponding high, middle and low position of the club can be utilized to determine the orientation of user 150 to camera 130 or 104 or 103 for example to correctly plot the augmented data onto the image of user 150. By time stamping images and time stamping motion capture data, for example after synchronizing the timer in the microcontroller with the timer on the mobile device and then scanning the images for visual markers or sporting equipment at various positions, simplified motion capture data may be overlaid onto the images. Any other method of combining images from a camera and motion capture data may be utilized in one or more embodiments of the invention. Any other algorithm for properly positioning the motion analysis data on display 120 with respect to a user (or any other display such as on computer 105) may be utilized in keeping with the spirit of the system. In one or more embodiments, the velocity of zero point in a swing, for example at the maximum of a backswing may be utilized to pinpoint a club head in an image, wherein the maximum rearmost position in the image may be matched with the horizontal orientation obtained from the motion capture data while the strike point in the image may be matched with the impact point where impact oscillations begin to occur in the motion capture data. A line may be then drawn, for example tracing the path of the contrast or color of the club head as directed or accepted as inputs into computer 140. The points that are connected may be further modified on computer 140 and the drawing may thus be completed and broadcast out to the Internet and over the television broadcast equipment for example.

One such display that may be generated and displayed on mobile device 101 include a BULLET TIME® view using two or more cameras selected from mobile devices 101, 102, 102a, camera 103, and/or television camera 104 or any other external camera. In this embodiment of the system, the computer is configured to obtain two or more images of user 150 and data associated with the at least one motion capture element (whether a visual marker or wireless sensor), wherein the two or more images are obtained from two or more cameras and wherein the computer is configured to generate a display that shows slow motion of user 150 shown from around the user at various angles at normal speed. Such an embodiment for example allows a group of fans to create their own BULLET TIME® shot of a golf pro at a tournament for example. The shots may be sent to computer 105 and any image processing required may be performed on computer 105 and broadcast to a television audience for example. In other embodiments of the system, the users of the various mobile devices share their own set of images, and or upload their shots to a website for later viewing for example. Embodiments of the invention also allow images or videos from other players having mobile devices to be utilized on a mobile device related to another user so that users don't have to switch mobile phones for example. In one embodiment, a video obtained by a first user for a piece of equipment in motion that is not associated with the second user having the video camera mobile phone may automatically transfer the video to the first user for display with motion capture data associated with the first user.

FIG. 1A shows an embodiment of computer 160. In computer 160 includes processor 161 that executes software modules, commonly also known as applications, generally stored as computer program instructions within main memory 162. Display interface 163 drives display 120 of mobile device 101 as shown in FIG. 1. Optional orientation/position module 167 may include a North/South or up/down orientation chip or both. Communication interface 164 may include wireless or wired communications hardware protocol chips and/or an RFID reader or an RFID reader may couple to computer 160 externally or in any other manner for example. In one or more embodiments of the system communication interface may include telephonic and/or data communications hardware. In one or more embodiments communication interface 164 may include a Wi-Fi™ or other IEEE 802.11 device and/or BLUETOOTH® wireless communications interface or ZigBee® wireless device or any other wireless technology. BLUETOOTH® class 1 devices have a range of approximately 100 meters, class 2 devices have a range of approximately 10 meters. BLUETOOTH® Low Power devices have a range of approximately 50 meters. Any wireless network protocol or type may be utilized in embodiments of the system so long as mobile device 101 and motion capture element 111 can communicate with one another. Processor 161, main memory 162, display interface 163, communication interface 164 and orientation/position module 167 may communicate with one another over communication infrastructure 165, which is commonly known as a "bus". Communications path 166 may include wired or wireless medium that allows for communication with other wired or wireless devices over network 170. Network 170 may communicate with Internet 171 and/or database 172. Database 172 may be utilized to save or retrieve images or videos of users, or motion analysis data, or users displayed with motion analysis data in one form or another. The data uploaded to the Internet, i.e., a remote database or remote server or memory remote to the system may be viewed, analyzed or data mined by any computer that may obtain access to the data. This allows for original equipment manufacturers to determine for a given user what sporting equipment is working best and/or what equipment to suggest. Data mining also enables the planning of golf courses based on the data and/or metadata associated with users, such as age, or any other demographics that may be entered into the system. Remote storage of data also enables medical applications such as morphological analysis, range of motion over time, and diabetes prevention and exercise monitoring and compliance applications. Data mining based applications also allow for games that use real motion capture data from other users, one or more previous performances of the same user, or historical players whether alive or dead after analyzing motion pictures or videos of the historical players for example. Virtual reality and augmented virtual reality applications may also utilize the motion capture data or historical motion data. The system also enables uploading of performance related events and/or motion capture data to database 172, which for example may be implemented as a social networking site. This allows for the user to "tweet" high scores, or other metrics during or after play to notify everyone on the Internet of the new event.

FIG. 1B illustrates an architectural view of an embodiment of database 172 utilized in embodiments of the system. As shown tables 180-185 include information related to N number of users, M pieces of equipment per user, K user measurements (size, range of motion, speed for particular body parts/joints), P number of sensors per user or equipment, S number of sensor data per sensor, T number of patterns found in the other tables, and D number of data users. All tables shown in FIG. 1B are exemplary and may include more or less information as desired for the particular implementation. Specifically, table 180 includes information related to user 150 which may include data related to the user such as age, height, weight, sex, address or any other data. Table 180a includes information related to the various distances between joints or any other dimensions of the human body, along with any range of motion for any desired parts of the body, along with speed of any desired parts of the body. The table may contain sport specific values of interest "wrist to floor" for golf, or may derive these quantities based on other measurements for example. Any other physical characteristics may also be stored in this table for a particular user as desired for the particular fitting application. Table 181 include information related to M number of pieces of equipment 110, which may include clubs, racquets, bats, shirts, pants, shoes, gloves, helmets, etc., for example the manufacturer of the equipment, model of the equipment, and type of the equipment. For example, in a golf embodiment, the manufacturer may be the name of the manufacturer, the model may be a name or model number and the type may be the club number, i.e., 9 iron, the equipment ID may be identifier 191 in one or more embodiments of the invention. Table 182 may include information related to P number of sensors 111 on user 150 or equipment 110 or mobile computer 101. The sensors associated with user 150 may include clothing, clubs, etc., the sensors associated with equipment 110 may for example be motion capture data sensors, while the sensors associated with mobile computer 101 may include sensors 167 for position/orientation and sensors 130 for images/video for example. Table 183 may include information related to S number of sensor data per user per equipment, wherein the table may include the time and location of the sensor data, or any other metadata related to the sensor data such as temperature, weather, humidity, etc., or the sensor data may include this information or any combination thereof. The table may also contain a myriad of other fields, such as ball type, i.e., in a golf embodiment the type of golf ball utilized may be saved and later data mined for the best performing ball types, etc. Table 184 may include information related to T number of patterns that have been found in the data mining process for example. This may include fields that have been searched in the various tables with a particular query and any resulting related results. Any data mining results table type may be utilized in one or more embodiments of the invention as desired for the particular implementation. This may include search results of any kind, including EI measurements, which also may be calculated on computer 160 locally, or any other search value from simple queries to complex pattern searches. Table 185 may include information related to D number of data mining users 151 and may include their access type, i.e., full database or pattern table, or limited to a particular manufacturer, etc., the table may also include payment requirements and/or receipts for the type of usage that the data mining user has paid for or agreed to pay for and any searches or suggestions related to any queries or patterns found for example. Any other schema, including object oriented database relationships or memory based data structures that allow for data mining of sensor data including motion capture data is in keeping with the spirit of the invention. Although exemplary embodiments for particular activities are given, one skilled in the art will appreciate that any type of motion based activity may be captured and analyzed by embodiments of the system using a motion capture element and app that runs on a user's existing cell phone 101, 102 or other computer 105 for example.

There are a myriad of applications that benefit and which are enabled by embodiments of the system that provide for viewing and analyzing motion capture data on the mobile computer or server/database, for example for data mining database 172 by users 151. For example, users 151 may include compliance monitors, including for example parents, children or elderly, managers, doctors, insurance companies, police, military, or any other entity such as equipment manufacturers that may data mine for product improvement. For example in a tennis embodiment by searching for top service speeds in Table 183 for users of a particular size, range of motion, speed, as per Table 180a or age via Table 180, or in a golf embodiment by searching for distances, i.e., differences in sequential locations in table 183 based on swing speed in the sensor data field in table 183 to determine which make or model would be the optimal scoring or fitting piece of equipment for a particular user based on the data associated with other similar users. Other embodiments related to compliance enable messages from mobile computer 101 or from server/database to be generated if thresholds for G-forces, (high or zero or any other levels), to be sent to compliance monitors, managers, doctors, insurance companies, etc., as previously described. Users 151 may include marketing personnel that determine which pieces of equipment certain users own and which related items that other similar users may own, in order to target sales at particular users. Users 151 may include medical personnel that may determine how much movement a sensor for example coupled with a shoe, i.e., a type of equipment, of a diabetic child has moved and how much this movement relates to the average non-diabetic child, wherein suggestions as per table 185 may include giving incentives to the diabetic child to exercise more, etc., to bring the child in line with healthy children. Sports physicians, physiologists or physical therapists may utilize the data per user, or search over a large number of users and compare a particular movement of a user or range of motion for example to other users to determine what areas a given user can improve on through stretching or exercise and which range of motion areas change over time per user or per population and for example what type of equipment a user may utilize to account for changes over time, even before those changes take place. Data mining motion capture data and image data related to motion provides unique advantages to users 151. Data mining may be performed on flex parameters measured by the sensors to determine if sporting equipment, shoes, human body parts or any other item changes in flexibility over time or between equipment manufacturers or any combination thereof.

To ensure that analysis of user 150 during a motion capture includes images that are relatively associated with the horizon, i.e., not tilted, the system may include an orientation module that executes on computer 160 within mobile device 101 for example. The computer is configured to prompt a user to align the camera along a horizontal plane based on orientation data obtained from orientation hardware within mobile device 101. Orientation hardware is common on mobile devices as one skilled in the art will appreciate. This allows the image so captured to remain relatively level with respect to the horizontal plane. The orientation module may also prompt the user to move the camera toward or away from the user, or zoom in or out to the user to place the user within a graphical "fit box", to somewhat normalize the size of the user to be captured. Images may also be utilized by users to prove that they have complied with doctors' orders for example to meet certain motion requirements.

Embodiments of the system are further configured to recognize the at least one motion capture element associated with user 150 or piece of equipment 110 and associate at least one motion capture element 111 with assigned locations on user 150 or piece of equipment 110. For example, the user can shake a particular motion capture element when prompted by the computer within mobile device 101 to acknowledge which motion capture element the computer is requesting an identity for. Alternatively, motion sensor data may be analyzed for position and/or speed and/or acceleration when performing a known activity and automatically classified as to the location of mounting of the motion capture element automatically, or by prompting the user to acknowledge the assumed positions.

One or more embodiments of the computer in mobile device 101 is configured to obtain at least one image of user 150 and display a three-dimensional overlay onto the at least one image of user 150 wherein the three-dimensional overlay is associated with the motion analysis data. Various displays may be displayed on display 120. The display of motion analysis data may include a rating associated with the motion analysis data, and/or a display of a calculated ball flight path associated with the motion analysis data and/or a display of a time line showing points in time along a time axis where peak values associated with the motion analysis data occur and/or a suggest training regimen to aid the user in improving mechanics of the user. These filtered or analyzed data sensor results may be stored in database 172, for example in table 183, or the raw data may be analyzed on the database (or server associated with the database or in any other computer or combination thereof in the system shown in FIG. 1 for example), and then displayed on mobile computer 101 or on website 173, or via a television broadcast from camera 104 for example. Data mining results may be combined in any manner with the unique displays of the system and shown in any desired manner as well.

Embodiments of the system may also present an interface to enable user 150 to purchase piece of equipment 110 over the wireless interface of mobile device 101, for example via the Internet, or via computer 105 which may be implemented as a server of a vendor. In addition, for custom fitting equipment, such as putter shaft lengths, or any other custom sizing of any type of equipment, embodiments of the system may present an interface to enable user 150 to order a customer fitted piece of equipment over the wireless interface of mobile device 101. Embodiments of the invention also enable mobile device 101 to suggest better performing equipment to user 150 or to allow user 150 to search for better performing equipment as determined by data mining of database 172 for distances of golf shots per club for users with swing velocities within a predefined range of user 150. This allows for real life performance data to be mined and utilized for example by users 151, such as OEMs to suggest equipment to user 150, and be charged for doing so, for example by paying for access to data mining results as displayed in any computer shown in FIG. 1 or via website 173 for example. In one or more embodiments of the invention database 172 keeps track of OEM data mining and is configured to bill users 151 for the amount of access each of users 151 has purchased and/or used for example over a giving billing period. See FIG. 1B for example. In addition, for broadcast embodiments, performance data of any form, e.g., overlays or power factors of a player on television may be broadcast and displayed on any computer coupled with the system. The broadcast may include an advertisement or information that enables purchase of the equipment. The user may input a purchase command into computer 105 or mobile device 101 for the type of equipment shown, and input their physical characteristics, e.g., height, etc., or the system may retrieve the information from database 172 in order to enable user 150 or 151 to purchase equipment.

Embodiments of the system are configured to analyze the data obtained from at least one motion capture element and determine how centered a collision between a ball and the piece of equipment is based on oscillations of the at least one motion capture element coupled with the piece of equipment and display an impact location based on the motion analysis data. This performance data may also be stored in database 172 and used by OEMs or coaches for example to suggest clubs with higher probability of a centered hit as data mined over a large number of collisions for example.

While FIG. 1A depicts a physical device, the scope of the systems and methods set forth herein may also encompass a virtual device, virtual machine or simulator embodied in one or more computer programs executing on a computer or computer system and acting or providing a computer system environment compatible with the methods and processes implementing the disclosed ideas. Where a virtual machine, process, device or otherwise performs substantially similarly to that of a physical computer system of the system, such a virtual platform will also fall within the scope of a system of the disclosure, notwithstanding the description herein of a physical system such as that in FIG. 1A.

Figure 1C:
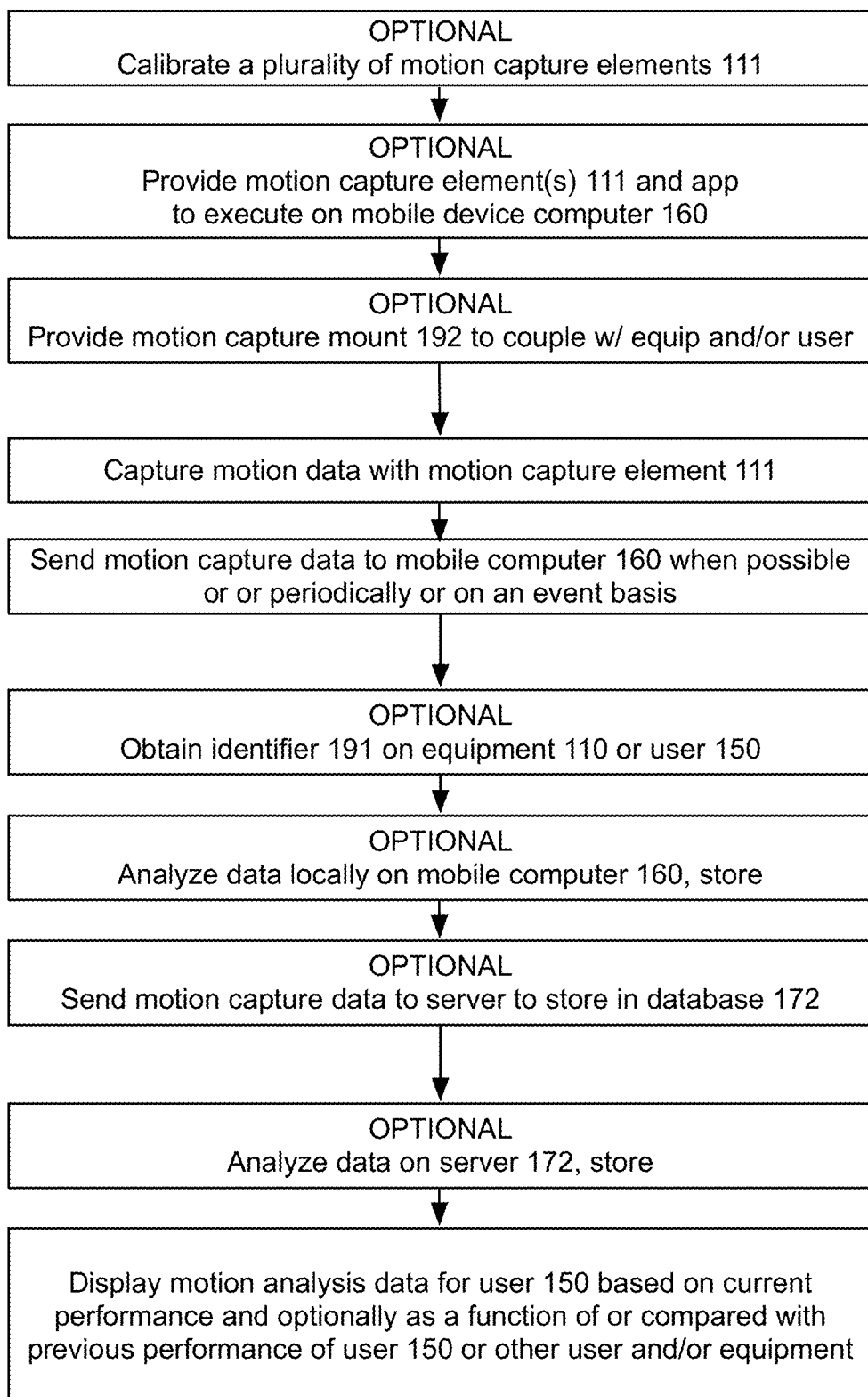
FIG. 1C illustrates a flow chart for an embodiment of the processing performed by embodiments of the computers in the system as shown in FIGS. 1 and 1A.
Figure 1G:
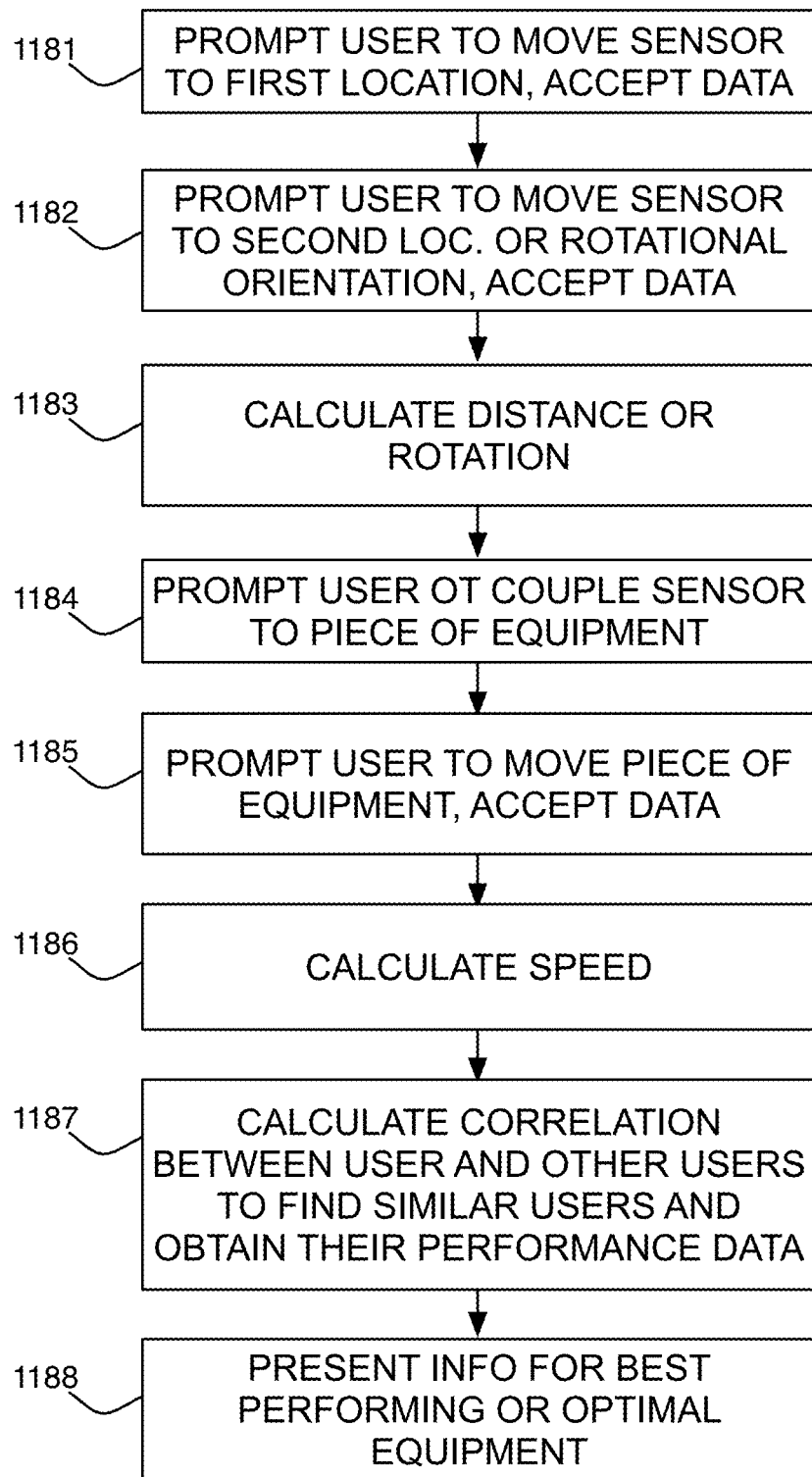
FIG. 1G illustrates a flow chart for an embodiment of the system.

FIG. 1C illustrates a flow chart for an embodiment of the processing performed and enabled by embodiments of the computers utilized in the system. In one or more embodiments of the system, optionally a plurality of motion capture elements are calibrated (see FIG. 11B for an example of a multiple motion capture element mounting device that may be moved in a specific manner to calibrate multiple sensors at once for mass production). In some embodiments this means calibrating multiple sensors on a user or piece of equipment to ensure that the sensors are aligned and/or set up with the same speed or acceleration values for a given input motion. In other embodiments of the invention, this means placing multiple motion capture sensors on a calibration object that moves and calibrates the orientation, position, speed, acceleration, or any combination thereof at the same time. The next optional step involves providing motion capture elements and an app for example that allows a user with an existing mobile phone or computer to utilize embodiments of the system to obtain motion capture data, and potentially analyze and/or send messages based thereon. In one or more embodiments, users may simply purchase a motion capture element and an app and begin immediately using the system. One or more embodiments of the system also allow optionally for providing motion capture mounts for the particular desired mounting location on a user or equipment. The system captures motion data with motion capture element(s) and sends the motion capture data to a mobile computer 101, 102 or 105 for example, which may include an IPOD®, ITOUCH®, IPAD®, IPHONE®, ANDROID® Phone or any other type of computer that a user may utilize to locally collect data. One or more mounts may be utilized, include for an embodiment of the mobile computer, for example a small format IPOD®. This minimizes the complexity of the sensor and offloads processing to extremely capable computing elements found in existing mobile phones and other electronic devices for example. The transmitting of data from the motion capture elements to the user's computer may happen when possible, periodically, on an event basis, when polled, or in any other manner as will be described in various sections herein. This saves great amount of power compared to known systems that continuously send raw data in two ways, first data may be sent in event packets, within a time window around a particular motion event which greatly reduces the data to a meaningful small subset of total raw data, and secondly the data may be sent less than continuously, or at defined times, or when asked for data so as to limit the total number of transmissions. The main intelligence in the system is generally in the mobile computer or server where more processing power may be utilized and so as to take advantage of the communications capabilities that are ubiquitous in existing mobile computers for example. In one or more embodiments of the system, the mobile computer may optionally obtain an identifier from the user or equipment, such as a passive RFID or active RFID or other identifier, which may be utilized by the mobile computer to determine what weight as user is lifting, or what shoes a user is running with, or what weapon a user is using, or what type of activity a user is using based on the identifier of the equipment. The mobile computer may analyze the motion capture data locally and display, i.e., show or send information such as a message for example when a threshold is observed in the data, for example when too many G-forces have been registered by a soldier or race car driver, or when not enough motion is occurring (either at the time or based on the patterns of data in the database as discussed below based on the user's typical motion patterns or other user's motion patterns for example.) In other embodiments, once a user has performed a certain amount of motion, a message may be sent to compliance monitor(s), including for example parents, children or elderly, managers, doctors, insurance companies, police, military, or any other entity such as equipment manufacturers. The message may be an SMS message, or email, or tweet or any other type of electronic communication. If the particular embodiment is configured for remote analysis or only remote analysis, then the motion capture data may be sent to the server/database. If the implementation does not utilize a remote database, the analysis on the mobile computer is local. If the implementation includes a remote database, then the analysis may be performed on the mobile computer or server/database or both. Once the database obtains the motion capture data, then the data may be analyzed and a message may be sent from the server/database to compliance personnel or business entities as desired. Embodiments of the invention make use of the data from the mobile computer and/or server for gaming, morphological comparing, compliance, tracking calories burned, work performed, monitoring of children or elderly based on motion or previous motion patterns that vary during the day and night, safety monitoring for troops when G-forces exceed a threshold or motion stops, local use of running, jumping throwing motion capture data for example on a cell phone including virtual reality applications that make use of the user's current and/or previous data or data from other users, or play music or select a play list based on the type of motion a user is performing or data mining. For example if motion is similar to a known player in the database, then that user's playlist may be sent to the user's mobile computer 101. The processing may be performed locally so if the motion is fast, fast music is played and if the motion is slow, then slow music may be played. Any other algorithm for playing music based on the motion of the user is in keeping with the spirit of the invention. Any use of motion capture data obtained from a motion capture element and app on an existing user's mobile computer is in keeping with the spirit of the invention, including using the motion data in virtual reality environments to show relative motion of an avatar of another player using actual motion data from the user in a previous performance or from another user including a historical player for example. Display of information is generally performed via three scenarios, wherein display information is based on the user's motion analysis data or related to the user's piece of equipment and previous data, wherein previous data may be from the same user/equipment or one or more other users/equipment. Under this scenario, a comparison of the current motion analysis data with previous data associated with this user/equipment allows for patterns to be analyzed with an extremely cost effective system having a motion capture sensor and app. Under another scenario, the display of information is a function of the current user's performance, so that the previous data selected from the user or another user/equipment is based on the current user's performance. This enables highly realistic game play, for example a virtual tennis game against a historical player wherein the swings of a user are effectively responded to by the capture motion from a historical player. This type of realistic game play with actual data both current and previously stored data, for example a user playing against an average pattern of a top 10 player in tennis, i.e., the speed of serves, the speed and angle of return shots, for a given input shot of a user makes for game play that is as realistic as is possible. Television images may be for example analyzed to determine swing speeds and types of shots taken by historical players that may no longer be alive to test one's skills against a master, as if the master was still alive and currently playing the user. Compliance and monitoring by the user or a different user may be performed in a third scenario without comparison to the user's previous or other user's previous data wherein the different user does not have access to or own for example the mobile computer. In other words, the mobile phone is associated with the user being monitored and the different user is obtaining information related to the current performance of a user for example wearing a motion capture element, such as a baby, or a diabetes patient.

FIG. 1D illustrates a data flow diagram for an embodiment of the system, for example that utilizes one or more motion capture elements and an "app" that is configured to execute on a mobile device. As shown motion capture data is sent from a variety of motion capture elements 111 on many different types of equipment or associated with user 150. The equipment or user may optionally have an identifier 191 that enables the system to associate a value with the motion, i.e., the weight being lifted, the type of racquet being used, the type of electronic device being used, i.e., a game controller or other object such as baby pajamas associated with second user 152, e.g., a baby. In one or more embodiments, elements 191 in the figure may be replaced or augmented with motion capture elements 111, as one skilled in the art will appreciate. In one or more embodiments of the system, mobile computer 101 receives the motion capture data, for example in event form and for example on an event basis or when requested by mobile computer 101, e.g., after motion capture elements 111 declares that there is data and turns on a receiver for a fix amount of time to field requests so as to not waste power, and if no requests are received, then turn the receiver off for a period of time. Once the data is in mobile computer 101, then the data is analyzed, for example to take raw or event based motion capture data and for example determine items such as average speed, etc., that are more humanly understandable in a concise manner. The data may be stored, shown to the right of mobile computer 101 and then the data may be displayed to user 150, or 151, for example in the form of a monitor or compliance text or email or on a display associated with mobile computer 101 or computer 105. This enables users not associated with the motion capture element and optionally not even the mobile computer potentially to obtain monitor messages, for example saying that the baby is breathing slowly, or for example to watch a virtual reality match or performance, which may include a user supplying motion capture data currently, a user having previously stored data or a historical player, such as a famous golfer, etc., after analysis of motion in video from past tournament performance(s). In gaming scenarios, where the data obtained currently, for example from user 150 or equipment 110, the display of data, for example on virtual reality glasses may make use of the previous data from that user/equipment or another user/equipment to respond to the user's current motion data, i.e., as a function of the user's input. The previous data may be stored anywhere in the system, e.g., in the mobile computer 101, computer 105 or on the server or database 172 (see FIG. 1).

Figure 2:
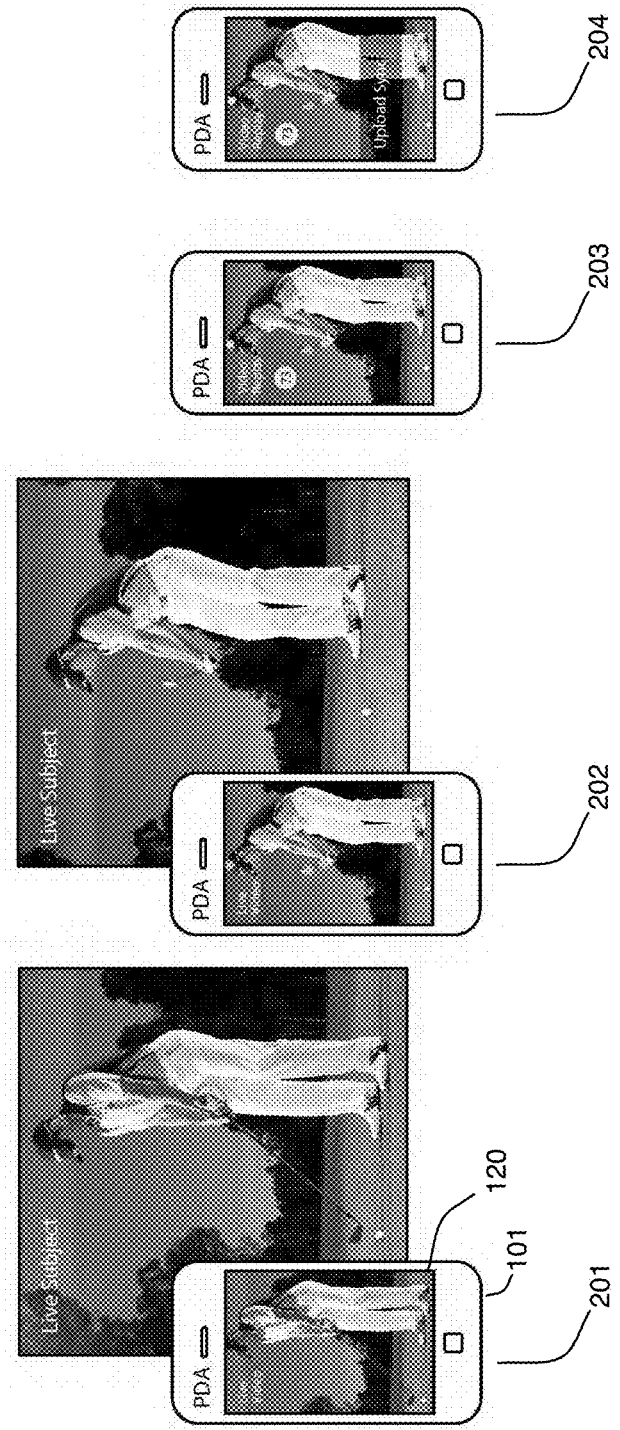
FIG. 2 illustrates an embodiment of the overall modes of the software programmed to execute on the computer of the mobile device, wherein the computer is configured to recognize the motion capture elements, obtain data, analyze the data and display motion analysis data.

FIG. 2 illustrates an embodiment of the overall modes of the software programmed to execute on the computer of the mobile device, wherein the computer is configured to optionally recognize the motion capture elements, obtain data, analyze the data and display motion analysis data. Mode 201 shows mobile device 101 having display 120 that displays a user with highlighted points on the user and/or piece of equipment. In this mode, each sensor is identified and assigned one by one to a particular area of the user or piece of equipment so as to recognize which sensors correspond to which movements of the user and/or piece of equipment. Mode 202 is the mode where the computer in mobile device obtains data associated with at least one motion capture element as recognized in mode 201. Mode 203 is the mode where the data is analyzed to form motion analysis data and display the motion analysis data optionally in conjunction with at least one image of the user. Mode 204 is the mode where the motion analysis data and optional at least one image of the user is saved, or retrieved to display at a later time. The images may be automatically captured from a second user's mobile device and transferred to the user's mobile device who swung the golf club so that they user's don't have to switch phones while playing to obtain image data for themselves. One algorithm embodiment detects a motion capture element data for a club that is not associated with the user of the video camera based mobile phone and queries nearby mobile devices to determine if they will accept the video. The mobile device of the user who performed the swing may automatically transfer the video so that after the user has swung, the user can look at their own phone and see their image overlaid with motion capture data without having users switch phones to capture video for each other. The motion capture data may be automatically stored in database 172 which for example may be in the form of a social network, in which case the transfer of data (for example a new maximum power score), may be automatically "tweeted" to Internet 171 and/or database 172 to notify everyone connected to the Internet of the new event. The upload of sensor data including any images/video and/or motion capture data may occur whenever a telephonic or other wireless link is available to database 172 for example. I.e., the motion capture sensors may store data until they have a wireless link to mobile computer 101, and mobile computer 101 may also buffer data including any analyzed motion capture data until a link to database 172 is available. Alternatively, the data transfers may occur at defined times, upon events such as a shot occurrence or distance moved by the mobile computer and hence the user, or polled by the database or in any other manner. Once the data is in database 172 it may be data mined as previously discussed.

Figure 3:
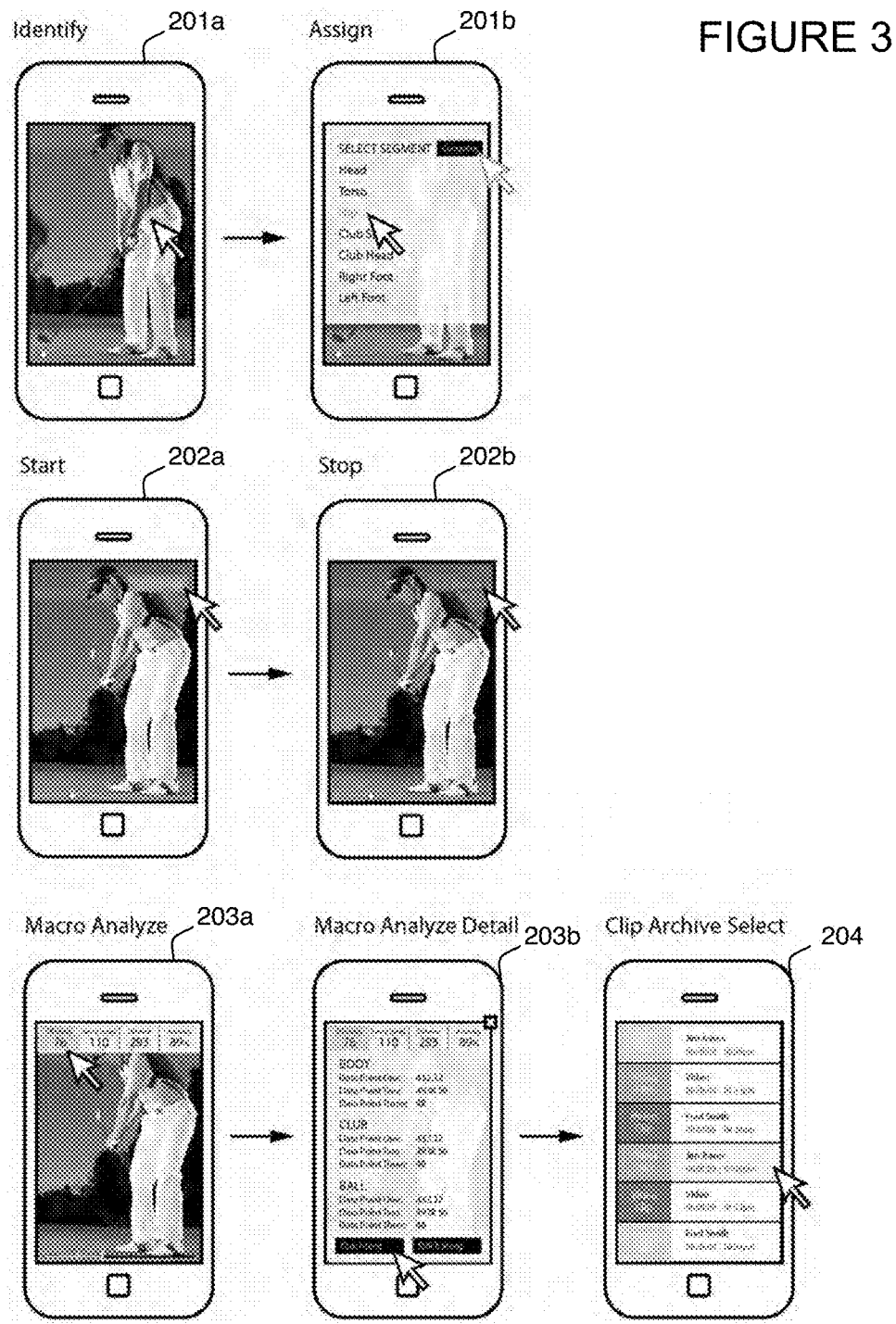
FIG. 3 illustrates displays associated with FIG. 2 in greater detail.

FIG. 3 illustrates displays associated with FIG. 2 in greater detail. Mode 201 includes sub-modes 201a where each motion capture element is asserted, moved, switched on or other wise identified. Data and/or metadata associated with the user such as age, height, weight, equipment manufacturer or model number and size may also be input in this screen. Alternatively, website 173 may be utilized to input this data or any other user related data for example. This allows for data mining the data and/or metadata and associated motion capture data later. Owners of database 172 may charge a fee for this service. Sub-mode 201b allows for assignment of the motion capture element so asserted to a particular body part of the user, or a location on the piece of equipment. Mode 202 includes sub-modes 202a where the computer obtains data associated with at least one motion capture element, either via image capture of one or more motion capture elements implemented as visual markers, or via wireless sensors, or both visual markers and wireless sensors. Mode 203 includes sub-mode 203a where main motion analysis data items may be displayed, and sub-mode 203b where detailed motion analysis data items may be displayed. Mode 204 shows selection of an archive name to store archive motion capture data, i.e., the motion analysis data and any images of the user. Mode 204 also allows for retrieval of an archived motion capture data by selected a list item on the display of the mobile device. In one or more embodiments, the motion capture archived data may be stored on the mobile device or remotely on computer 105, or in database 172 accessed via network 170 and/or via Internet 171.

Figure 4:
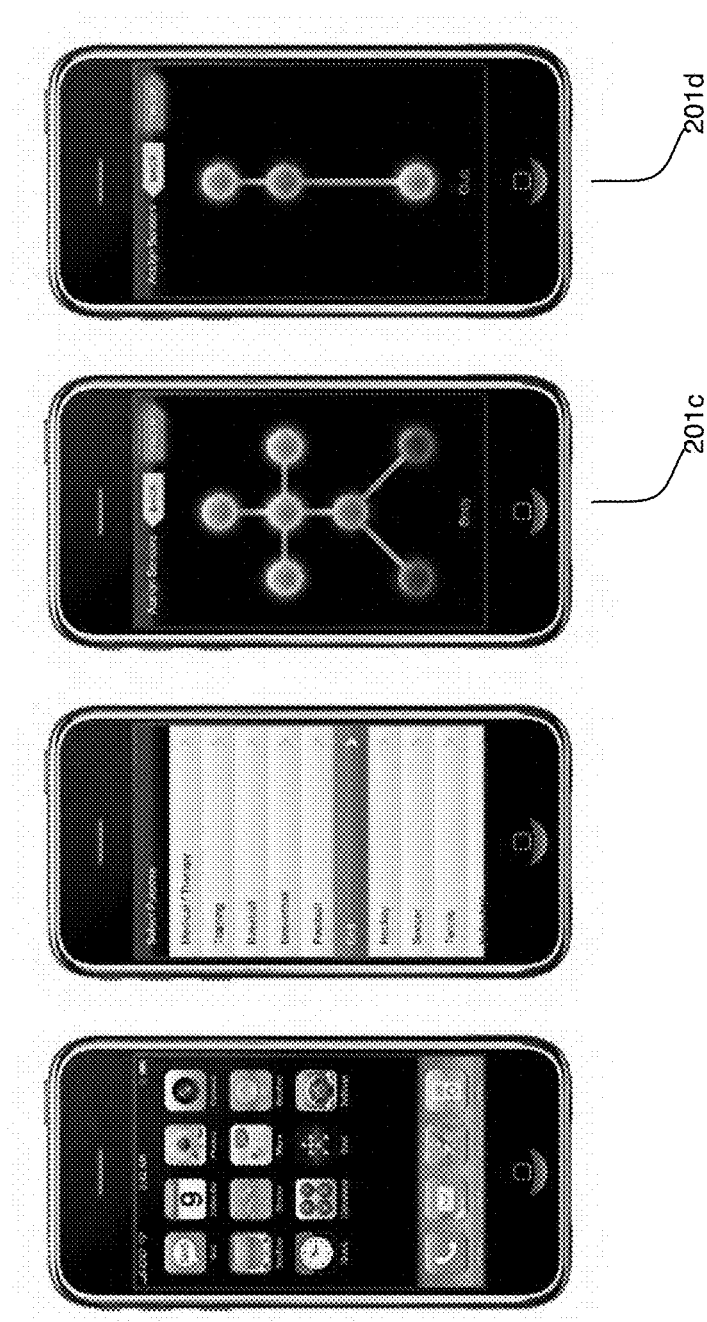
FIG. 4 illustrates and embodiment of the recognition module that is configured to assign particular sensors to particular locations on an athlete and/or on a piece of equipment.

FIG. 4 illustrates and embodiment of the recognition module that is configured to assign particular sensors to particular locations on an athlete and/or on a piece of equipment. In this simplified interface for mode 201, a mobile application is selected from the interface in the far left screen shot that then displays a number of activities or sports that can be motion captured by embodiments of the system. Selecting the desired sport via a finger gesture or any other manner in this display shows sub-mode screen 201c that allows for the assignment of sensors to areas of the user's body, and/or sub-mode screen 201d that allows for the assignment of sensors to areas on the equipment for the particular sport selected in the second screen from the left in the figure. Automatic determination of the assigned sensor locations is also possible based on analyzing the spatial data obtain from a golf swing. For example by determining the positions, or speed of the various sensors, an automatic assignment may be made, for example by taking the fastest moving component and assigning that to the golf club head, while taking the next fastest component and assigning that component to the hands, etc. Any other technique for automatically assigning sensors to locations of embodiments of the invention is in keeping with the spirit of the invention. In embodiments of the invention that utilize RFID or other identifier mechanism coupled with the golf club, such as a unique identifier per motion capture element for example, the user may enter a golf club number associated with a particular golf club so that the system knows which club is in proximity to the mobile computer or which golf club number for example has been moved through a golf swing. For baseball, the thick end of the bat generally moves faster and travels farther than the handle, and the system can automatically determine which sensor is which by analyzing the speed for example or total distance travelled when the bat is moved in a substantially horizontal plane. This automatic assignment makes the system easy to use and applies to all types of equipment, as one skilled in the art will appreciate.

Figure 5:
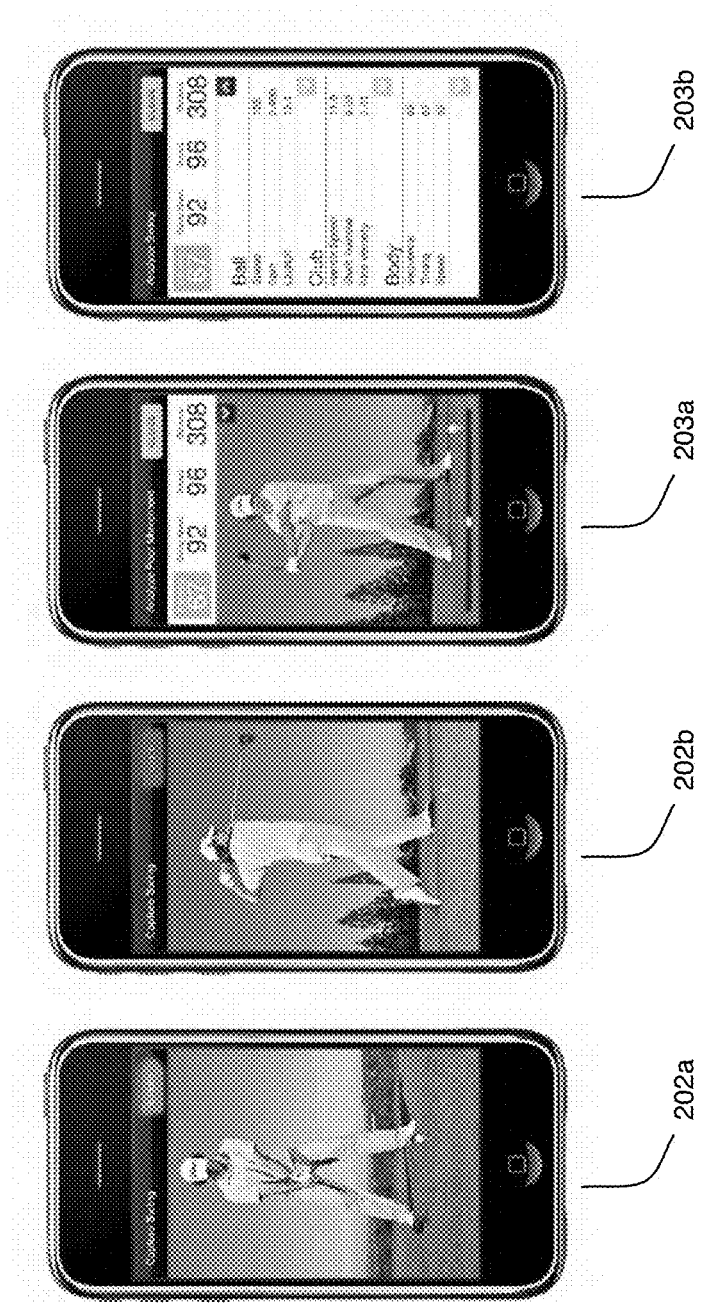
FIG. 5 illustrates an embodiment of the obtain data module that is configured to obtain data from a camera (optionally on the mobile device or obtain through another camera or camera on another mobile device), data from motion capture elements, i.e., any combination of visual markers or sensors as assigned to particular portions of the user's body or piece of equipment. In addition, the figure shows displays data analyzed by the analysis module and generated by the display module to show either the user along with motion analysis data, or with motion analysis data alone.

FIG. 5 illustrates an embodiment of the obtain data module that is configured to obtain data from a camera (optionally on the mobile device or obtain through another camera or camera on another mobile device) through asserting the "start" button on the display. Any other method of initiating the computer within the mobile device to obtain data is in keeping with the spirit of the system including user gestures such as moving the piece of equipment in a particular manner or in any other way. This is shown as sub-mode 202a. When motion data capture is to be terminated, any user gesture may be performed via the display of the mobile device, via the piece of equipment or via audio input to the mobile device for example. Any other method of informing the computer to no longer obtain data is in keeping with the spirit of the system. Sub-mode 203a where main motion analysis data items may be displayed, and sub-mode 203b where detailed motion analysis data items may be displayed are shown with "close" buttons, so that the data can be ignored for example. In addition, a slider in sub-mode 203a allows for precise control of the speed and/or location of the playback so that slow motion analysis may be utilized to better understand the analysis and display of motion analysis data. In addition, the figure shows displays data analyzed by the analysis module and generated by the display module to show either the user along with motion analysis data, or with motion analysis data alone. Double clicking or tapping on a detailed item may optionally display a list of exercises that a user may perform to increase the user's performance.

Figure 6:
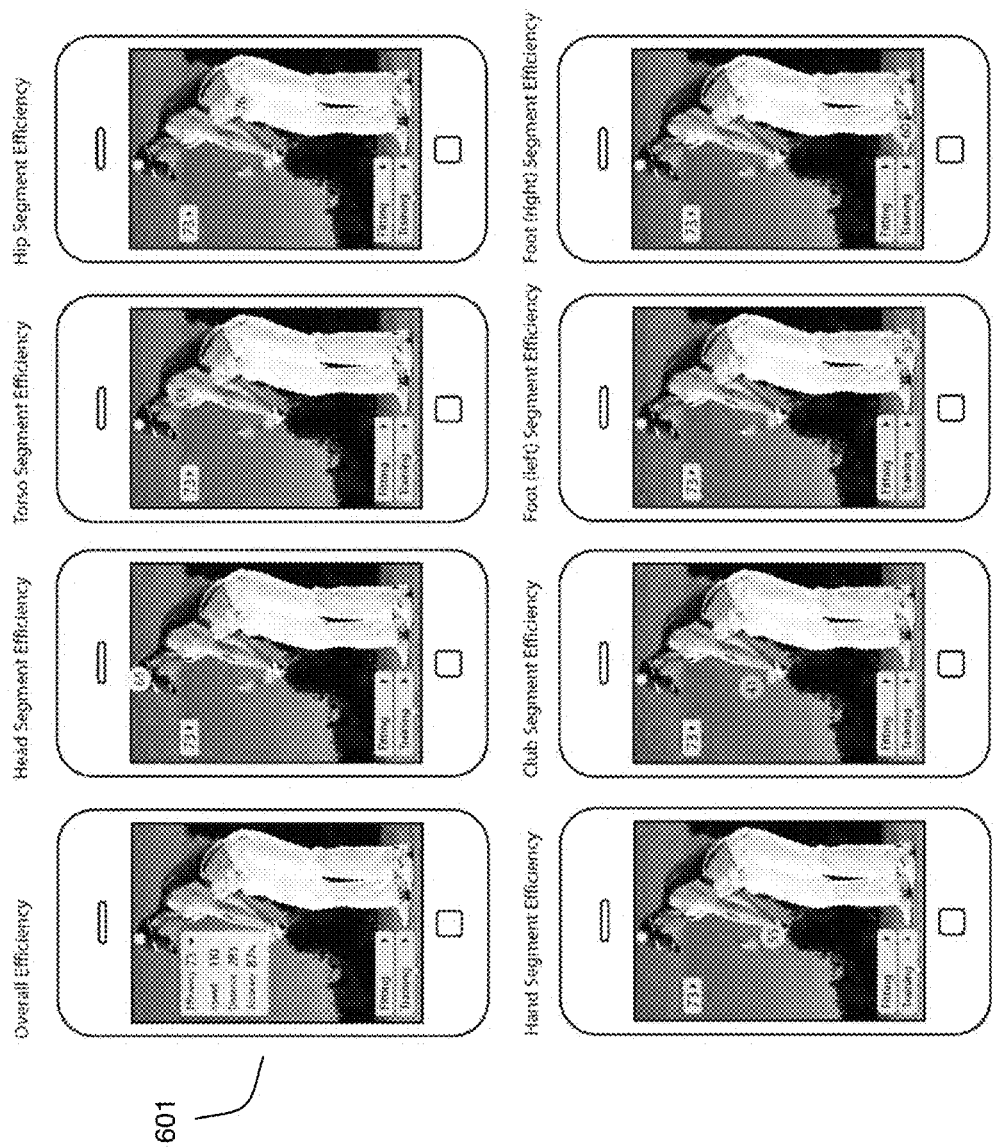
FIG. 6 illustrates a detailed drill down into the motion analysis data to display including overall efficiency, head, torso, hip, hand, club, left and right foot segment efficiencies. Embodiments of the invention thus enable physical training specific to the area that a user needs as determined by the analysis module.

FIG. 6 illustrates a detailed drill down into the motion analysis data to display including overall efficiency, head, torso, hip, hand, club, left and right foot segment efficiencies. Embodiments of the system thus enable physical training specific to the area that a user needs as determined by the analysis module. For example, asserting, double clicking or tapping, or clicking on the "training" button on the bottom of each efficiency screen as shown may display video, audio, or a list of exercises that a user may perform to increase the user's performance specific to that segment. In addition, by asserting the "fitting" button on each segment display, a detailed list of pieces of equipment that may perform better for the user based on the motion analysis data may be viewed. For example, if the user is swing too stiff of a golf club, then the golf club may be taking power out of the swing by slowing down before impacting a golf ball, while a more flexible shaft would speed up before impacting a golf ball. By asserting the "fitting" button, and based on the motion analysis data, for example club head speed or if multiple sensors are fitted on the shaft, then by the flexing of the shaft, then alternate golf clubs may be displayed to the user. The user may then press the purchase button, as will be detailed later, to purchase or custom order equipment that is better suited to the user. The displays shown in FIG. 6 or any of the other figures that display data associated with the user may also include data mining results or comparisons or suggestions or fields for searching and performing data mining. For example, the power factor achieved for a given swing may be compared against average users or professional users and suggest other equipment that may improve performance as per data mining patterns discovered in database 172 and stored for example in table 184. This data may be viewed in an augmented reality environment or with virtual reality glasses, etc.

Figure 7:
FIG. 7 illustrates a close up display of motion analysis data associated with a user, without use of an image associated with a user.

FIG. 7 illustrates a close up display of motion analysis data associated with a user, without use of an image associated with a user. In this close-up of sub-mode 203b, the efficiency, swing speed, release speed, face alignment angle and other quantities associated with the motion analysis data are displayed. Any data that is obtained or that can be analyzed and derived may be displayed. This includes any data previously saved in database 172 or data mined from database 172 for example. All of the embodiments shown in FIGS. 2-7 may be utilized to display physical characteristics of the user, or prompt the user for movement to enable the app to accept and calculate various physical dimensions or range of motion or speed or any combination thereof as one skilled in the art will recognize.

Figure 8:
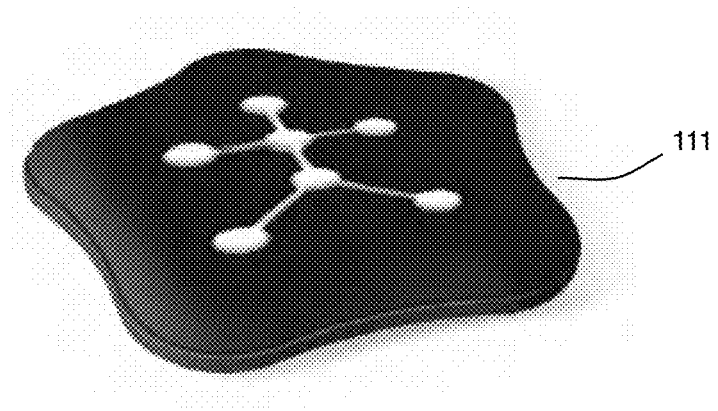
FIG. 8 illustrates an embodiment of the motion capture element that optionally includes a visual marker and/or sensor.

FIG. 8 illustrates an embodiment of the motion capture element that optionally includes a visual marker and/or sensor. One or more embodiments of the sensors are small, for example 12 mm or less in diameter and 4 mm or less thick in one embodiment. In addition, the sensors are inexpensive, lightweight, for example less than 5 grams in one or more embodiments. The sensors may utilize known wireless communications protocols such as BLUETOOTH™ with a range of approximately 10 meters for Bluetooth class 2, or 100 meters for Bluetooth class 1. Embodiments of the sensor may sample at 1200 times per second or higher or lower depending on the desired performance requirements. The sensors may be sealed for water resistance or proofing and while some embodiments may be opened, for example to replace a battery held inside the sensor housing. Any other sensor having dimensions or capabilities that allow for measurement of any combination of one or more of orientation, position, velocity and/or acceleration that may couple to a piece of equipment or user may be utilized in one or more embodiments as a motion capture element.

Figure 9:
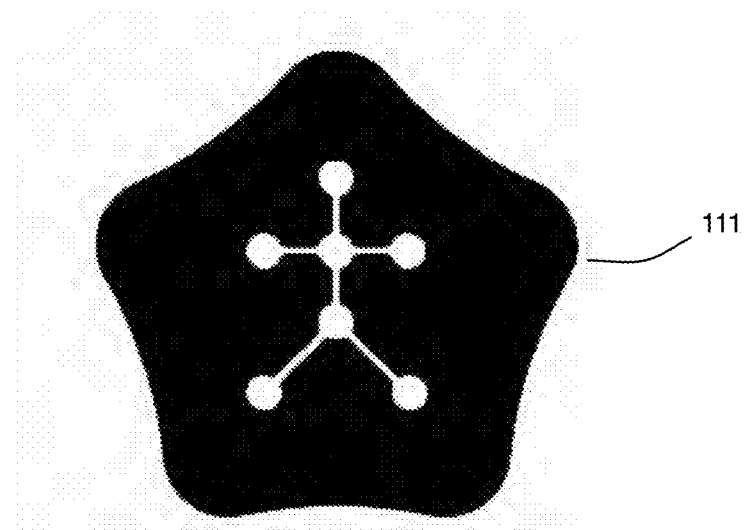
FIG. 9 illustrates a front view of FIG. 8.

FIG. 9 illustrates a front view of FIG. 8. In this figure, the visual marker is shown from above and signifies an instrumented user. The contrast between black and white allows for ease of capture.

Figure 10:
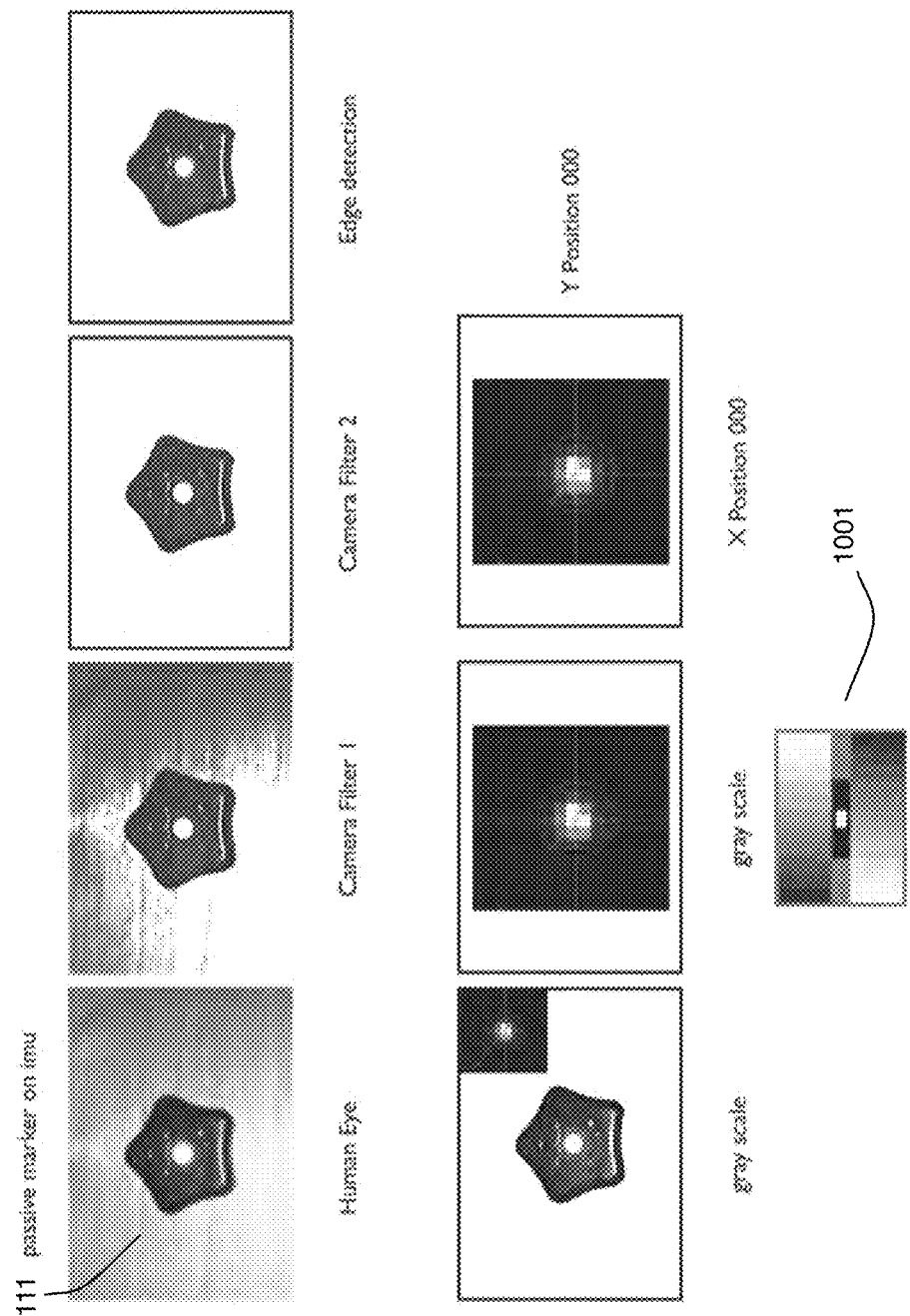
FIG. 10 illustrates an embodiment of the motion capture element implemented with a passive marker and gray scale images thereof to show how the marker can be tracked by obtaining an image and searching for a luminance change from black to white.

FIG. 10 illustrates an embodiment of motion capture element 111 implemented with a single white circle on a black passive marker and gray scale images thereof to show how the marker can be tracked by obtaining an image and searching for a luminance change from black to white as shown at point 1001. Any other image processing algorithm may be utilized to find an embodiment of the motion capture element within an image as one skilled in the art will recognize, for example based on a color difference or gradient detected in an image in the area of an embodiment of motion capture element 111.

Figure 11:
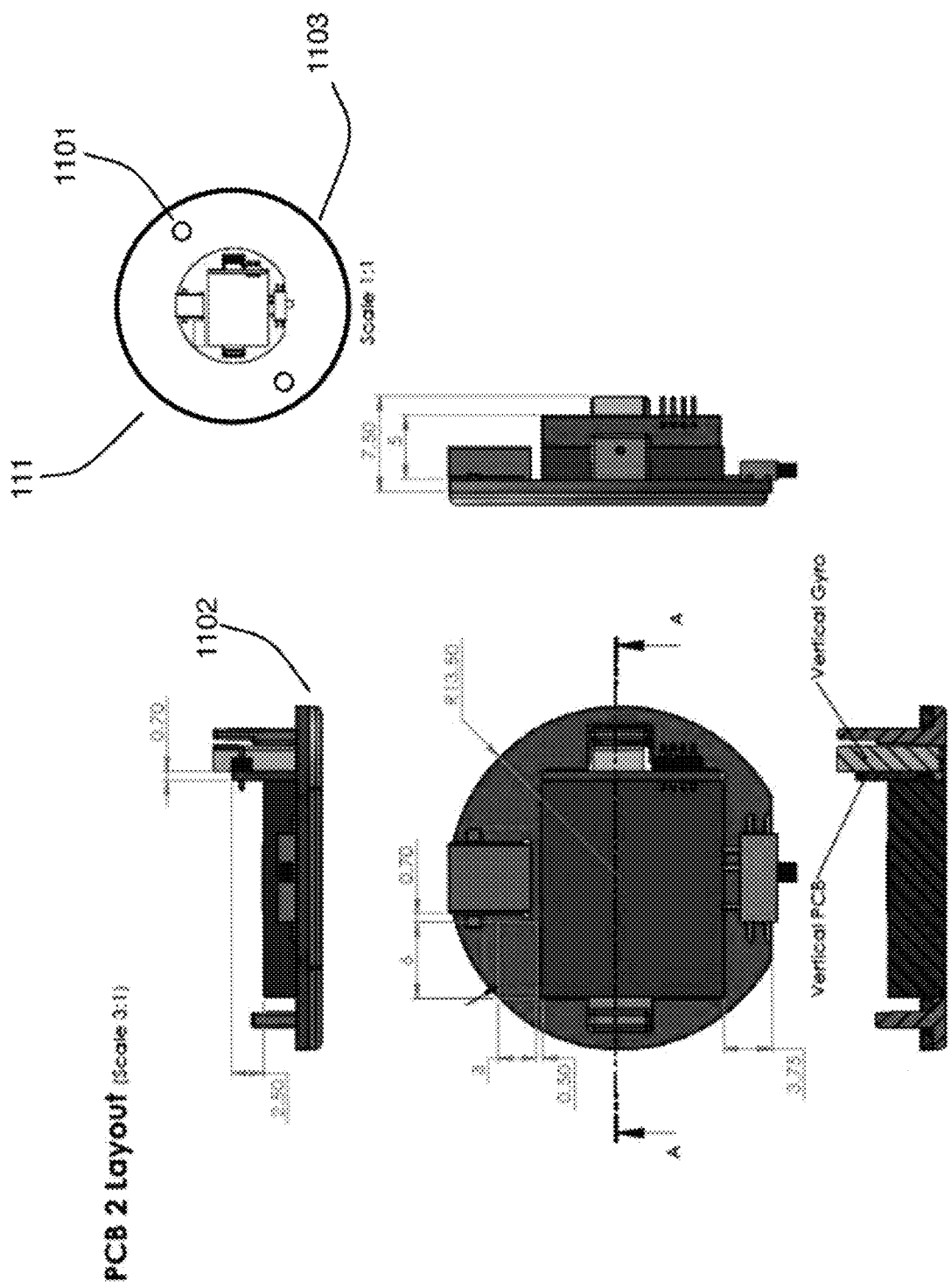
FIG. 11 illustrates a hardware implementation of the sensor portion of a motion capture element implemented as a wireless inertial measurement unit, and an embodiment as configured to couple with a weight port of a golf club for example.

FIG. 11 illustrates a hardware implementation of the sensor portion of a motion capture element implemented as a wireless inertial measurement unit, and an embodiment as configured to couple with a weight port of a golf club for example. Printed circuit board (PCB) may be utilized to hold the various components of the sensor including any orientation, position, velocity and/or accelerometers. Hole 1101 may be utilized as a screw hole or other coupling point for coupling motion capture element 111 to a piece of equipment, such as into a weight port of a golf club. Alternatively, threads at location 1102 or at location 1103 may be utilized to screw motion capture element 111 onto the piece of equipment. Any other method of coupling motion capture element to a piece of equipment or user is in keeping with the spirit of the invention. Embodiments of the invention may also be placed near the head of a golf club, in the handle of a golf club, or in any other piece of equipment. When placing an embodiment of the invention near the golf club head or handle, an adapter may be utilized so as to fit the apparatus to the specific make and/or model of the golf club. Each manufacturer has multiple types of weight port sizes, locations and shapes and any adapter that can for example screw into a weight port hole and also fit threads at location 1102 may be utilized as an adapter. For handles, any tube size for a given make or model of a club may be utilized as an adapter so long as it allows the components of embodiments of the invention to fit inside the golf club and withstand the forces involved with a golf club swing.

Figure 12:
FIG. 12 illustrates an embodiment of the motion capture element as configured to couple with different golf club types and a shoe.

FIG. 12 illustrates an embodiment of the motion capture element as configured to couple with different golf club types and a shoe. As shown in the leftmost figure, motion capture element 111 can couple directly to a piece of equipment such as a golf club in the rear portion of the club head. As the second from left figure illustrates, motion capture element 111 may couple onto the bottom of a piece of equipment, such as a golf putter. In addition, as the third figure from the left illustrates, motion capture element 111 may couple into the weight port of a piece of equipment, such as a driver. Furthermore, motion capture element may couple with a piece of equipment that is worn by the user, effectively coupling with the user as shown in the rightmost figure.

Figure 13:
FIG. 13 illustrates a close-up of the shoe of FIG. 12 along with a pressure map of a shoe configured with a pressure matt inside the shoe configured to output pressure per particular areas of the shoe.

FIG. 13 illustrates a close-up of the shoe of FIG. 12 along with a pressure map of a shoe configured with a pressure matt inside the shoe configured to output pressure per particular areas of the shoe. In this embodiment, motion capture element may also interface to a pressure sensing mat capable of producing pressure map 1301 from inside of the shoe and relay the pressure information to the mobile device for analysis. Alternatively, pressure sensors may be placed through the shoe, for example in a grid, to provide weight bearing information to the mobile device, for example wirelessly via the motion capture element. Each pressure sensor may couple to a transceiver or contain its own transceiver, or couple via wires or wirelessly to the motion capture element in order to transmit pressure data, for example to display on display 120. By color coding the map and displaying the map on display 120, a color graphic rating is thus obtained, which may include numerical ratings of the pressure signature when compared to saved pressure maps which resulted in good swings for example.

Figure 14:
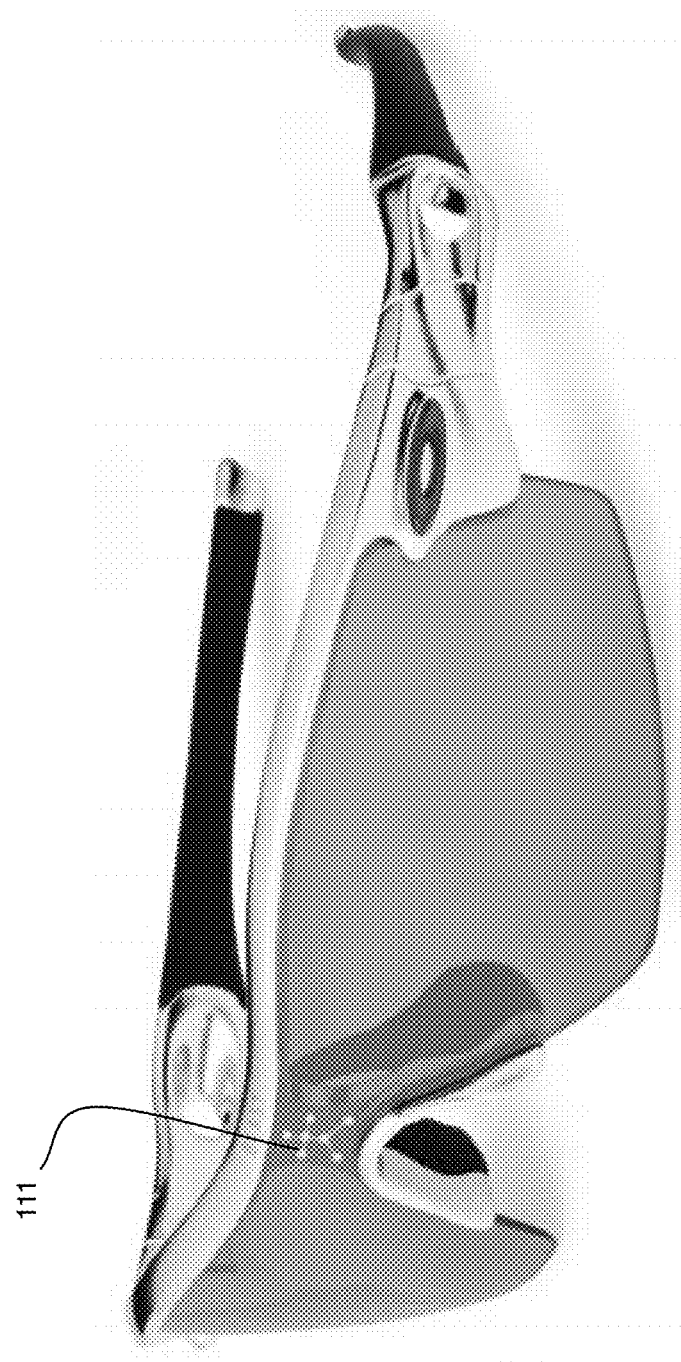
FIG. 14 illustrates an embodiment of sunglasses configured with an embodiment of the motion capture element.

FIG. 14 illustrates an embodiment of sunglasses configured with a motion capture element. In addition, the sunglasses may also include a video viewing device that may be utilized for display 120 so that the user may watch images of the user with motion analysis data via the sunglasses. In this manner, any computer 160, 105, or any other computer coupled to network 170 or Internet 171 may be utilized to obtain data and analyze data so that the resulting motion analysis data may be displayed on the sunglasses, for example for virtual reality and/or augmented virtual reality display. Viewing past performance data in the form of avatars that move according to motion capture data held in database 172 for example enables a user to view relative performance, i.e., a user would see a faster user's avatar running in front of the current user for example, or to play a game, i.e., tennis for example with an avatar of another user or the given user moving according to motion capture data in database 172. Playing games using actual stored motion capture data provides the most realistic virtual reality possible. For example, given one user having a motion capture element or more coupled with the user allows the user to play another user having a motion capture element, or play against a previously stored performance of the same user, or both, or play along with a historical figure such as a famous player whether still alive or not, or play against a data mined "constructed" player that has some combination or function of motion data mined from previous performances of motion data previously stored for one or more users.

Figure 15:
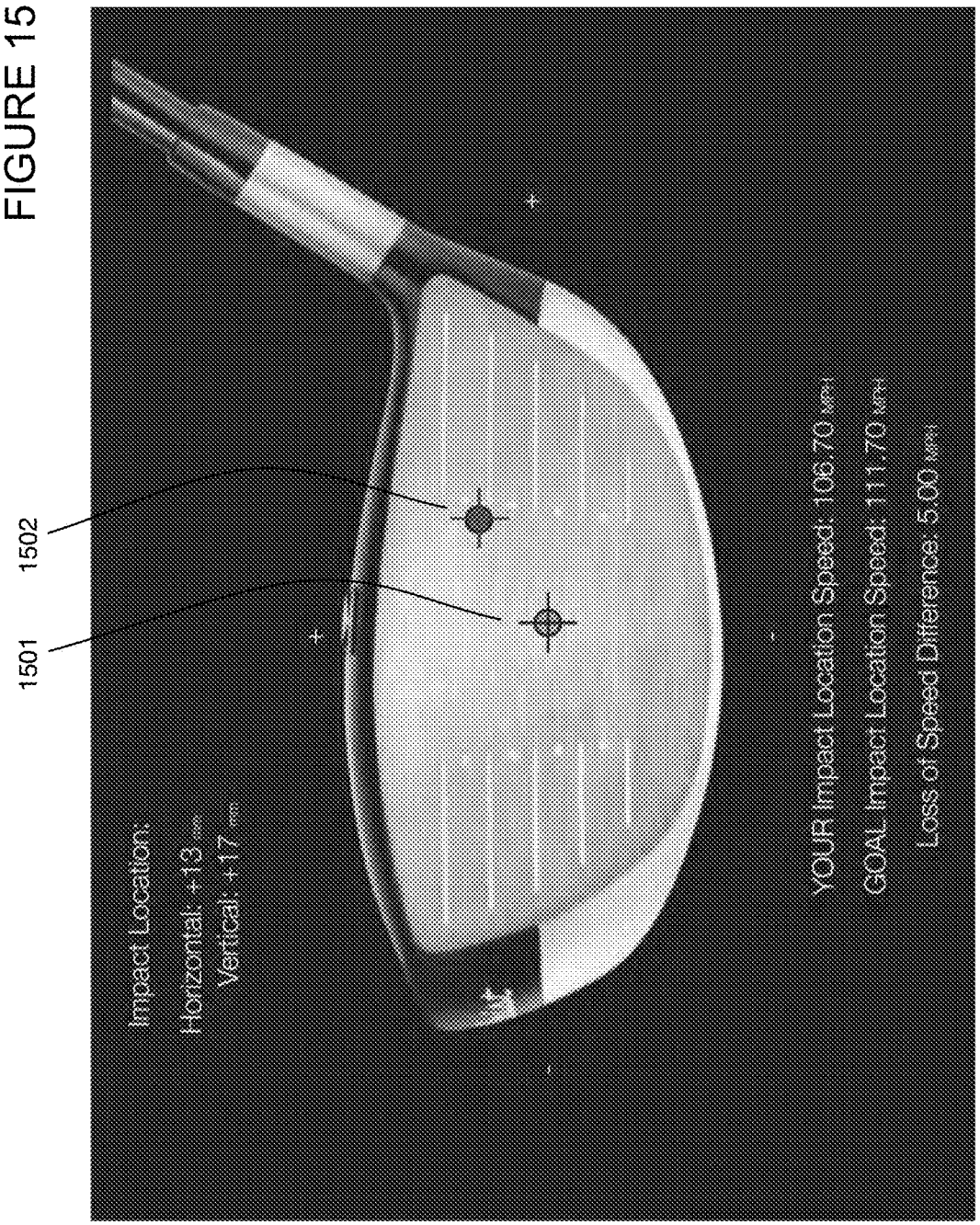
FIG. 15 illustrates an embodiment of a display that depicts the location of a golf ball strike as determined by the oscillations in the golf club face during and/or after the golf club impacts a golf ball.

FIG. 15 illustrates an embodiment of a display that depicts the location of a golf ball strike as determined by the oscillations in the golf club face during and/or after the golf club impacts a golf ball. In one or more embodiments of the invention, if the golf ball impacts the club at location 1501, then a particular frequency response is obtained via orientation or velocity sensors in motion capture element 111 that is coupled with the club shown. If the golf ball impacts the club at location 1502, then a distinct frequency response is obtained via the motion capture element 111 coupled to the club. One embodiment for determining where a ball impacts a club involves recording impacts from a variety of locations at a range of speeds and using the resulting frequency responses to determine which one is the closest to the impact detected. Impacts that occur high or low on the club face tend to produce a vertical axis oscillation of greater amplitude than impacts that occur at location 1501. Impacts that occur closer to the shaft tend to produce lower amplitude oscillations in the horizontal axis than impacts that occur further from the shaft. Hence, another method for determining impact is to form a ratio of the amplitude of horizontal to vertical axis frequency amplitude and then search for the closest match from a saved set of impact frequency responses and retrieve the x and y locations on the club face where the closest match has occurred. In another embodiment of the system, a series of impacts is recording at the center of the club and at 4 points away from the center along the positive x axis, (away from the shaft), positive z axis (above the center point of the face), negative x axis (near the shaft) and negative z axis (below the center point of the face) wherein the motion capture element transmits x, y and z velocities associated with the impact. The velocities are converted into the frequency domain and saved. Then, when determining an impact location for a test swing, an interpolation between the impact in question and the center point and 4 other points is performed to determine the location of the impact. Any other method of determining the impact location that does not require other sensors besides the motion capture element coupled to the club is in keeping with the spirit of the invention.

Figure 16:
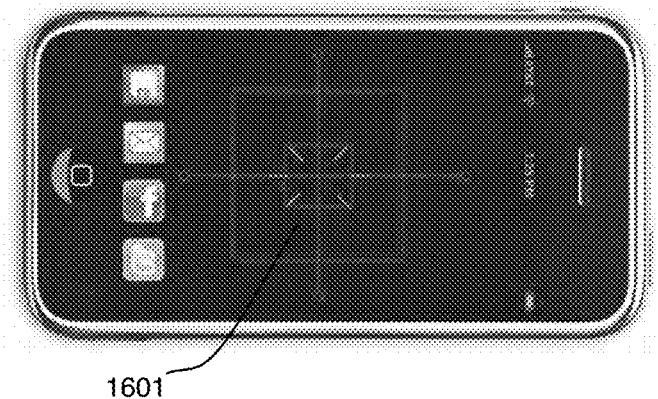
FIG. 16 illustrates a camera alignment tool as utilized with embodiments of the system to create normalized images for capture data mining.
Figure 17:
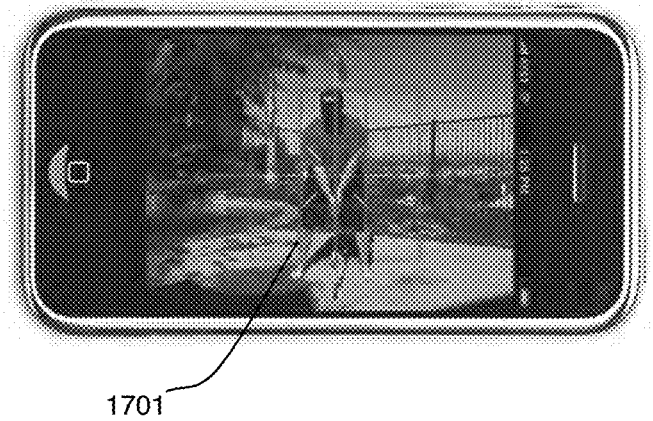
FIG. 17 illustrates a balance box and center alignment line to aid in centering a user to obtain image data.
Figure 18:
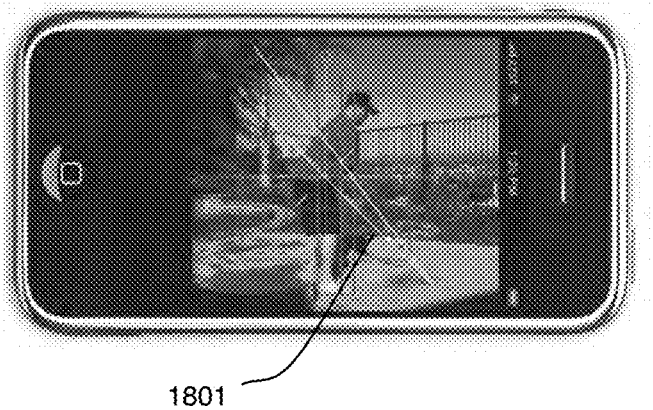
FIG. 18 illustrates a balance box and center alignment line, along with primary and secondary shaft lines to aid in centering and analyzing images of the user.

FIG. 16 illustrates a camera alignment tool as utilized with embodiments of the system to create normalized images for capture data mining. In this figure, level lines 1601 are shown that for example become brighter when the mobile device is level. Any other manner of displaying that the mobile device is level may also be utilized. Icons on the left side of the screen show that the motion capture data and images may be saved, emailed, or sent to popular social networking sites such as FACEBOOK® and TWITTER®. FIG. 17 illustrates a balance box and center alignment line to aid in centering a user to obtain image data. FIG. 18 illustrates a balance box and center alignment line, along with primary and secondary shaft lines to aid in centering and analyzing images of the user for use in capturing data from the side of the user. Once the user is centered, the computer may obtain data and images that are normalized to the horizontal plane.

Figure 19:
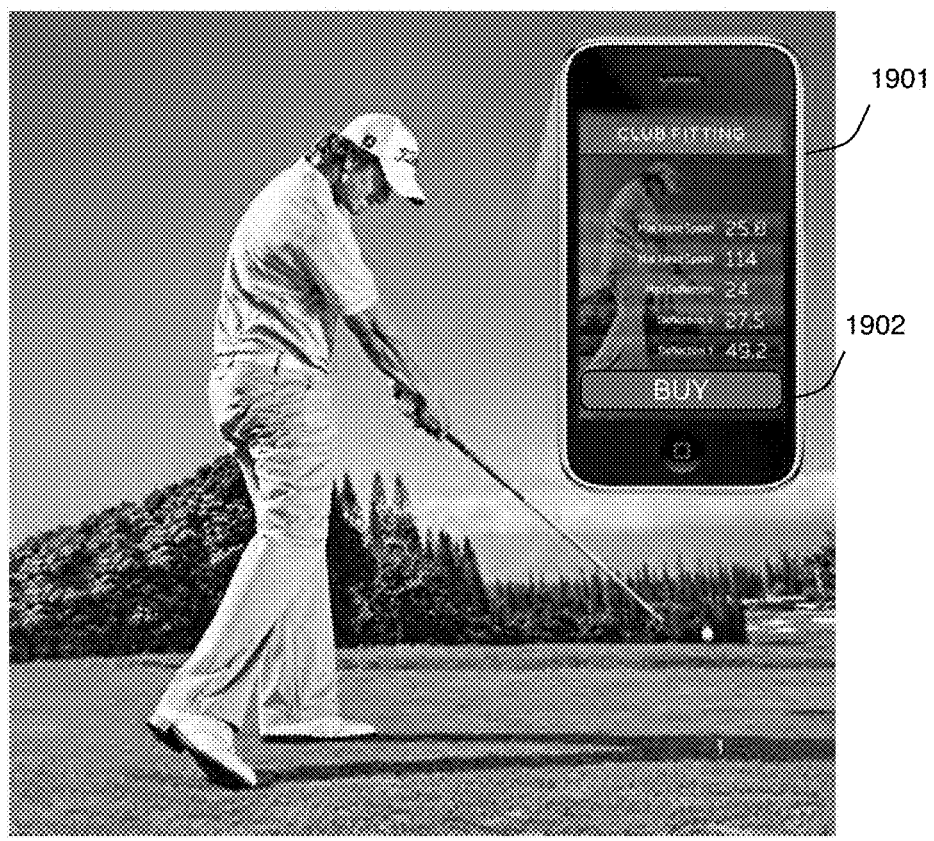
FIG. 19 illustrates an embodiment of the display configured to aid in club fitting for a user, wherein a user may test multiple clubs and wherein the display shows motion analysis data. For embodiments of the invention may be utilized to obtain sensor data that is utilized for purchase and order fulfillment options, buttons such as "purchase" and "customer order" may be utilized.

FIG. 19 illustrates an embodiment of the display configured to aid in club fitting for a user, wherein a user may test multiple clubs and wherein the display shows motion analysis data. For embodiments of the system that include purchase and order fulfillment options, buttons such as "purchase" and "customer order" may be utilized. Alternatively, a "buy" button 1902 may be shown in "club fitting" mode 1901 that enables a user to buy or custom order a custom club that the user is working with. In one or more embodiments of the invention the equipment identifier may be sent over Internet 171 to an Internet based drop shipper (or via website 173 for a salesperson to receive and communicate with the user, or in any other manner as one skilled in the art will appreciate including but not limited to text messaging, emails or phone calls to a sales person directly from the mobile computer with telephonic interface) along with user information for example on mobile computer 101 or in table 180 of FIG. 1B to ship the equipment to the address associated with the user. Table 180 may also include credit card information or other payment information for example.

The purchase may be made within a virtual reality environment for example during a game being played with remote, virtual or historical players for example, wherein the "Buy" button is viewed in virtual reality space and asserted for example by "touching" the virtual button or in any other manner. In addition, the Buy button may be displayed to the user when the system calculates that the particular player being displayed is similar to the user and wherein the app presents the make/model/size of the piece of equipment to buy. In addition, the average score for similar sized users using that piece of equipment may be shown to the user and a reduction in score may be presented to the user to shown the user how much the suggested piece of equipment would improve the user's average score. The user may for example be watching TV on the mobile device and not playing golf at the time for example, and still purchase the equipment based on the user's saved physical characteristics.

Figure 20:
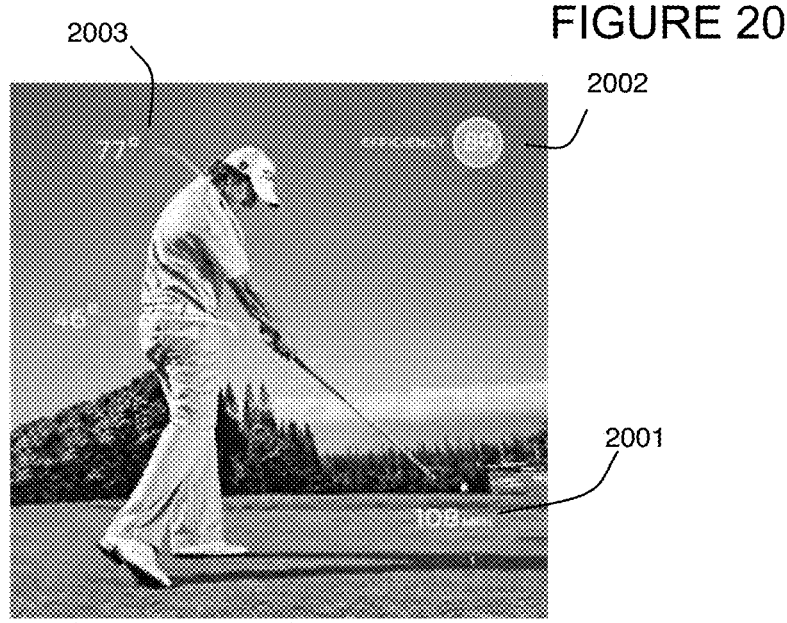
FIG. 20 illustrates an embodiment of the display configured to display motion analysis data along with the user, some of which is overlaid onto the user to aid in understanding the motion analysis data in a more human understandable format. In addition, motion analysis data associated with the user can be shown numerically as shown for example as "efficiency" of the swing, and the velocity of the swing.

FIG. 20 illustrates an embodiment of the display configured to display motion analysis data along with the user, some of which is overlaid onto the user to aid in understanding the motion analysis data in a more human understandable format. For example, rotation rings 2003 may be shown overlaid on one or more images of the user to shown the angle of the axis of rotation of portions of the user's body, such as shoulders and hips. In addition, motion analysis data associated with the user can be shown numerically as shown for example as "efficiency" of the swing 2002, and velocity of the swing 2001. The motion capture data and images may be saved to database 172 and later utilized to play a game against another player for example on a virtual reality golf course. Alternatively, or in combination, the data may be streamed between to distally located players with or without historical data, or the historical data may be saved on one or more machines and streamed between users without accessing the database for example. The player may be a historical player whose performance data has been analyzed and stored in the database for later game playing for example.

Figure 21:
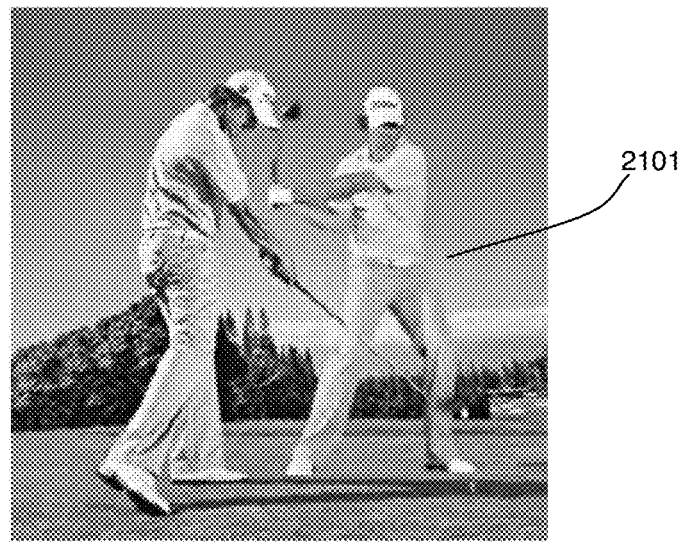
FIG. 21 illustrates an embodiment of the system configured to display a user from multiple angles when multiple cameras are available. One or more embodiments of the system may show one image of the user at a time in slow motion as the user moves, while changing the angle of the view of the user in normal time, which is known as BULLET TIME®.

FIG. 21 illustrates an embodiment of the system configured to display a user from multiple angles 2101 when multiple cameras are available. Any algorithm that may process images to eliminate backgrounds for example may be utilized to show multiple instances of the user on one background. Alternatively, one or more embodiments of the system may show one image of the user at a time in slow motion as the user moves, while changing the angle of the view of the user in normal time, which is known as BULLET TIME®.

Figure 22:
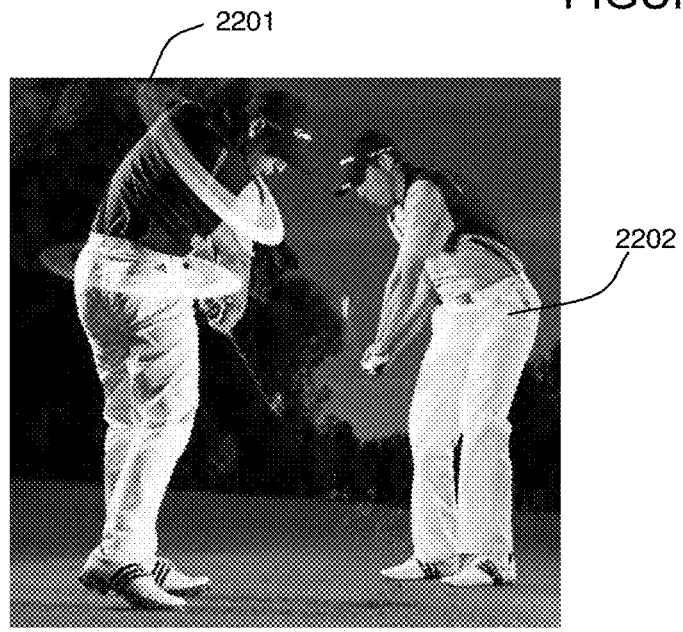
FIG. 22 illustrates another embodiment of the multi-angle display as is also shown in FIG. 21 wherein this figure also includes three-dimensional overlay graphics to aid in understanding the motion analysis data in a more human understandable manner.

FIG. 22 illustrates another embodiment of the multi-angle display as is also shown in FIG. 21. This figure also includes three-dimensional overlay graphics 2201 to aid in understanding the motion analysis data in a more human understandable manner. Second instance of the user 2202 may or may not be shown with the same overlay from a different angle.

Figure 23:
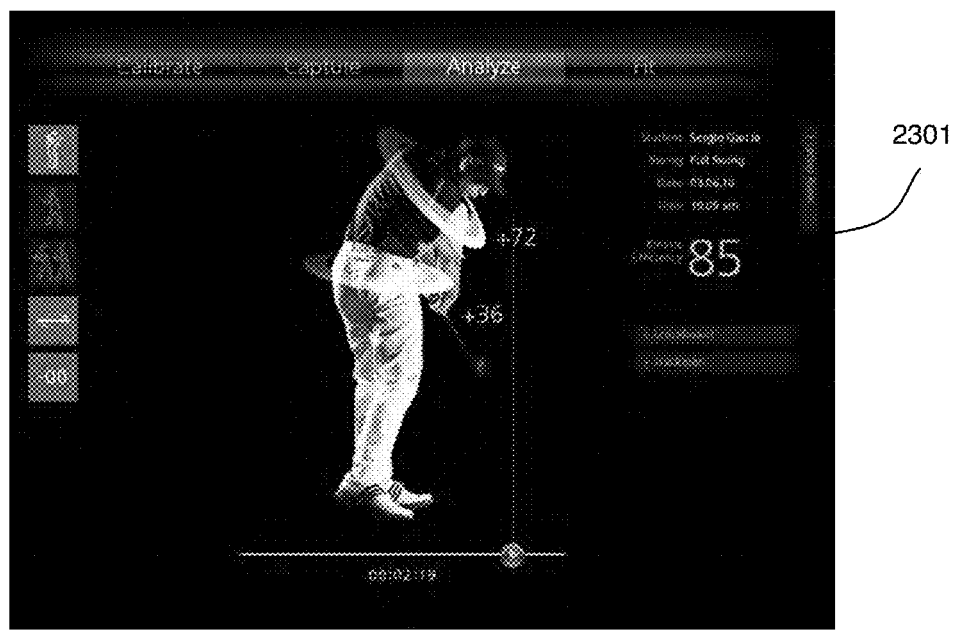
FIG. 23 shows an embodiment of the system configured to display motion analysis data on a mobile computer, personal computer, IPAD® or any other computer with a display device large enough to display the desired data.

FIG. 23 shows an embodiment of the system configured to display motion analysis data on a mobile computer, personal computer, IPAD® or any other computer with a display device large enough to display the desired data.

Figure 24:
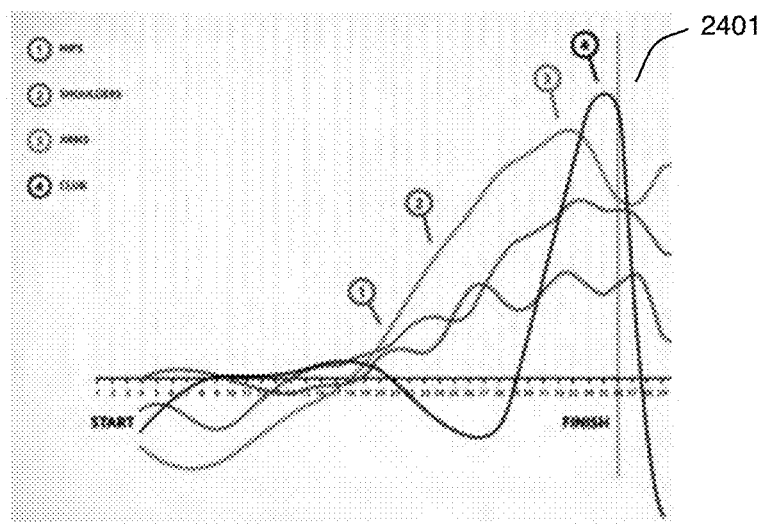
FIG. 24 illustrates a timeline display of motion analysis data that shows multiple sensor angular velocities in reference to the world or for example to a portion of the piece of equipment or object to hit or a virtual spine or a boney landmark, as obtained from sensors on a user and/or on a piece of equipment.
Figure 25:
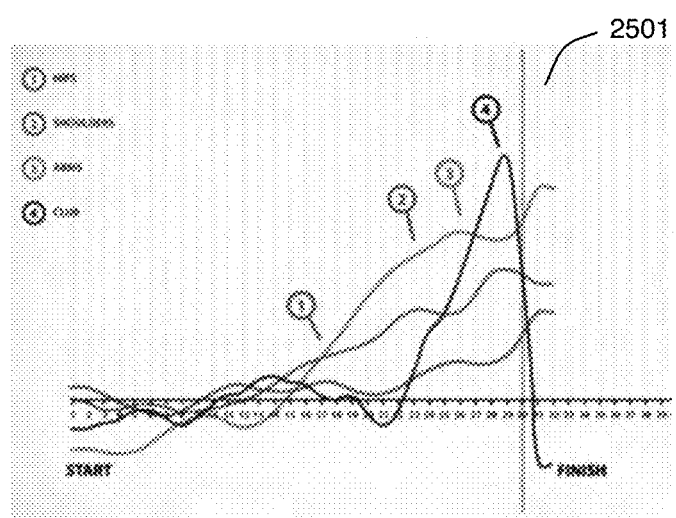
FIG. 25 illustrates a timeline display of motion analysis data that shows multiple sensor angular speeds obtained from multiple sensors on a second user and on a piece of equipment. Efficient movement pattern of body segments know as a kinetic chain and of kinematic segmental sequencing.

In any embodiments detailed herein, efficiency may be calculated in a variety of ways and displayed. For embodiments of the invention that utilize one motion capture element, then the motion capture element associated with the club head may be utilized to calculate the efficiency. In one or more embodiments of the invention, efficiency may be calculated as:

Efficiency=(90−angle of club face with respect to direction of travel)*$Vc/V$ max As more sensors are added further from the piece of equipment, such as in this case a club, the more refined the efficiency calculation may be. FIG. 24 illustrates a timeline display of motion analysis data that shows multiple sensor angular speeds obtained from multiple sensors on a user and on a piece of equipment. FIG. 25 illustrates a timeline display of angular speed of a second user. One or more embodiments of the system may calculate an efficiency based on relative times of the peaks of the hips, shoulders, arms and club for example. In one or more embodiments of the invention utilizing more than one motion capture element, for example on the handle and club head, the angular velocity Wa of the handle is divided by the angular velocity We of the club head to calculate efficiency with more information. By obtaining a large number of timelines from various professional athletes and determining average amplitudes of angular velocities of various body parts and/or timings, then more refined versions of the efficiency equation may be created and utilized. Old video may be analyzed by determining the difference in distances shown versus the time between frames for a particular video to determine speeds, which may be stored as previous motion capture data for use in virtual reality environments and scenarios.

Efficiency=(90−angle of club face with respect to direction of travel)*$Vc/V$ max*$Wa/Wc$*1.2

Figure 26:
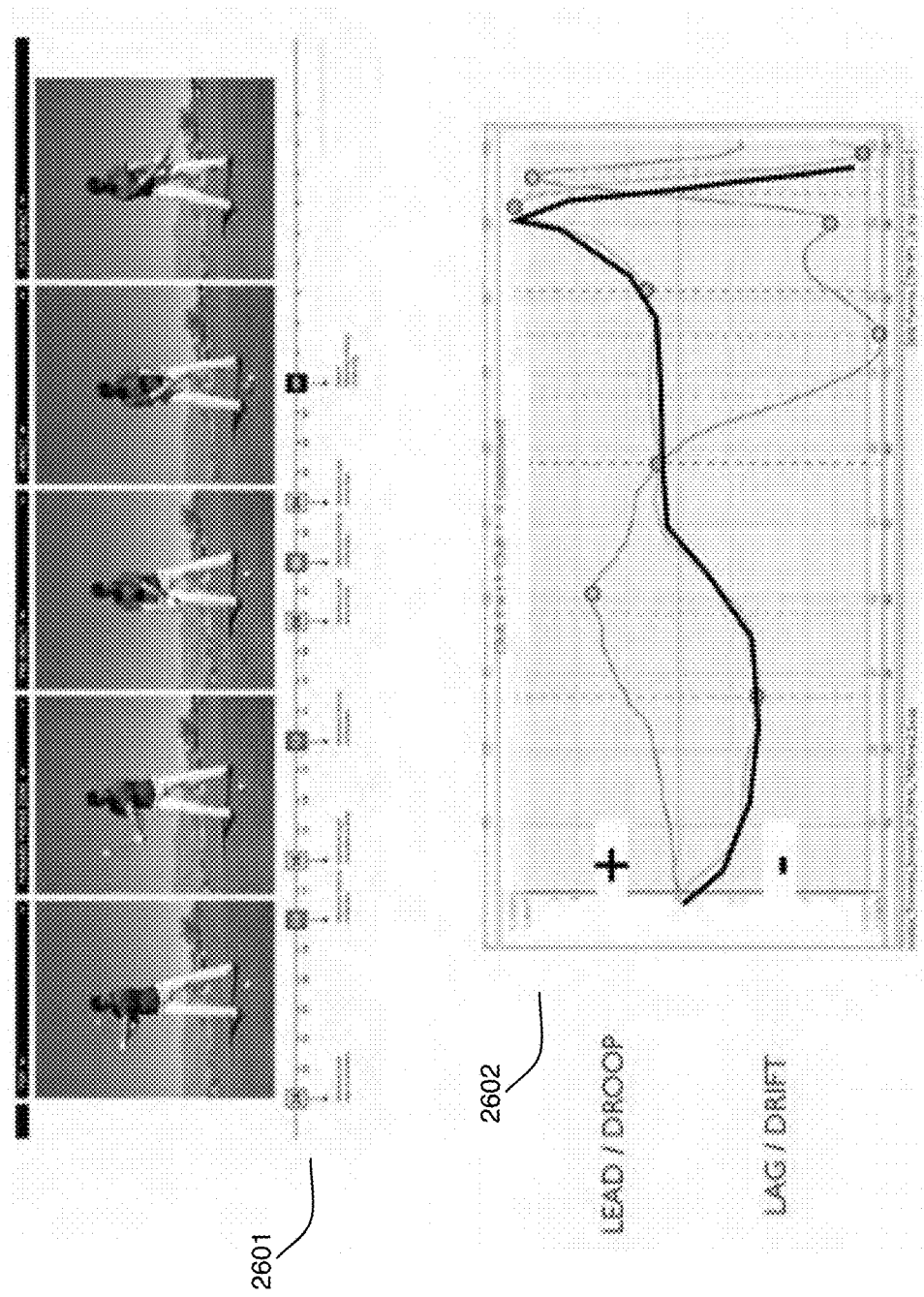
FIG. 26 illustrates a timeline display of a user along with peak and minimum angular speeds along the timeline shown as events along the time line instead of as Y-axis data as shown in FIGS. 24 and 25. In addition, a graph showing the lead and lag of the golf club along with the droop and drift of the golf club is shown in the bottom display wherein these values determine how much the golf club shaft is bending in two axes as plotted against time.

FIG. 26 illustrates a timeline display of a user along with peak and minimum angular speeds along the timeline shown as events along the time line instead of as Y-axis data as shown in FIGS. 24 and 25. In this unique view, the points in time where the peaks of the graphs of FIGS. 24 and 25 are shown as colored boxes that correspond to the colors of the graphs in FIGS. 24 and 25, yet in a more human understandable format that shows the relative timing of the peaks. In addition, at the bottom of FIG. 26 a graph showing the lead and lag of the golf club along with the droop and drift of the golf club is shown wherein these values determine how much the golf club shaft is bending in two axes as plotted against time.

One or more embodiments of the system may analyze the peaks and/or timing of the peaks in order to determine a list of exercises to provide to a user to improve the mechanics of the user. For example, if the arms are rotating too late or with not enough speed, a list can be provided to the user such as:

TABLE 1

| Arm Speed | Exercise |
|---|---|
| 1000-1500 degrees/sec | Impact Bag Drawbacks |
| 1501-1750 degrees/sec | Drawbacks |
| 1751-2000 degrees/sec | No drills |

The list of exercises may include any exercises for any body part and may displayed on display 120. For example, by asserting the "Training" button on the displays shown in FIG. 6, a corresponding body part list of exercises may be displayed on display 120.

Figure 27:
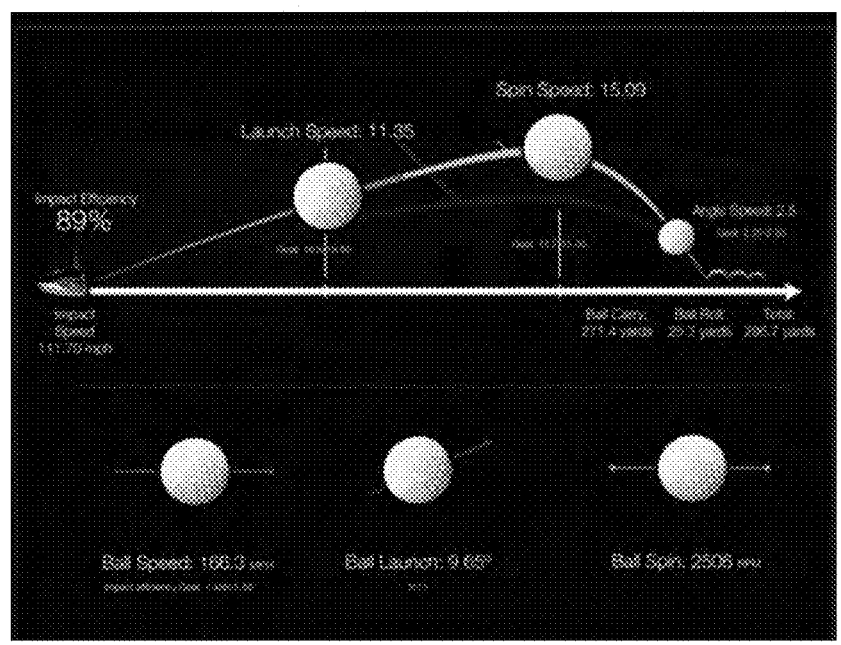
FIG. 27 illustrates a display of the calculated flight path of a ball based on the motion analysis data wherein the display is associated with any type of computer, personal computer, IPAD® or any other type of display capable of displaying images.
Figure 28:
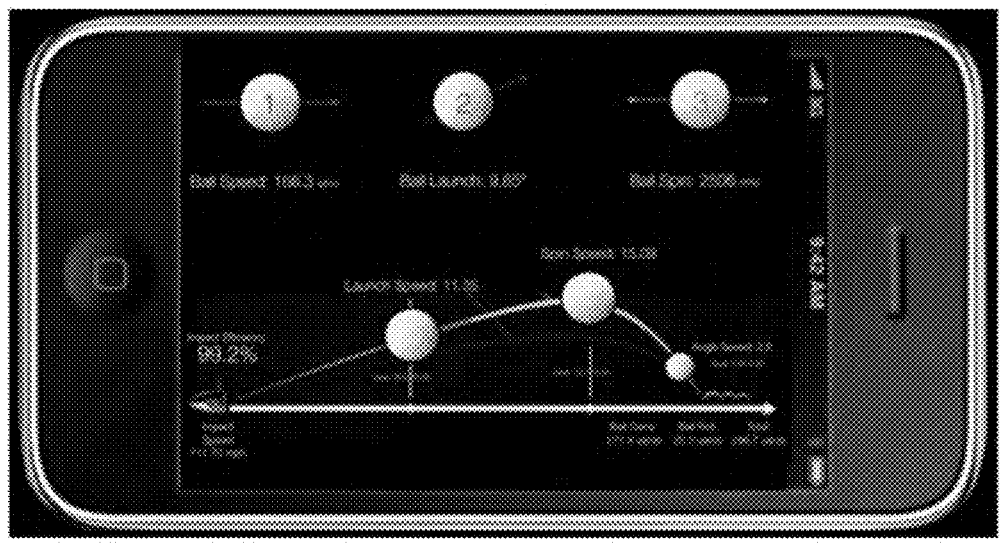
FIG. 28 illustrates a display of the calculated flight path of a ball based on motion analysis data wherein the display is coupled with a mobile device.

FIG. 27 illustrates a display of the calculated flight path 2701 of a ball based on the motion analysis data wherein the display is associated with any type of computer, personal computer, IPAD® or any other type of display capable of displaying images. FIG. 28 illustrates a display of the calculated flight path 2801 of a ball based on motion analysis data wherein the display is coupled with a mobile device.

After a swing of a golf club, and based on the club head speed as determined by motion capture element 111, the loft of the club and the angle at which the club strikes the ball (meaning that there is another motion capture element in the handle or near the hands of the user), a flight path may be calculated and displayed. Any model may be utilized as is known in the art to calculate the trajectory based on the club velocity as measure via motion capture element 111, one such model is described in a paper by MacDonald and Hanzely, "The physics of the drive in golf", Am. J. Phys 59 (3) 213-218 (1991). In addition, the actual distances calculated and store in the database, for example as differences between locations of shots for example in table 183 in database 172 may be used to verify or refine the model and may take into account the type of equipment, club and ball for example utilized to refine the model, for example with regression analysis, or in any other manner. See FIG. 37 for one embodiment of the equation used to calculate the accelerations in the x, y and z axes wherein:

x=laterally sideways (right is positive, left is negative)
y=down the fairway (always positive)
z=vertically upwards (up is positive, down is negative)
B=a constant dependent on the conditions of the air, an appropriate value=0.00512
u=vector of relative velocity between the ball and the air (i.e. wind), $u=v-v_w$
Cd=coefficient of drag which depends on the speed and spin of the ball
Cl=coefficient of drag which depends on the speed and spin of the ball
a=the angle between the vertical and the axis of rotation of the spinning ball
g=the acceleration due to gravity=32.16 ft/s2

A numerical form of the equations may be utilized to calculate the flight path for small increments of time assuming no wind and a spin axis of 0.1 radians or 5.72 degrees is as follows:

$$x \text{ acceleration}=-0.00512*(vx^2+vy^2+vz^2)^{(1/2)}*((46.0/(vx^2+vy^2+vz^2)^{(1/2)})*(vx)+(33.4/(vx^2+vy^2+vz^2)^{(1/2)})*(vy)*\sin(0.1))$$

$$y \text{ acceleration}=-0.00512*(vx^2+vy^2+vz^2)^{(1/2)}*((46.0/(vx^2+vy^2+vz^2)^{(1/2)})*(vy)-(33.4/(vx^2+vy^2+vz^2)^{(1/2)})*((vx)*\sin(0.1)-(vz)*\cos(0.1)))$$

$$z \text{ acceleration}=-32.16-0.00512*(vx^2+vy^2+vz^2)^{(1/2)}*((46.0/(vx^2+vy^2+vz^2)^{(1/2)})*(vz)-(33.4/(vx^2+vy^2+vz^2)^{(1/2)})*(vy)*\cos(0.1))$$

Figure 29:
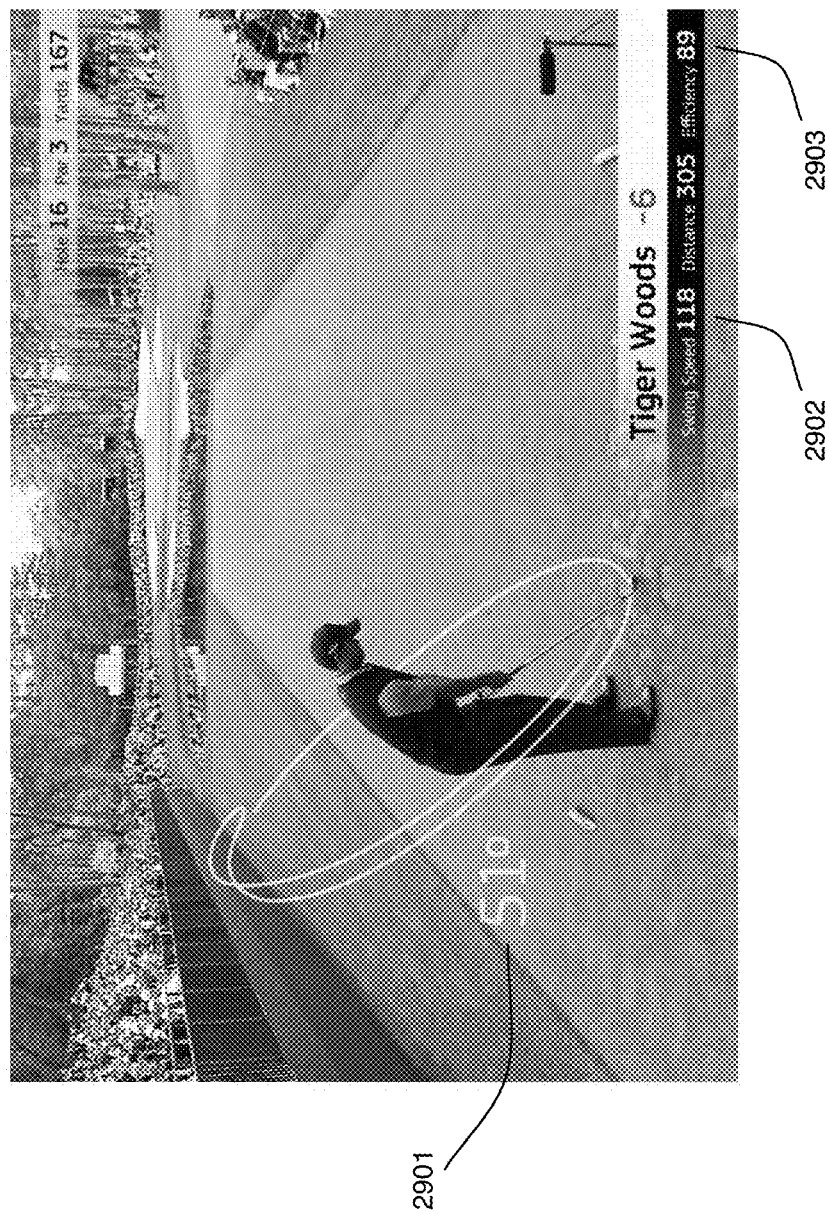
FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane in which the swing takes place versus the horizontal plane. In addition, other motion analysis data may be shown such as the swing speed, distance (calculated or actual) and efficiency.

FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane 2901 in which the swing takes place versus the horizontal plane. In addition, other motion analysis data may be shown such as the swing speed 2902, distance (calculated or actual) and efficiency 2903. This information or information in any other display described herein may be shown with or relative to data mining results of past performances of the player or other player for example based in any manner.

Figure 30:
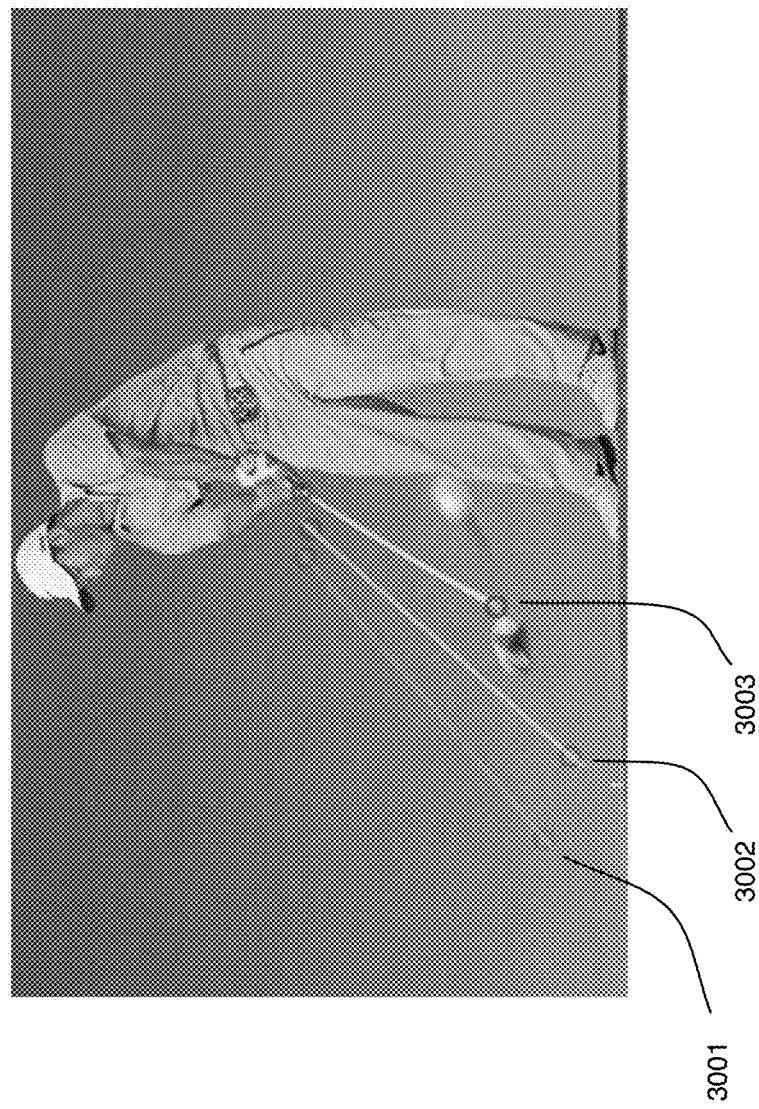
FIG. 30 illustrates a display of the swing path with a strobe effect wherein the golf club in this example includes sensors on the club head and near the handle, or optionally near the hands or in the gloves of the user. Optionally, imaged based processing from a high-speed camera may be utilized to produce the display. The swing path for good shots can be compared to swing paths for inaccurate shots to display the differences in a human understandable manner.

FIG. 30 illustrates a display of the swing path with a strobe effect wherein the golf club in this example includes sensors on the club head and near the handle, or optionally near the hands or in the gloves of the user. Optionally, imaged based processing from a high-speed camera may be utilized to produce the display. A line or captured portion of the actual shaft from images may be displayed at angle 3001, 3002 and 3003 for example. The swing path for good shots can be compared to swing paths for inaccurate shots to display the differences in a human understandable manner. The distance between the club head in pixels may be utilized in combination with the length of the club and angle thereof to determine the speed of the club based on the time between images. The calculated speed and various angles may be stored for later use in a virtual reality game for example.

Figure 31:
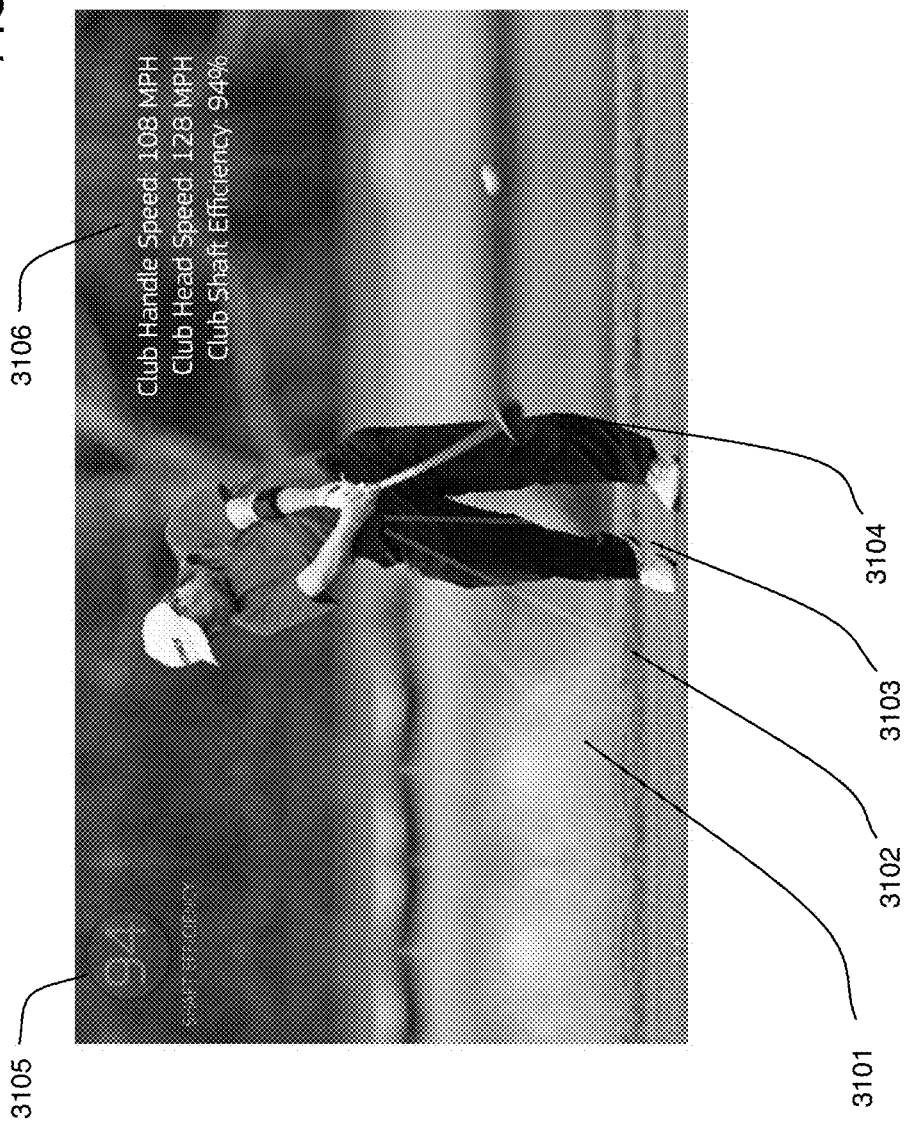
FIG. 31 illustrates a display of shaft efficiency as measured through the golf swing. For example, by obtaining motion capture data near the club head and club handle, graphical strobe effects and motion analysis data can show the club head speed, club handle speed and club shaft efficiency in normal time or slow motion.

FIG. 31 illustrates a display of shaft efficiency 3105 as measured through the golf swing. For example, by obtaining motion capture data near the club head and club handle, graphical strobe effects and motion analysis data can show the club head through time at 3101, 3102, 3103 and 3104 and also display speed, club handle speed and club shaft efficiency at 3106 in normal time or slow motion.

Figure 32:
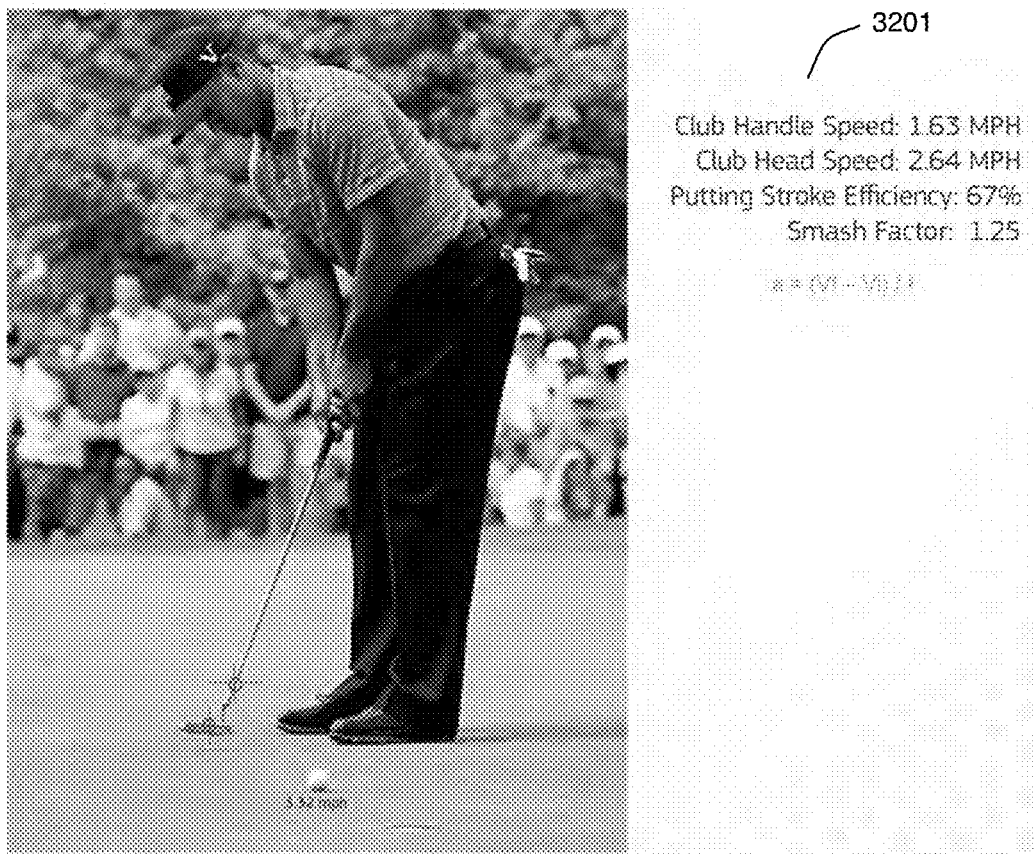
FIG. 32 illustrates a display of putter head acceleration based on at least one sensor near the putter head, for example as coupled into the weight port of a putter. The various quantities from the motion analysis data can be displayed to aid in understanding acceleration patterns for good putts and bad putts to help viewers understand acceleration in a more human understandable manner.

FIG. 32 illustrates a display of putter head speed and/or acceleration based on at least one sensor near the putter head, for example as coupled into the weight port of a putter. The various quantities from the motion analysis data can be displayed at 3201 to aid in understanding speed and/or acceleration patterns for good putts and bad putts to help viewers understand speed and/or acceleration in a more human understandable manner.

Figure 33:
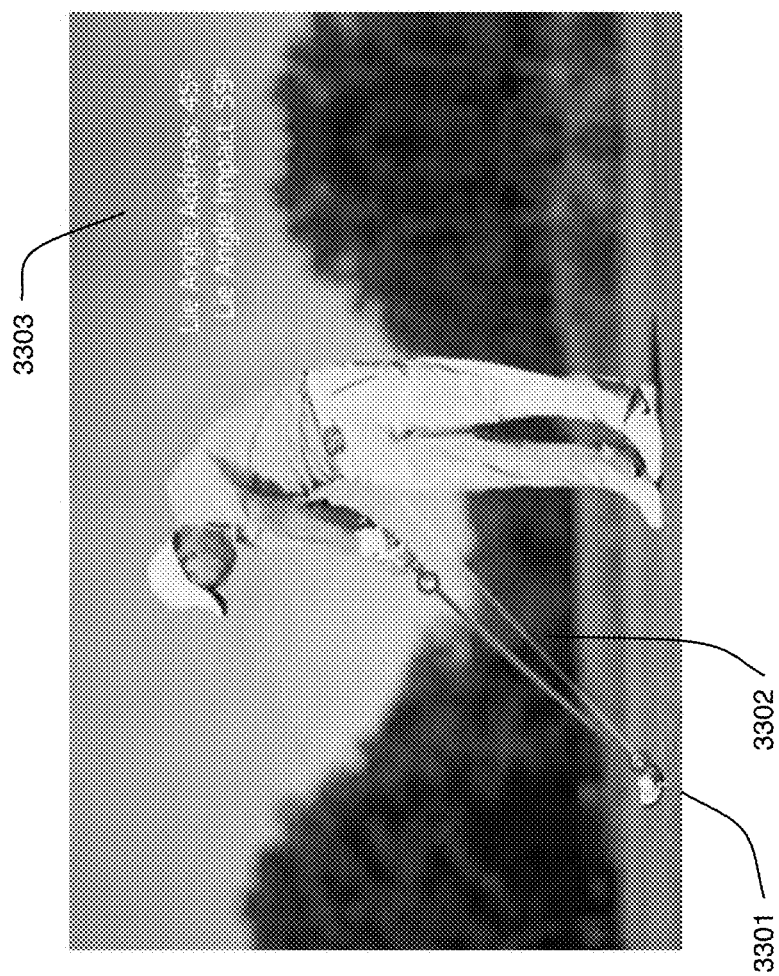
FIG. 33 illustrates a display of dynamic lie angle, wherein the lie angle of the player at address before swinging at the ball can be compared to the lie angle at impact to help the viewer understand how lie angle effects loft and ball flight.

FIG. 33 illustrates a display of dynamic lie angle, wherein the lie angle of the player at address 3302 before swinging at the ball can be compared to the lie angle at impact 3301 to help the viewer understand how lie angle effects loft and ball flight, while quantitatively showing the values at 3303.

Figure 34:
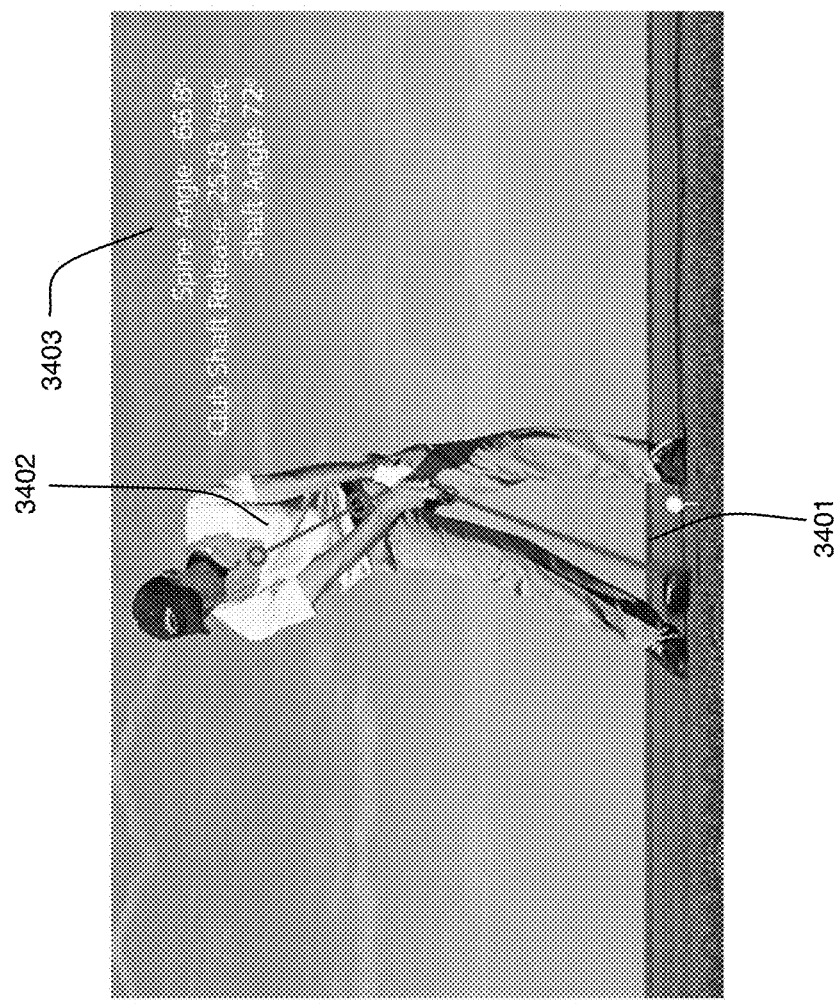
FIG. 34 illustrates a display of shaft release; wherein the angular release velocity of the golf shaft is a large component of the efficiency of a swing. As shown, a display of a golfer that has sensors near his waist and hips and sensors on the golf club head and handle, or as determined through image processing with or without visual markers, is shown with the motion analysis data.

FIG. 34 illustrates a display of shaft release, wherein the angular release velocity of the golf shaft is a large component of the efficiency of a swing. As shown, a display of a golfer that has sensors near his waist and hips (to produce spine angle 3402) and sensors on the golf club head and handle (to produce shaft angle 3401), or as determined through image processing with or without visual markers, is shown along with the motion analysis data including club shaft release in degrees per second at 3403.

Figure 35:
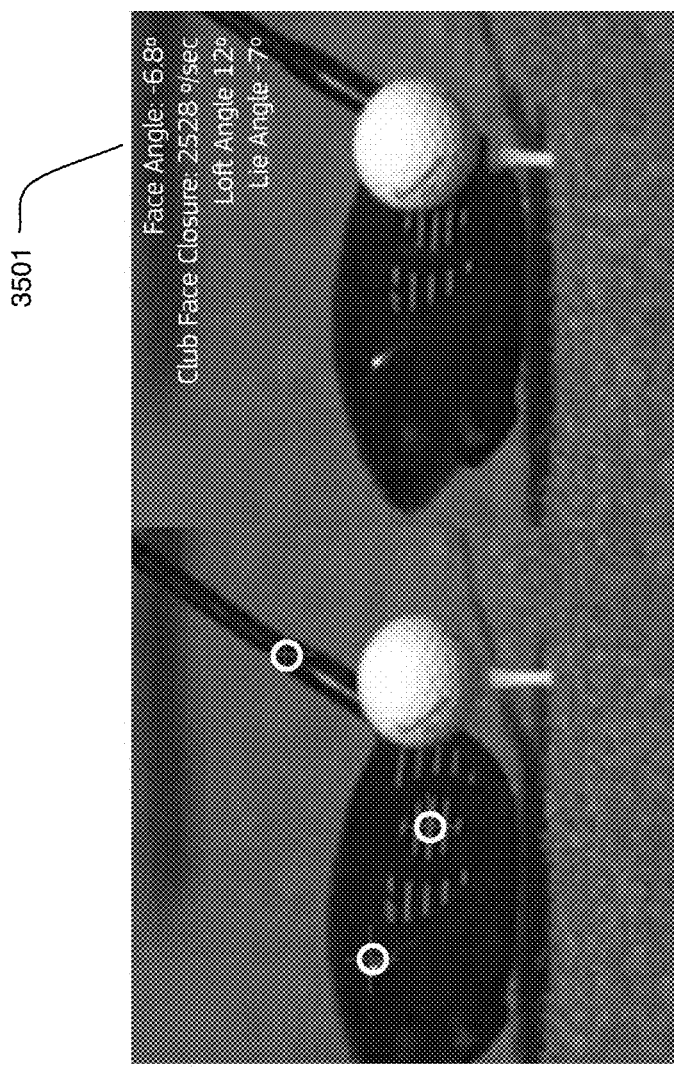
FIG. 35 illustrates a display of rotational velocity wherein the face angle, club face closure in degrees per second, the loft angle and lie angle are shown as obtained from a motion capture element on the club head for example.

FIG. 35 illustrates a display of rotational velocity wherein the face angle, club face closure in degrees per second, the loft angle and lie angle are determined from a motion capture sensor coupled with the club head for example and numerically shown at 3501. In one or more embodiments of the invention, a piece of equipment that includes two motion capture elements on opposing ends of the equipment, for example in the club head and handle of a golf club may include a calibration stage wherein the club face angle which is known and the angular orientations of the mounted motion capture sensors are calibrated so that their exact offsets for example with respect to the orientation of the shaft of the golf club is taken into account. In this manner, fitting experts and performance data in general related to the club can be normalized to the actual orientation of the club to ensure consistent data. Any of the previous video images may be utilized in virtual reality simulations, scenarios or games by determining the angles, speeds, accelerations or other changes between known time differences in each frame of video. For example for 30 frames per second, each image in the video differs by 0.033 seconds, by knowing the size of a club, the distance between the location of the club in successive frames, divided by the time between frames is equal to the velocity of the club, i.e., v=d/t. Any method of calculating motion or any derivative thereof based on different locations of objects in video is in keeping with the spirit of the invention.

Figure 36:
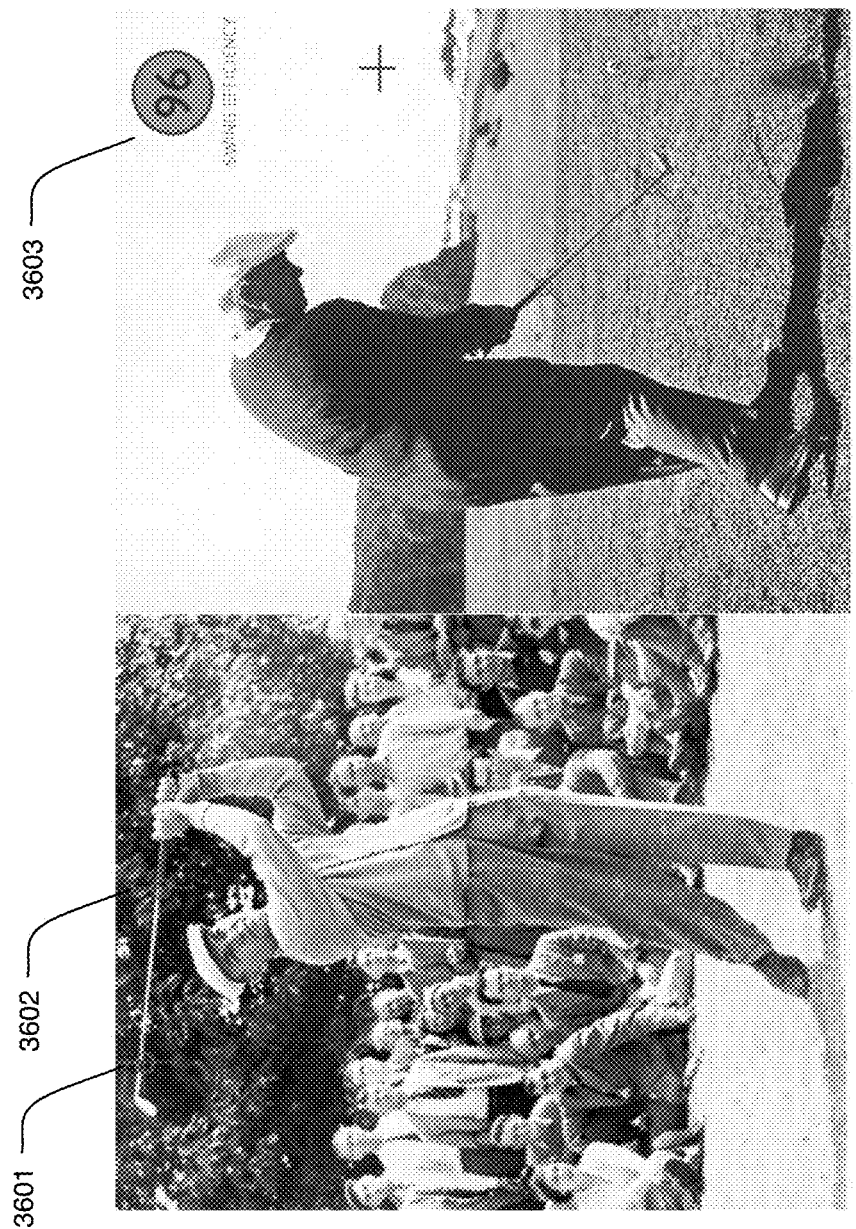
FIG. 36 illustrates a display of historical players with motion analysis data computed through image processing to show the performance of great players.

FIG. 36 illustrates a display of historical players with motion analysis data computed through image processing to show the performance of great players. By tracing and determining the locations of two points 3601 and 3602 on each player's golf club as shown and knowing the height of the players and/or lengths of their clubs and angle at which the images where taken, distances and thus velocities of the golf clubs may be determined to calculate numerical values as shown at 3603. This information may be stored posthumously in database 172 and data mining may be performed using the data as previously described. Users 150 may be compared against the greats and displayed on any computer described herein for example so long as the computer includes a display. In one or more embodiments, the players shown may be avatars in a virtual reality game, which are moving in concert with real instrumented players or data from a previous performance of the same or other user or the motion of a historical player as analyzed in one or more embodiments of the invention. Any model or avatar of a user, whether following the motion of an instrumented user, or previous motion of the user or another user or historical player may be utilized in displaying players in a virtual reality game, albeit using motion capture data whether calculated or from a motion capture sensor associated with a player or piece of equipment. Also shown is a red cross in the right image below the 96 power factor which is an aim assist or aim guide that may be utilized by a player in a virtual reality environment to help in deciding where to aim.

Figure 36A:
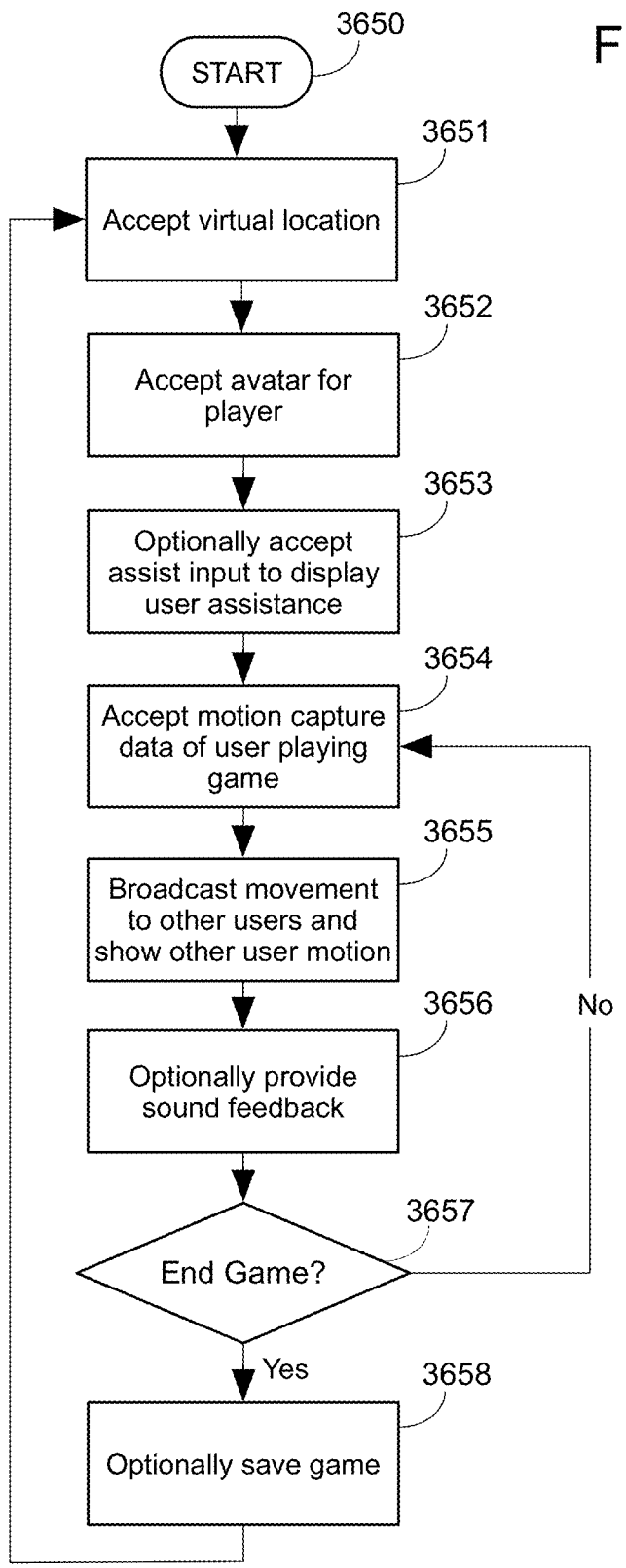
FIG. 36A illustrates a method implemented by the system to enable a virtual game to be played between a player instrumented with a motion capture sensor, along with an optional second user or previous performance of the first user along with an optional historical figure.

In one scenario, a first user buys an instrumented piece of equipment and decides to play a virtual game as is illustrated in FIG. 36A. The method begins at 3650. The first user selects a real or virtual location to play the game, for example the Master's Tournament of 1960 and the system accepts this at 3651. This may include a broadcast of the game or otherwise enable a group to find to play with, or the selection any historical player to play with, or previous motion from the same player, or otherwise enables other users to find the first user to enter the game. The first user selects an avatar that the system accepts at 3652, for example the player shown on the right or a virtual character of any type. The first user may optionally select an aim assist/swing assist that the system accepts at 3653, for example to display a cross hair to help select where to shoot at, as shown in the right image and based on the wind at the particular golf course the user is playing at or the simulated wind speed and direction. The first user plays the game and views the motion of the avatar in the VR as the user accepts motion capture data from the user and the avatar is moved accordingly and displayed by the system at 3654, for example wearing the VR glasses shown in FIG. 14. The system then broadcasts the motion data to the other user(s) and shows the other user's motion when they take turns playing at 3655. As users play, they may track each other's metrics over the net or locally, and/or see the metrics of the historical player or previously stored data of the first or second user. In one or more embodiments, the users may optionally hear feedback based on shots as presented by the system at 3656, for example cheers or boos or pleasant tones or not so pleasant tones for a bad shot. If the users are done playing as accepted by the system at 3657, the users may save the game at 3658 and play the game back later, for example retrieve the data from database 172 at a later time. Otherwise, the system accepts motion capture data of any real users and broadcasts the motion to the virtual reality environment for the other real users to see at 3654 and 3655 until they finish or otherwise quit the game.

FIG. 37 illustrates one embodiment of the equations used for predicting a golf ball flight path as used to produce displays as shown in FIGS. 27 and 28.

While the ideas herein disclosed has been described by means of specific embodiments and applications thereof, numerous modifications and variations could be made thereto by those skilled in the art without departing from the scope of the invention set forth in the claims.

What is claimed is:

1. A motion capture data fitting system comprising:
   at least one motion capture element coupled to or held by a first user or coupled to or held by a piece of equipment and configured to capture motion capture data during a movement of said first user or said piece of equipment performed by said first user, said at least one motion capture element comprising a wireless communication interface configured to transmit said motion capture data from the at least one motion capture element;
   a database comprising measurements associated with a plurality of other users, and,
   an application configured to execute on a computer that is configured to wirelessly communicate with said at least one motion capture element, wherein the application is configured to
      accept said motion capture data from at least one the motion capture element via the wireless communication interface;
      calculate at least one measurement
         of a characteristic of said first user or
         of said movement of said piece of equipment performed by said first user
         based on the motion capture data;
      perform a comparison of said at least one measurement of said characteristic or of said movement to said database of said measurements associated with said plurality of other users; and,
      present information associated with an optimally fit or sized piece of equipment based on said comparison.

2. The motion capture data fitting system according to claim 1 wherein said application is further configured to identify a user of said plurality of other users having a maximum value correlation with said at least one measurement associated with said first user.

3. The motion capture data fitting system according to claim 1 wherein said at least one measurement represents a height or an arm length, or a torso length, or a leg length of the first user or any combination thereof.

4. The motion capture data fitting system according to claim 1 wherein said at least one measurement represents a wrist to floor measurement of the first user.

5. The motion capture data fitting system according to claim 1 wherein said at least one measurement represents a hand size or longest finger size of the first user or both the hand size and the longest finger size of the first user.

6. The motion capture data fitting system according to claim 1 wherein said application is further configured to:
   display one or more images to enable a viewing of a sporting event.

7. The motion capture data fitting system according to claim 1 wherein said application is further configured to:
   accept an input from the first user to purchase said optimally fit or sized piece of equipment.

8. The motion capture data fitting system according to claim 1 wherein said at least one measurement comprises: a range of motion between a first and second rotational value.

9. The motion capture data fitting system according to claim 1 wherein said at least one measurement comprises: a speed of the first user.

10. The motion capture data fitting system according to claim 1 wherein said application is further configured to:
    prompt the first user for an age of the first user;
    identify a second user of said plurality of other users wherein said second user has an age similar to said age of said first user.

11. The motion capture data fitting system according to claim 1 wherein said application is further configured to:
    present information associated with a grip or length or a stiffness of said optimally fit or sized piece of equipment, or any combination thereof.

12. The motion capture data fitting system according to claim 1 wherein said application is further configured to:
    present information associated with a model or manufacturer of said optimally fit or sized piece of equipment or any combination thereof.

13. The motion capture data fitting system according to claim 1 wherein said computer is further configured to:
    predict a first derivative or other derivate based on age or growth with respect to time to determine said optimally sized piece of equipment for a current point in time or for a longest time that said optimally sized piece of equipment should last for the first user.

14. The motion capture data fitting system according to claim 1 wherein said computer is further configured to:
    present one or more of exercises and stretches that would improve performance to a predicted performance level based on performance data associated with the plurality of other users.

15. The motion capture data fitting system according to claim 1 wherein said computer is further configured to:
    present equipment that would be appropriate for an increase in strength or flexibility, such that the first user can grow into, or improve into said equipment.

16. The motion capture data fitting system according to claim 1 wherein said computer is further configured to:
    detect areas of a body of the first user indicative of injury associated with the motion capture data.

17. The motion capture data fitting system according to claim 1 wherein said piece of equipment comprises a shoe.

18. The motion capture data fitting system according to claim 17 wherein said at least one measurement of a characteristic of said first user or of said movement of said piece of equipment performed by said first user comprises a gait analysis.

19. The motion capture data fitting system according to claim 1 wherein said computer is further configured to:
    prompt said first user to move the at least one motion capture element to a first location;
    accept a first motion capture data from the at least one motion capture element at the first location via the wireless communication interface;
    prompt the first user to move the at least one motion capture element to a second location or rotational value;
    accept a second motion capture data from the at least one motion capture element at the second location or the rotational value via the wireless communication interface;
    calculate a distance or rotation between the first and second location or the rotational value based on the first and second motion capture data.

20. The motion capture data fitting system according to claim 1 wherein said computer is further configured to:

prompt the first user to move through a movement;
accept a first motion capture data from the at least one motion capture element for the movement via the wireless communication interface;
calculate a speed for the movement based on the first motion capture data.

21. The motion capture data fitting system according to claim 1 wherein said application is further configured to:
recognize when the at least one motion capture element is removed from the piece of equipment based on the motion capture data.

22. The motion capture data fitting system according to claim 1 wherein said application is further configured to:
recognize when or where the at least one motion capture element is coupled with the piece of equipment or the first user based on the motion capture data.

23. The motion capture data fitting system according to claim 1 wherein said computer is further configured to:
recognize when the at least one motion capture element is removed from the piece of equipment and coupled with a second piece of equipment based on the motion capture data.

\* \* \* \* \*

UNITED STATES PATENT AND TRADEMARK OFFICE
CERTIFICATE OF CORRECTION

PATENT NO. : 10,881,908 B2  
APPLICATION NO. : 16/512631  
DATED : January 5, 2021  
INVENTOR(S) : Michael Bentley, Bhaskar Bose and Ryan Kaps Page 1 of 1

It is certified that error appears in the above-identified patent and that said Letters Patent is hereby corrected as shown below:

In the Claims

Column 43, Line 26, Claim 1, replace "accept said motion capture data from at least one the" with --accept said motion capture data from the at least one--.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*